US012698335B2

(12) United States Patent
Bover et al.

(10) Patent No.: US 12,698,335 B2
(45) Date of Patent: Aug. 4, 2026

(54) ANTI-BST2 ANTIBODIES TARGETING BST2 LONG ISOFORM

(71) Applicant: BOARD OF REGENTS, THE UNIVERSITY OF TEXAS SYSTEM, Austin, TX (US)

(72) Inventors: Laura Del Carmen Bover, Houston, TX (US); Felipe Amaya-Manzanares, Houston, TX (US); Long Vien, Houston, TX (US); Ahmed Muhsin, Houston, TX (US); Janis D Johnson, Houston, TX (US); Julio Pollarolo, Houston, TX (US); Zhuang Wu, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 782 days.

(21) Appl. No.: 18/002,014

(22) PCT Filed: Jun. 17, 2021

(86) PCT No.: PCT/US2021/037920
§ 371 (c)(1),
(2) Date: Dec. 15, 2022

(87) PCT Pub. No.: WO2021/257894
PCT Pub. Date: Dec. 23, 2021

(65) Prior Publication Data
US 2023/0235074 A1 Jul. 27, 2023

Related U.S. Application Data

(60) Provisional application No. 63/041,421, filed on Jun. 19, 2020, provisional application No. 63/041,450, filed on Jun. 19, 2020, provisional application No. 63/152,811, filed on Feb. 23, 2021.

(51) Int. Cl.

| | |
|---|---|
| *C07K 16/00* | (2006.01) |
| *A61K 40/11* | (2025.01) |
| *A61K 40/31* | (2025.01) |
| *A61K 40/32* | (2025.01) |
| *A61K 40/33* | (2025.01) |
| *A61K 40/42* | (2025.01) |
| *C07K 14/705* | (2006.01) |
| *C07K 16/28* | (2006.01) |
| *C07K 16/30* | (2006.01) |
| *G01N 33/575* | (2026.01) |

(52) U.S. Cl.
CPC .......... *C07K 16/2896* (2013.01); *A61K 40/11* (2025.01); *A61K 40/31* (2025.01); *A61K 40/32* (2025.01); *A61K 40/33* (2025.01); *A61K 40/42* (2025.01); *A61K 40/4202* (2025.01); *C07K 14/7051* (2013.01); *C07K 16/30* (2013.01); *G01N 33/5759* (2026.01); *C07K 2317/24* (2013.01); *C07K 2317/31* (2013.01); *C07K 2317/622* (2013.01); *C07K 2319/00* (2013.01); *G01N 2333/70596* (2013.01)

(58) Field of Classification Search
CPC ............ C07K 16/2896; C07K 14/7051; C07K 16/30; C07K 2317/24; C07K 2317/31; C07K 2317/622; C07K 2319/00; A61K 40/11; A61K 40/31; G01N 33/5759
See application file for complete search history.

(56) References Cited

U.S. PATENT DOCUMENTS

| | | | |
|---|---|---|---|
| 10,676,528 | B2 | 6/2020 | Qin et al. |
| 2005/0129690 | A1 | 6/2005 | Bowdish et al. |
| 2009/0214428 | A1 | 8/2009 | Dimitrov et al. |
| 2011/0311558 | A1 | 12/2011 | Cao et al. |
| 2013/0336967 | A1 | 12/2013 | Kamogawa et al. |
| 2014/0044730 | A1 | 2/2014 | Yancopoulos et al. |
| 2017/0226183 | A1 | 8/2017 | Schiffer-Mannioui |
| 2018/0028650 | A1 | 2/2018 | Sagi et al. |
| 2018/0364256 | A1 | 12/2018 | Jin |

FOREIGN PATENT DOCUMENTS

| | | |
|---|---|---|
| CN | 107619443 | 1/2018 |
| CN | 109748964 | 5/2019 |
| EP | 2210939 | 7/2010 |

(Continued)

OTHER PUBLICATIONS

Burke, R. et al., "Identification of BST2 as a Potential Therapeutic Target in B Cell Malignancies Including Chronic Lymphocytic Leukemia and Mantle Cell Lymphoma.", *Clinical Lymphoma, Myeloma & Leukemia*, 11, Supplement 2:S192-S3, 2011.
Cai, D. et al., "Up-regualtion of bone marrow stromal protein 2 (BST2) in breast cancer with bone metastasis", *BMC Cancer*, 9:102, 2009.
Cao, W. et al., "Regulation of TLR7/9 responses in plasmacytoid dendritic cells by BST2 and ILT7 receptor interaction", *J Exp Med.*, Jul. 6, 2009; 206(7): 1603-1614. doi: 10.1084/jem.20090547.
Cao, W. et al., "Signaling and ligand interaction of ILT7: receptor-mediated regulatory mechanisms for plasmacytoid dendritic cells", *Immunol Rev.*, Mar. 2010; 234(1): 163-176. doi: 10.111/j.0105-2896.2009.00867.x.

(Continued)

*Primary Examiner* — Lei Yao
(74) *Attorney, Agent, or Firm* — Norton Rose Fulbright US LLP

(57) ABSTRACT
Embodiments of the disclosure include methods and compositions directed to targeting of cells that express the long form of Bone marrow stromal cell antigen 2 (BST2) protein, including cancer cells that express the long isoform of BST2. In particular embodiments, monoclonal antibodies or functionally active fragments thereof are utilized to target cells that express the long isoform of BST2. The monoclonal antibodies or functionally active fragments thereof may be utilized by themselves or as part of other entities, such as cells or engineered antigen receptors. The disclosure includes methods of treatment, prevention, and/or diagnosis using the encompassed antibodies or functional fragments thereof.

11 Claims, 33 Drawing Sheets

Specification includes a Sequence Listing.

(56) References Cited

FOREIGN PATENT DOCUMENTS

| JP | 2004173767 | 4/2009 |
| JP | 2017-513818 | 6/2017 |
| WO | WO 2008/036688 | 3/2008 |
| WO | WO 2009/051201 | 4/2009 |
| WO | WO 2010/065536 | 6/2010 |
| WO | WO 2015/083791 | 6/2015 |
| WO | WO 2016/179319 | 11/2016 |
| WO | WO 2019/165421 | 8/2019 |

OTHER PUBLICATIONS

Cocka, LJ. et al., "Identification of alternatively translated Tehterin isoforms with differing antiviral and signaling activities", PLoS pathogens, 8(9): e1002931, 2012.

Harada, T., et al., " Targeted therapy for HM1.24 (CD317) on multiple myeloma cells.", *BioMed Research International*, 2014: 965384.

International Search Report and Written Opinion issued in corresponding PCT Application No. PCT/US2021/037920, mailed Oct. 4, 2021.

Kampf, C. et al., "Production of tissue microarrays, immunohistochemistry staining and digitalization within the human protein atlas.", *Journal of Visualized Experiments: JoVE*, 63, e3620, 2012.

Kuang, CM et al., "BST2 confers cisplatin resistance via NF-kappaB signaling in nasopharyngeal cancer.", *Cell Death & Disease*, 8(6): e2874, 2017.

Mahauad-Fernandez WD, et al., "BST-2 promotes survival in circulation and pulmonary metastatic seeding of breast cancer cells", *Scientific Reports*, 8(1):17608, 2018.

Mukai, S. et al., "Overexpression of Transmembrane Protein BST2 is Associated with Poor Survival of Patients with Esophageal, Gastric, or Colorectal Cancer.", *Annals of Surgical Oncology*, 24(2): 594-602, 2017.

Wang, W. et al., "HMI1.24 (CD317) is a novel target against lung cancer for immunotherapy using anti-HM1.24 antibody." *Cancer Immunology, immunotherapy*, 58(6): 967-976, 2009.

Yang LL et al., "CD317 Signature in Head and Neck Cancer Indicates Poor Prognosis", *Journal of Dental Research*, 97(7): 787-794, 2018.

Extended European Search Report issued in corresponding European Application No. 21825874.7 dated Jul. 16, 2024.

Schliemann et al. "In vivo biotinylation of the vasculature in B-cell lymphoma identifies BST-2 as a target for antibody-based therapy", *Blood*, vol. 115, No. 3, 736-744, 2010.

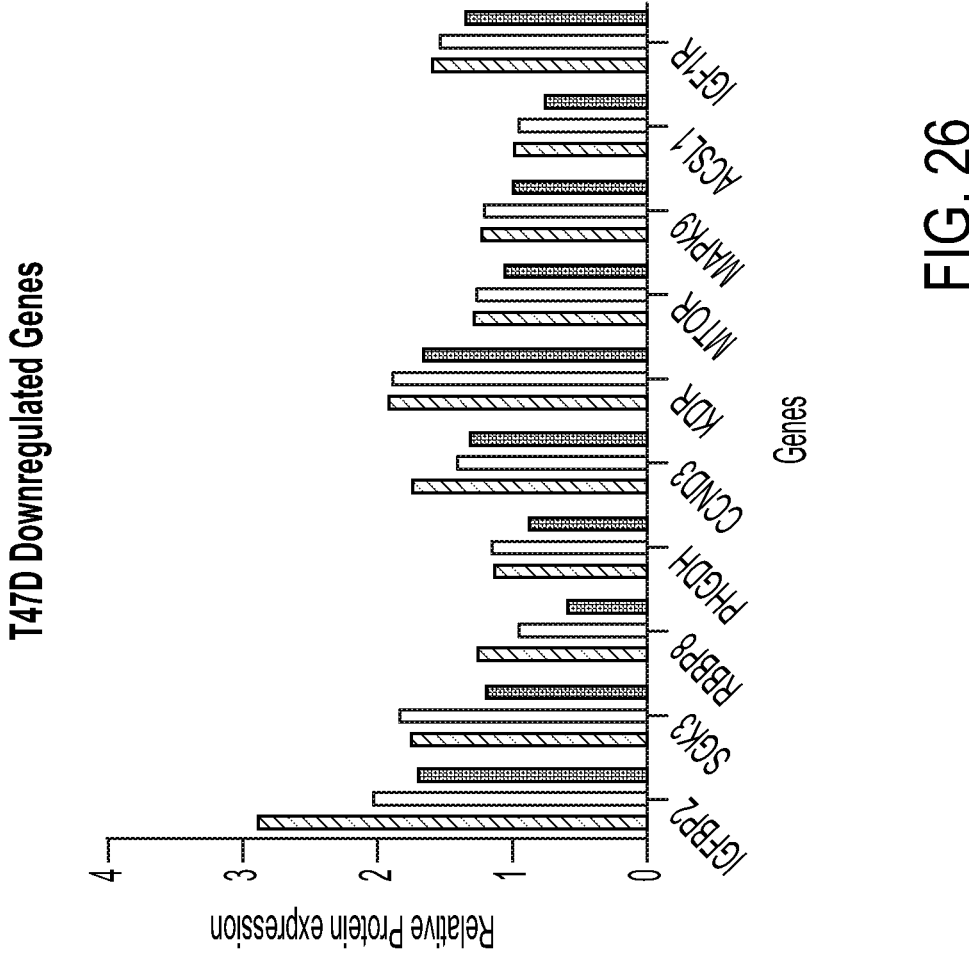
FIG. 26

Tested specimens (#72,010) Gi cores (16 breast kinds are normal breast tissue)

| | Anti-BST2 detectable rate (Antigen retrieval H1 image 1536) | | | | Anti-BST2 long isoform (MAb LA5) detectable rate (Antigen retrieval H1 image 1536) | | | |
|---|---|---|---|---|---|---|---|---|
| | Tested specimens | + | % | Range | Tested specimens | + | % | Range |
| BIDC | 50 | 17 | 34% | 1-91% | 49 | 19 | 39% | 1-76% |
| BIDC (sigmoid) | 40 | 0 | 0.0% | | 40 | 0 | 0.0% | |
| Normal breast | 8 | 0 | 0.0% | | 8 | 0 | 0.0% | |
| Breast stroma | 8 | 0 | 0.0% | | 8 | 0 | 0.0% | |
| Placenta | 1 | 0 | 0.0% | | 1 | 0 | 0.0% | |
| Placenta stroma | 1 | 0 | 0.0% | | 1 | 0 | 0.0% | |

Tested specimens (#72,010) 3 normal tissues

| | Anti-BST2 detectable rate (Antigen retrieval H1 image 1536) | | | Anti-BST2 long isoform (MAb LA5) detectable rate (Antigen retrieval H1 image 1537) | | |
|---|---|---|---|---|---|---|
| | Tested | + | % | Tested | + | % |
| Patient number | 7 | 0 | 0 | 7 | 0 | 0% |
| Tissue attachment and image (tissue) | 7 | 7 | 100% | 1 | 0 | 14.3% |

FIG. 27

ANTI-BST2 ANTIBODIES TARGETING BST2 LONG ISOFORM

This application is a national phase application under 35 U.S.C. § 371 of International Application No. PCT/US2021/037920, filed Jun. 17, 2021, which claims priority of U.S. Provisional Application No. 63/041,421, filed Jun. 19, 2020; U.S. Provisional Application No. 63/041,450 filed Jun. 19, 2020; and U.S. Provisional Application No. 63/152,811, filed Feb. 23, 2021, all of which applications are incorporated by reference herein in their entirety.

SEQUENCE LISTING

The application contains a Sequence Listing which has been filed electronically in compliance with ST.26 format and is hereby incorporated by reference in its entirety. Said Sequence Listing, created on Dec. 15, 2022 is named MDAC_P1242US_SL and is 34,089 bytes in size.

TECHNICAL FIELD

Embodiments of the disclosure include at least the fields of cell biology, immunology, molecular biology, and medicine.

BACKGROUND

Bone marrow stromal cell antigen 2 (BST2) is a raft-associated type II transmembrane protein with an unusual topology. Two research groups identified different isoforms of BST2 that are generated by post-transcriptional modification. Others have described three isoforms: long, medium and short. Different analyses showed a variable degree of expression of BST2 in many normal cells.

BST2 is expressed in a variety of tissues in the body, including dendritic cells, ovaries, adrenal glands, monocytes, NK cells, total PBMCs, lung, vagina, epididymis, and others. Importantly, BST2 is highly expressed in several tumor cells. There is overexpression of BST2 in several solid and hematological malignancies, at both the RNA and protein levels (18). In fact, most examined cancer tissues stained positive with anti-human BST2 antibodies generated against unspecified epitope of the molecule. The expression level is variable: high/moderate expression was observed in liver, breast, gastrointestinal and head and neck cancers, while low expression was noted in lymphoma and testicular cancers (17, 19).

In breast cancer, BST2 gene is upregulated in bone-metastatic breast cancer cell lines, compared to other primary and non-bone metastatic breast cancer cell lines. Moreover, BST2 serum levels were statistically significantly higher in those patients with bone metastasis. Induced expression of BST2 in a primary breast cancer cell line enhanced its proliferation and migration ability (20). Another research group identified a demethylation process at the gene level that drives the overexpression of BST2 and enhances the metastatic abilities of the primary breast cancer, including the survival in the blood stream and lung colonization (21).

In lung cancer, the upregulated expression of BST2 was observed in different lung cancer cell lines, representing small cell lung cancer, lung adenocarcinoma and non-small cell lung carcinoma. Commercially available anti-BST2 monoclonal antibodies (mAbs) did not have a direct impact on the viability or the proliferation of these cell lines but were able to show both Antibody-dependent cellular cytotoxicity (ADCC) and Complement-dependent cytotoxicity (CDC), and the use of these mAbs demonstrated significant effectiveness in reducing tumor size and growth in murine models (18).

In gastrointestinal cancers, BST2 overexpression was observed in cell lines representing esophageal, stomach and colorectal malignancies. Silencing BST2 gene was associated with significant reduction in cell growth and overexpressing BST2 protein in BST2—deficient colorectal cancer cell line significantly enhances its growth. Furthermore, the expression of BST2 was correlated with poor survival among patients with gastrointestinal cancers (22).

In head and neck cancers, many gene expression databases indicated overexpression of BST2, and clinical data from patients with head and neck squamous cell carcinoma and high BST2 expression showed poor survival, when compared to patients with low BST2 expression (23). Moreover, silencing BST2 rendered nasopharyngeal cancer cells sensitive to cisplatin and halted its resistance to platinum therapy (24).

Lastly, in hematological malignancies, BST2 (or HM1.24) was first described as a membrane glycoprotein in multiple myeloma and was thought to be selectively expressed on terminally differentiated B cells. More than 80,000 molecules of BST2 could be identified on the surface of a single myeloma cell (2). Although the functional role of BST2 in multiple myeloma has not yet been identified, the overexpression of this surface protein and the need for new therapeutic approaches to treat this malignancy made BST2 a potential therapeutic target, using monoclonal antibodies. Initial preclinical studies and mouse models demonstrated the effectiveness of these anti-BST2 mAbs in limiting the tumor burden, mainly through ADCC. Consequently, a phase I/II clinical study was initiated to test the safety and effectiveness of these mAbs as a therapeutic agent in patients with relapsed or refractory multiple myeloma. The response rate was relatively low, and the study was terminated, despite the manageable adverse events (25). The expression of BST2 on the surface of other malignant blood cells, including mature B lymphocytes, has been evaluated as well. Using patients' samples, BST2 was demonstrated as expressed in chronic lymphocytic leukemia (CLL) and mantle cell lymphoma (MCL), making BST2 a potential therapeutic target in other subclasses of malignancies (26).

The present disclosure provides solutions to long-felt needs in the art of cancer therapy, prevention, and diagnosis.

BRIEF SUMMARY

Embodiments of the disclosure include methods and compositions in which BST2 is used as a target, including for therapeutic approaches to treat different malignant diseases and/or for detection methods to identify the presence of BST2-expressing cells. In particular embodiments, the present disclosure is directed to compositions and methods for treatment, prevention, or diagnosis of cancer, wherein the cancer comprises cells that express BST2, including the long isoform of BST2. In particular embodiments, the compositions and methods are directed to one or more agents that target the long isoform of BST2. In particular embodiments, the agent is an antibody or a functionally active fragment thereof. The antibody or functionally active fragment thereof may bind to all or part of SEQ ID NO:1 (EVERLRRENQVLSVRIADKKYYPS), SEQ ID NO:2 (RENQVLSVRIADKKYYPS), or SEQ ID NO:4 (RENQVLSVRI), or the antibody may bind to a sequence that is at least 80%, 85%, 90%, 92%, 95%, 97%, 98%, 99% or higher in identity to SEQ ID NO:1, SEQ ID NO:2, or SEQ ID NO:4. The antibody may be of any kind but in specific embodiments the antibody is a monoclonal antibody or a single chain variable fragment thereof.

Embodiments of the disclosure encompass differential targeting of tumor cells vs. normal cells in any cancer in which BST2 is expressed in long isoform. In particular embodiments, cancer cells expressing the long isoform of BST2 are targeted over any other cells in the body that lack expression of the long isoform of BST2. Specific embodiments utilize one or more particular antibodies or functional fragments thereof to specifically bind the long isoform of BST2.

The disclosure comprises the generation of monoclonal antibodies that specifically recognize the BST2 long isoform, which in certain embodiments is differentially expressed in tumor cells and tumor tissues, such as compared to non-cancerous cells. The antibodies encompassed herein may be utilized to detect cancer or to characterize a cancer, including its type, stage, and/or whether or not it has metastasized. The antibodies encompassed herein serve as a therapy for different tumor types in which BST2 long isoform is expressed, in specific embodiments. They can be used as naked antibodies, in engineered antigen receptors (such as CAR-T cells or CAR-NK cells), as bispecific antibodies (including for engagers of any kind), as antibody drug conjugates, or radioisotope conjugates and so forth. In certain embodiments, the mode of action for the antibodies could include but is not limited to complement-dependent cytotoxicity (CDC), Antibody-dependent cellular cytotoxicity (ADCC), apoptosis, etc.

Embodiments of the disclosure encompass compositions comprising an antibody or a functionally active fragment thereof that binds part or all of SEQ ID NO:1, SEQ ID NO:2, or SEQ ID NO:4. Aspects of the disclosure include SEQ ID NO:1, SEQ ID NO:2, or SEQ ID NO:4 that comprise an epitope for binding of the antibody. The antibody may be a monoclonal antibody, such as LA1, LA5, LA8, LA15, BM2, BM5, BM7, BM8, or a mixture thereof. The functionally active fragment thereof may be selected from the group consisting of a single-chain variable fragment (scFv), Fv, Fab, and F(ab')2, and any antibody may be humanized.

Embodiments of the disclosure encompass methods and compositions for detection of BST2 from any tissue, but in specific embodiments the tissue comprises cancerous cells that express BST2. In specific cases, the cancer cells express the long isoform of BST2. In particular embodiments, the antibodies of the present disclosure that bind the long isoform of BST2 are able to distinguish cancer cells from cells that are not cancer cells but that still express other isoforms of BST2. The detection of BST2-expressing cancer cells may be related to a primary cancer or a metastatic cancer. Thus, in specific embodiments antibodies that bind BST2 are utilized to determine if there is metastatic cancer in an individual suspected of having or at risk for having metastatic cancer. In specific cases, the antibodies are utilized to detect primary breast cancer or infiltration of malignant breast ductal carcinoma (including early infiltration of malignant breast ductal carcinoma), although in other specific cases the antibodies are utilized to detect head and neck, liver, ovarian, colorectal, or other types of cancers.

Embodiments of the disclosure include measuring BST2 with one or more antibodies encompassed herein in tissue comprising BST2-expressing cancer cells or in tissue suspected of comprising BST2-expressing cancer cells.

In some embodiments, the composition comprises an engineered antigen receptor and the receptor comprises a scFv of the BST2 antibody. Examples of engineered antigen receptors include a chimeric antigen receptor or a T cell receptor, including expressed on a cell such as an immune cell including a T cell, NK cell, or NKT cell.

Any compositions encompassed herein may be formulated in a pharmaceutically acceptable carrier.

In certain embodiments, there are cells expressing any composition encompassed herein, including any pharmaceutical compositions comprising the composition of the disclosure and formulated in a pharmaceutically acceptable carrier.

In particular embodiments, there is a method of treating or preventing cancer in an individual, comprising the step of administering to the individual an effective amount of a composition of the disclosure, wherein the cancer cells of the cancer express the long isoform of BST2. The cancer may be of any kind that expresses the long isoform of BST2, such cancer of the breast, brain, lung, liver, colon, kidney, stomach, pancreas, prostate, blood, skin, spleen, gall bladder, thyroid, testes, ovary, endometrium, cervix, head and neck, or bone, merely as examples. The composition may be administered to the individual once or multiple times. When the composition is administered to the individual multiple times, the duration between administrations may be 1-24 hours, 1-7 days, 1-4 weeks, 1-12 months, or longer. The composition may be administered to the individual intradermally, intramuscularly, intraperitoneally, intravenously, subcutaneously, intranasally, epidurally, or orally. The composition may be administered systemically or locally, such as intratumorally. In some cases, the individual is administered an additional cancer therapy, such comprises surgery, radiation, chemotherapy, hormone therapy, or a combination thereof.

In embodiments of the disclosure, there are methods of assessing whether an individual has cancer or characterizing the cancer in an individual, comprising the step of subjecting one or more samples from an individual suspected of having cancer or known to have cancer, respectively, with an effective amount of any composition of the disclosure. The cancer may be of any kind that expresses the long isoform of BST2, such cancer of the breast, brain, lung, liver, colon, kidney, stomach, pancreas, prostate, blood, skin, spleen, gall bladder, thyroid, testes, ovary, endometrium, cervix, head and neck, or bone, merely as examples. In such cases, the sample may comprise tissue, blood, plasma, serum, biopsy, hair, cheek scrapings, nipple aspirate, saliva, or a combination thereof.

In certain embodiments, there is a method of treating an individual with cancer, wherein when the individual is determined to have cancer based on detection of cancer in a sample with any composition encompassed herein, the individual is administered an effective amount of cancer therapy, including any composition encompassed herein and/or surgery, radiation, chemotherapy, hormone therapy, drug therapy, or a combination thereof.

In some embodiments, there is a kit comprising any composition encompassed herein, and the compositions may be housed in a suitable container(s).

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

It is specifically contemplated that any limitation discussed with respect to one embodiment of the invention may apply to any other embodiment of the disclosure. Furthermore, any composition of the disclosure may be used in any method of the disclosure, and any method of the disclosure may be used to produce or to utilize any composition of the disclosure. Aspects of an embodiment set forth in the Examples are also embodiments that may be implemented in the context of embodiments discussed elsewhere in a different Example or elsewhere in the application, such as in the Brief Summary, Brief Description of the Drawings, Detailed Description, and Claims.

BRIEF DESCRIPTION OF THE DRAWINGS

For a more complete understanding of the present disclosure, reference is now made to the following descriptions taken in conjunction with the accompanying drawings.

FIGS. 4A, 4B, and 4C, respectively) after 5 injections (post 5) and after 8 injections (post 8) having as reference the pre-immune serum sample. Plates were coated with BST2 peptide alone.

Figure 7:
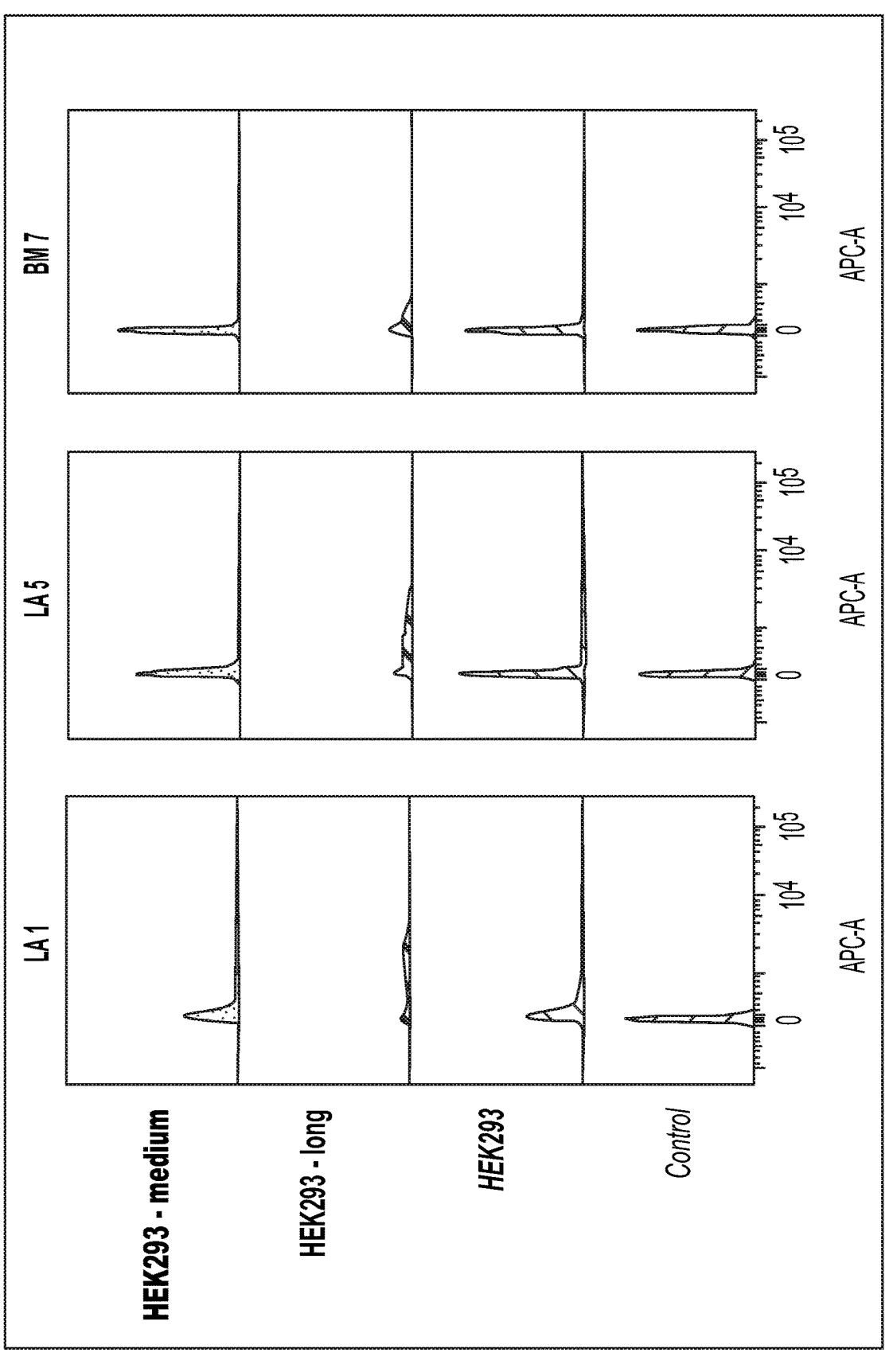

FIG. 7. Flow cytometry staining of the HEK293 cell lines. Using supernatants collected from three selected clones (LA1, LA5, and BM7), data showed maximum mean fluorescence staining of HEK293—long transfectant and minimum staining of the other transfectants. For the control, secondary antibody (Donkey anti-mouse Allophycocyanin (APC) conjugated) was used only.

Figure 8:
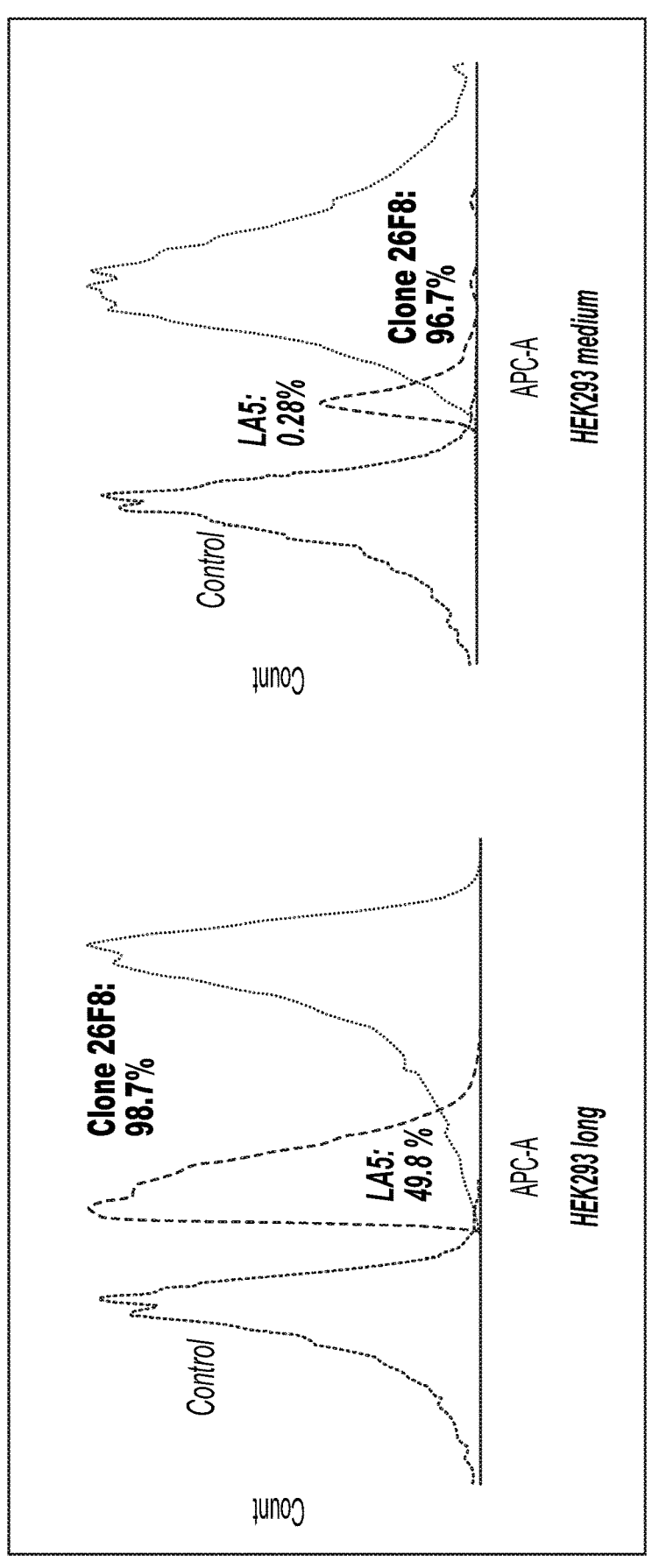

FIG. 8. Comparison between Clones LA5 and Clone26F8. Flow cytometry staining of HEK293 long and HEK293 medium transfectants, using 1 ug/ml of clones (LA5) and anti-BST2 (26F8) monoclonal antibodies. This figure demonstrates the specificity of the generated antibody (LA5) to selectively bind to the long isoform. In contrast, 26F8 mAb recognized both isoforms. APC conjugated secondary antibody alone was used as a control.

Figure 9:
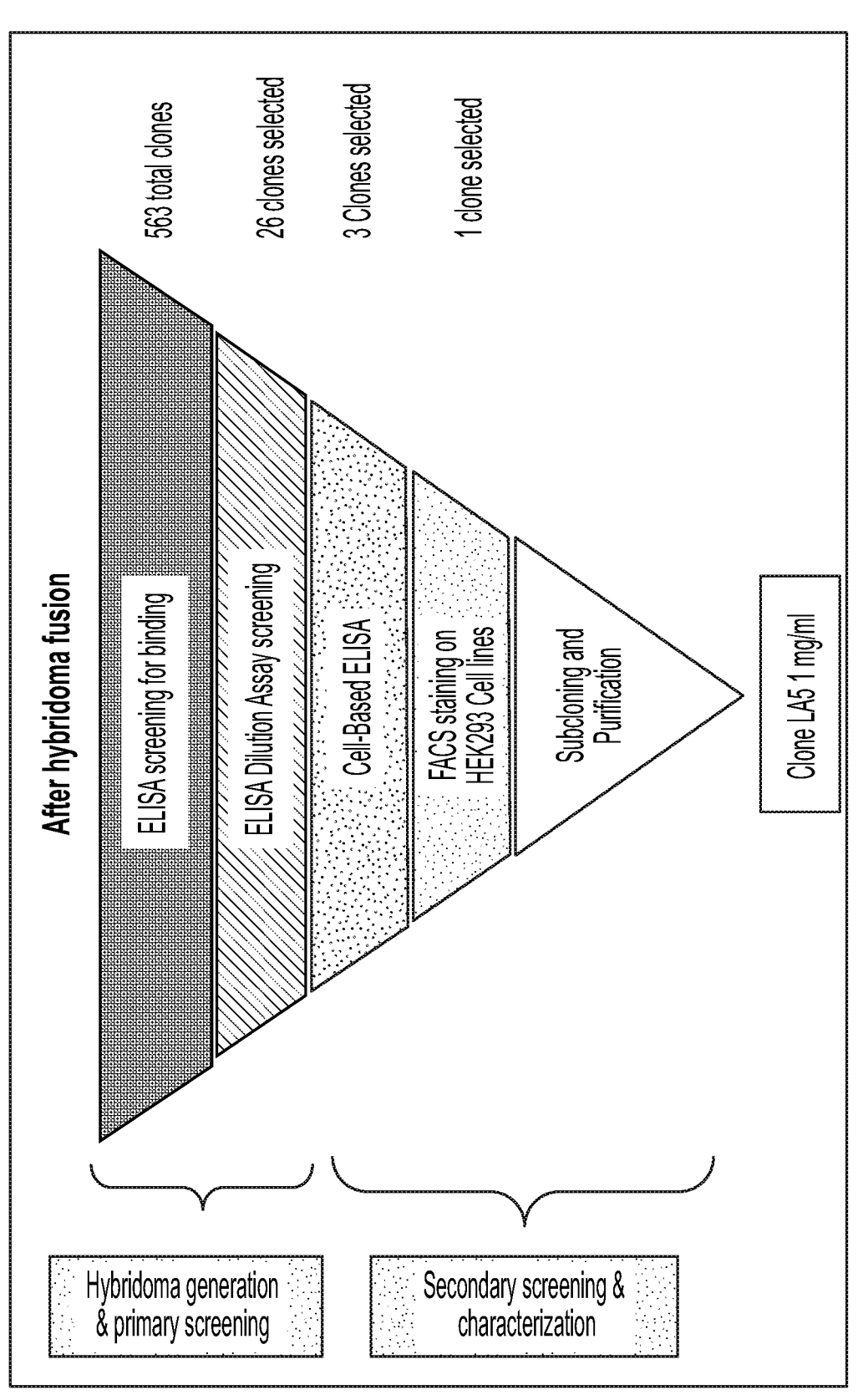

FIG. 9. Anti-BST2-long mAb Screening Funnel. The diagram illustrates the various screening steps performed after the generation of the hybridomas, up to the selection of the monoclonal antibody candidate, clone LA5, purified and concentrated.

Figure 10:
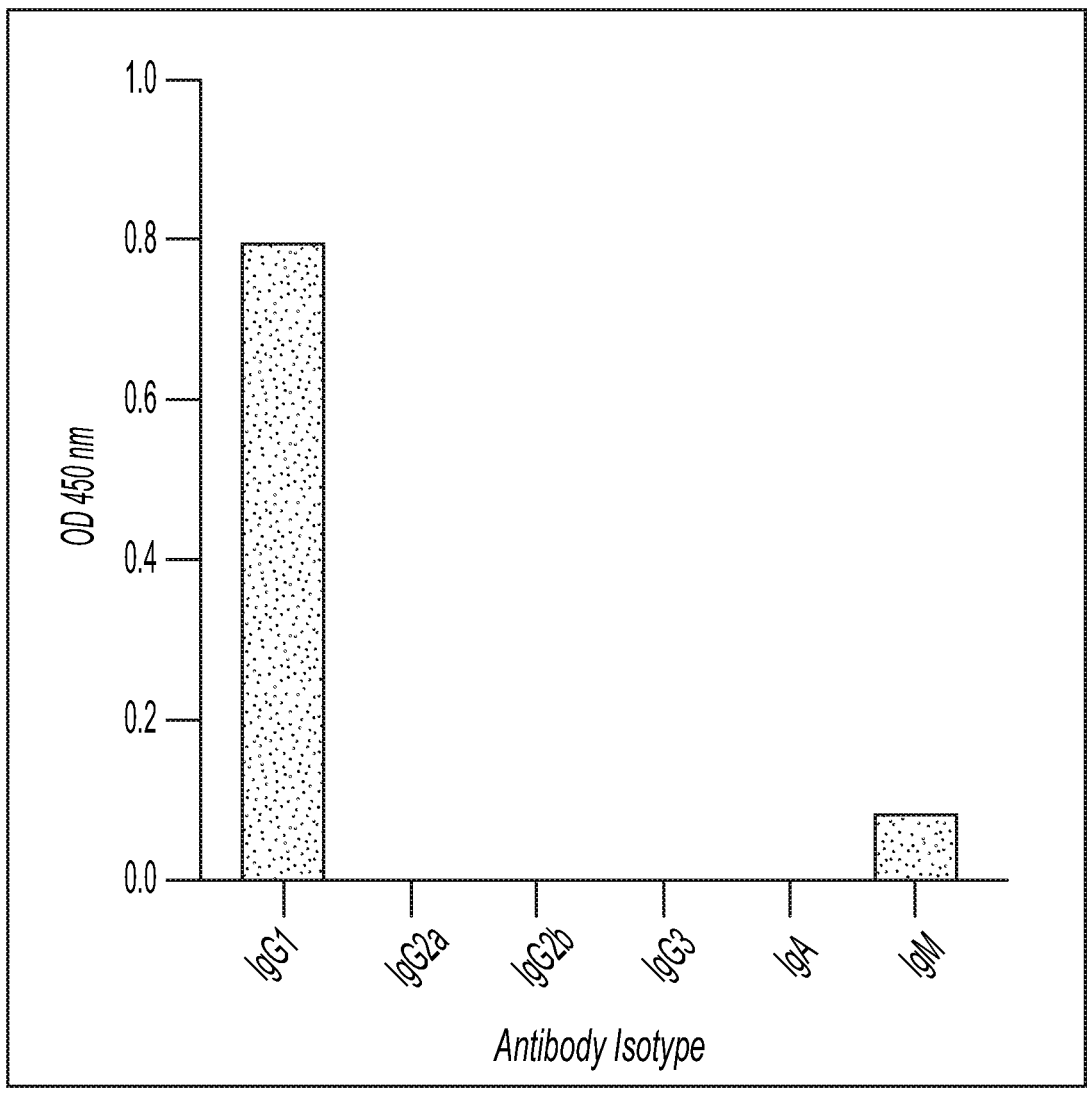

FIG. 10. Isotype ELISA Test. Isotype of clone LA5 was determined by an ELISA kit, following manufacturer recommendations.

Figure 11:
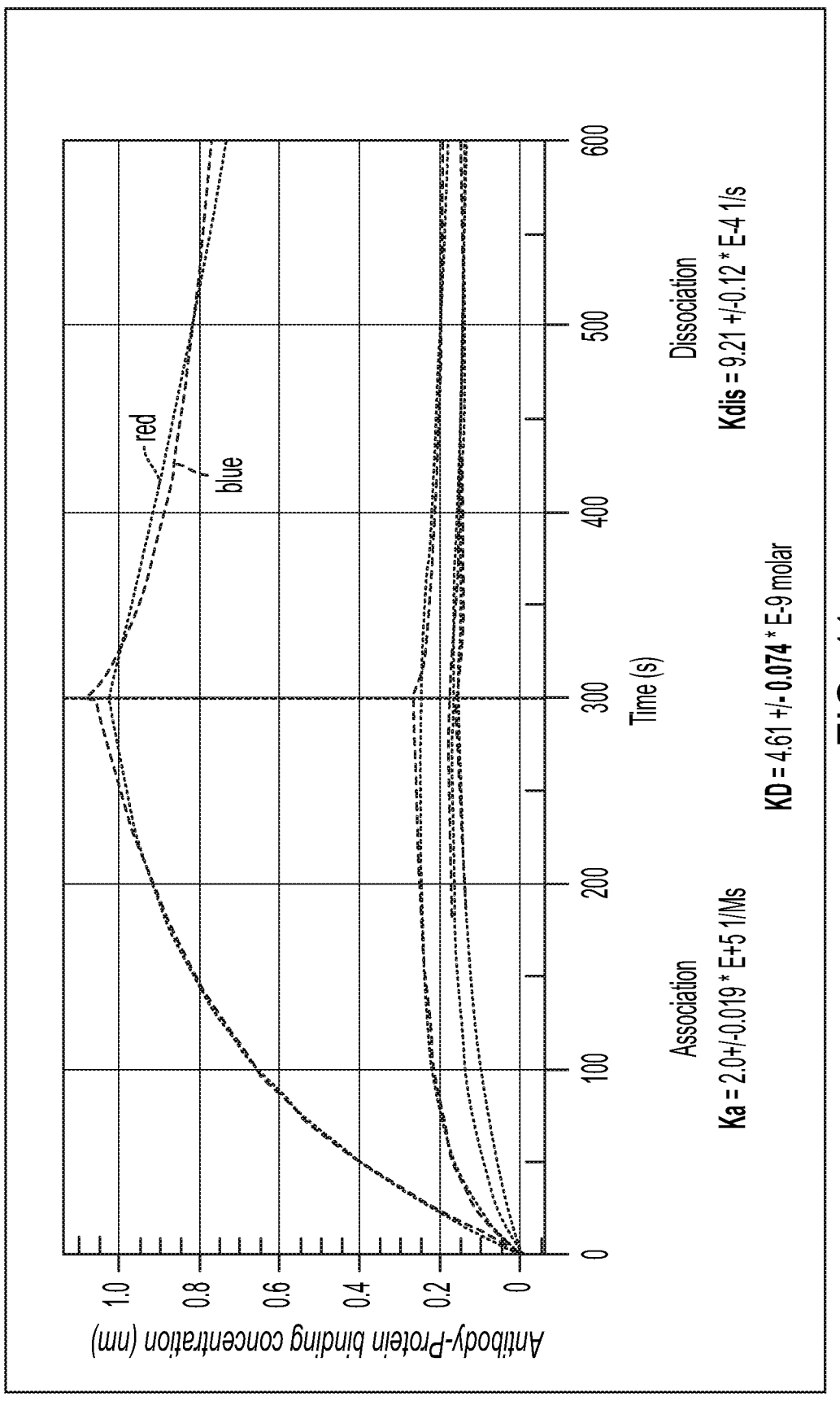

FIG. 11. Determination of Ka, Kd and KD for LA5-antigen binding. The binding kinetics of anti-BST2-long clone LA5 (5 ug/ml) and BST2 protein at various concentrations (blue lines). The 1:1 fitting model is shown (red line).

Figure 12:
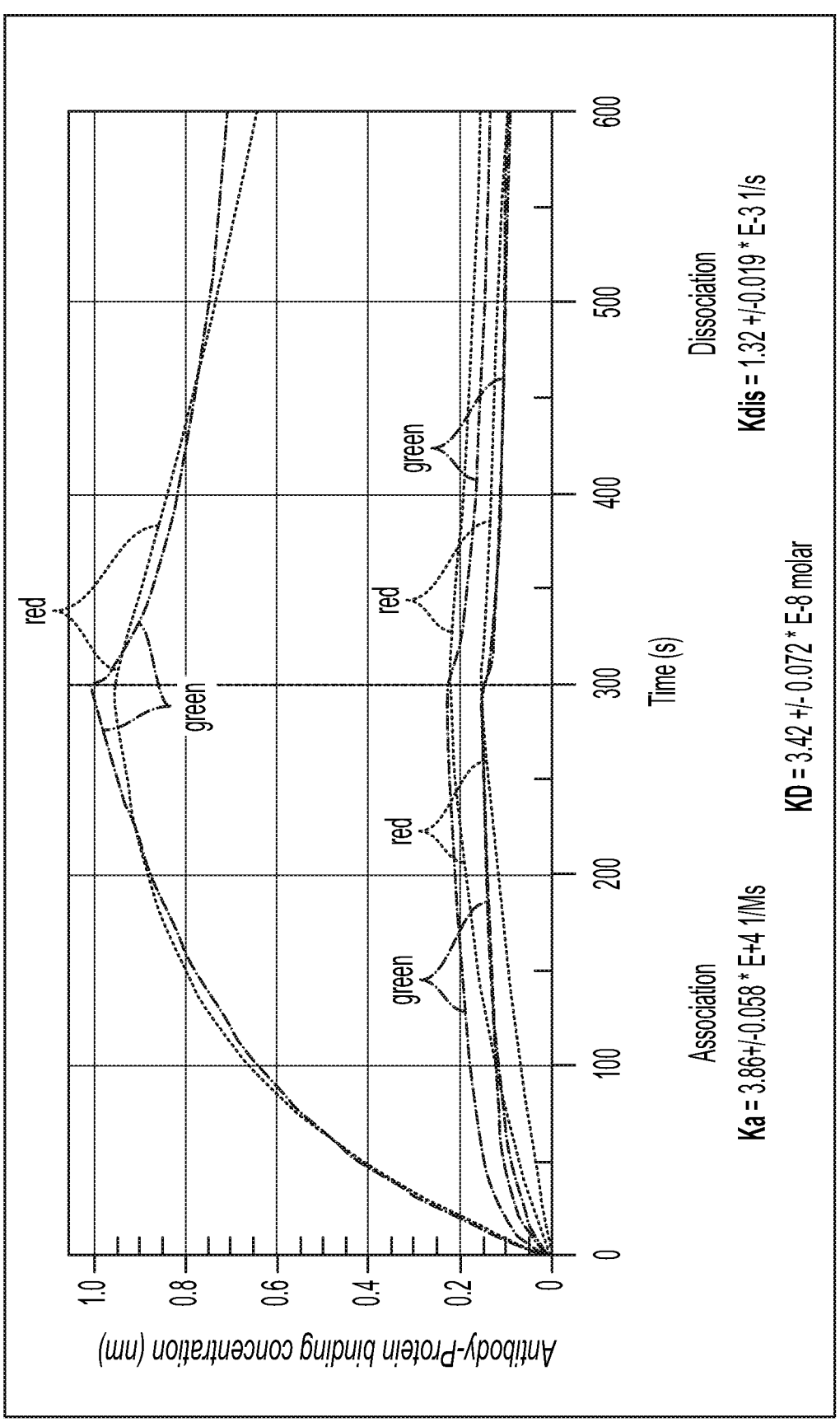

FIG. 12. Determination of Ka, Kd and KD for 26F8-antigen binding. The binding kinetics of anti-BST2 Clone 26F8 (5 ug/ml) and BST2 protein at various concentrations (green lines). The 1:1 fitting model is shown (red lines).

Figure 13:
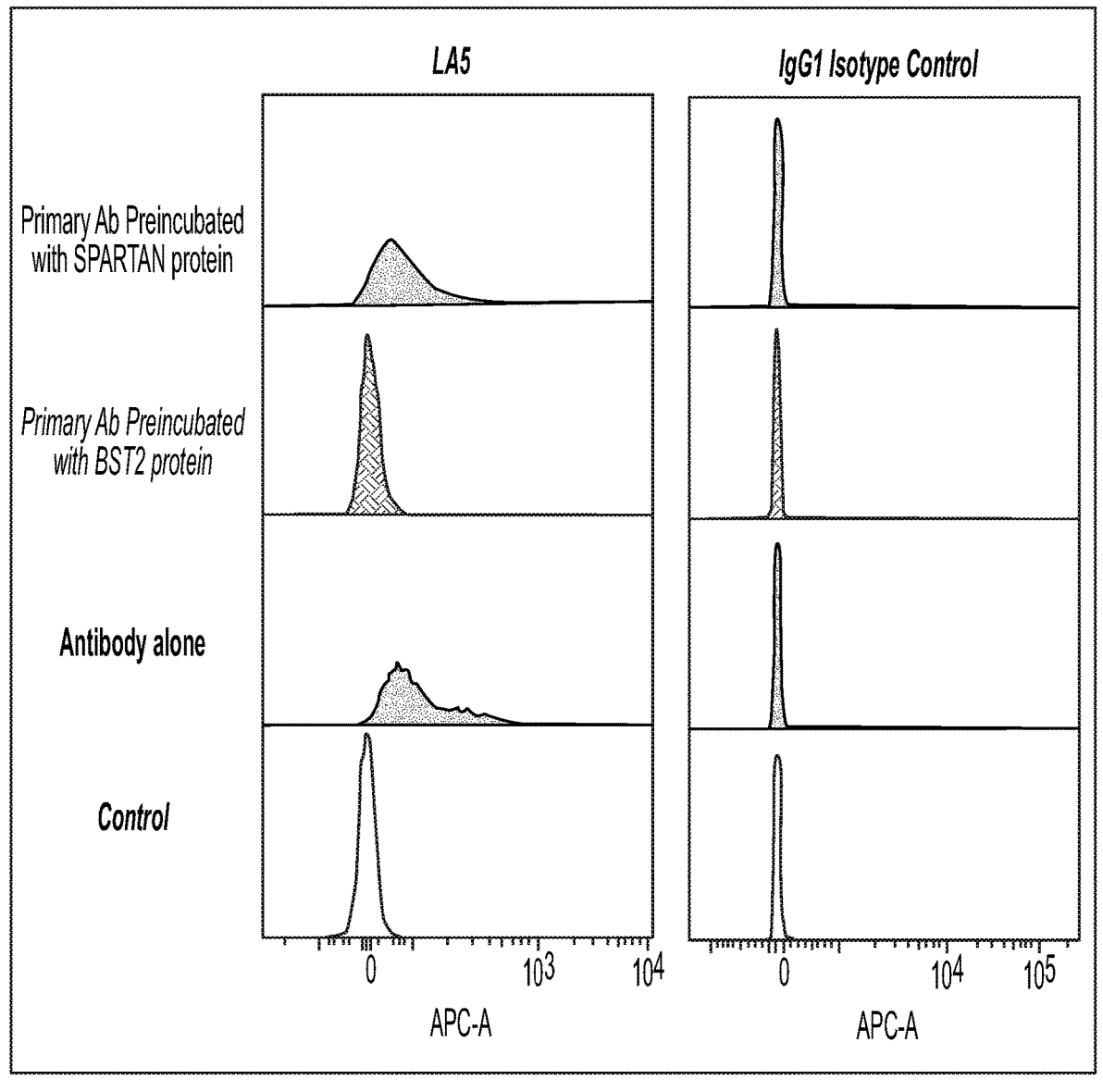

FIG. 13. LA5 mAb specificity. Flowcytometry staining of MM1 Cell line, using the generated monoclonal antibodies LA5 and IgG1 isotype control. The percentage of cell staining was reduced from 85.2% to 5.01% when LA5 mAb was preincubated with BST2 protein (5 ug/ml), while preincubation with Spartan irrelevant protein did not lead to this reduction. In both columns, secondary antibody (Donkey anti-mouse Allophycocyanin (APC) conjugated) was used alone as a control.

Figure 14:
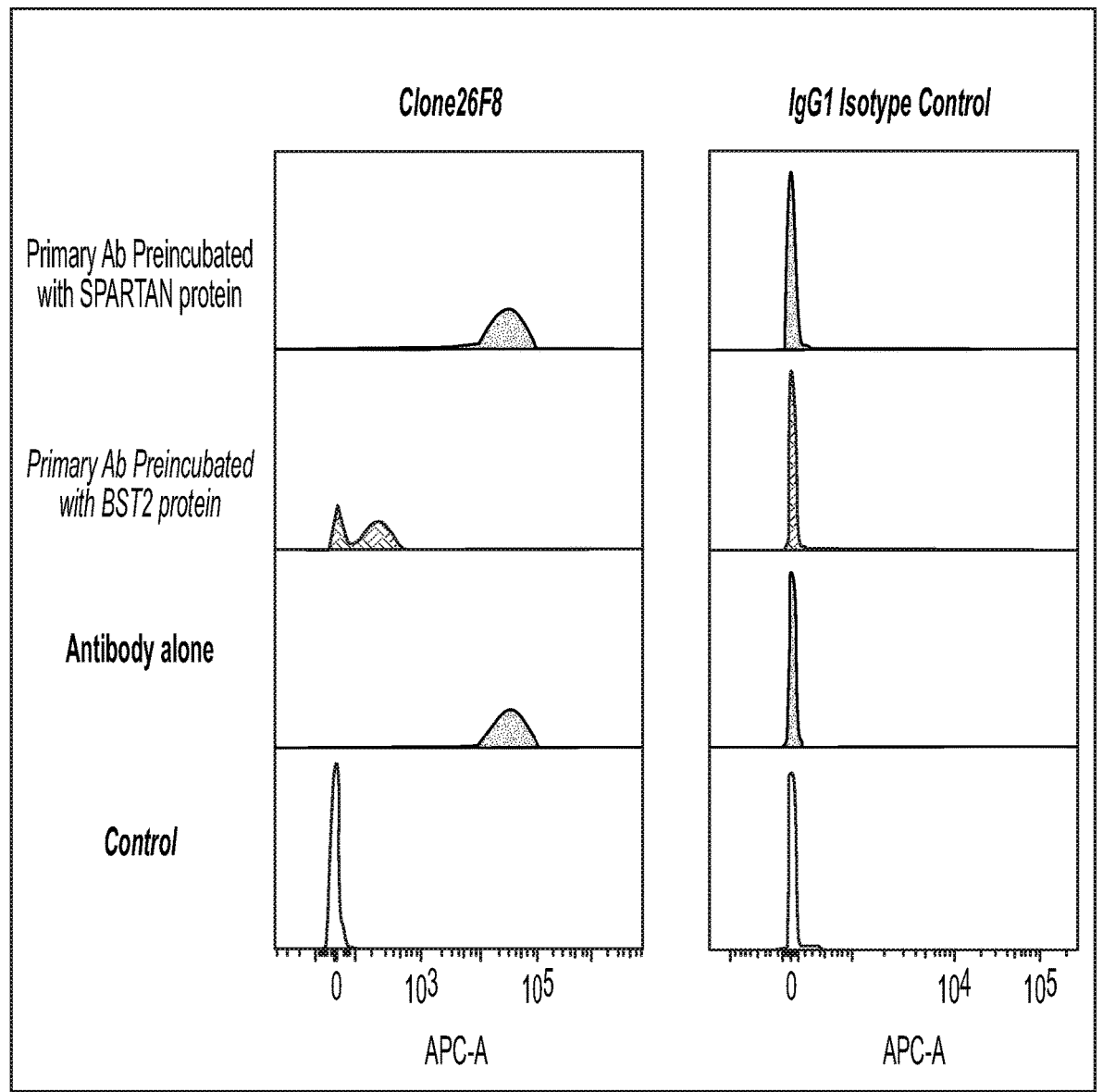

FIG. 14. 26F8 mAb specificity. Flowcytometry staining of MM1 Cell line using anti-BST2 (Clone 26F8) mAb and IgG1 isotype control. The percentage of cell staining was reduced from 98.2% to 2.6% when the 26F8 mAb was preincubated with BST2 protein, while preincubation with Spartan irrelevant protein was not associated with a reduction. In both columns, secondary antibody (Donkey anti-mouse Allophycocyanin (APC) conjugated) was used alone as a control.

Figure 15:
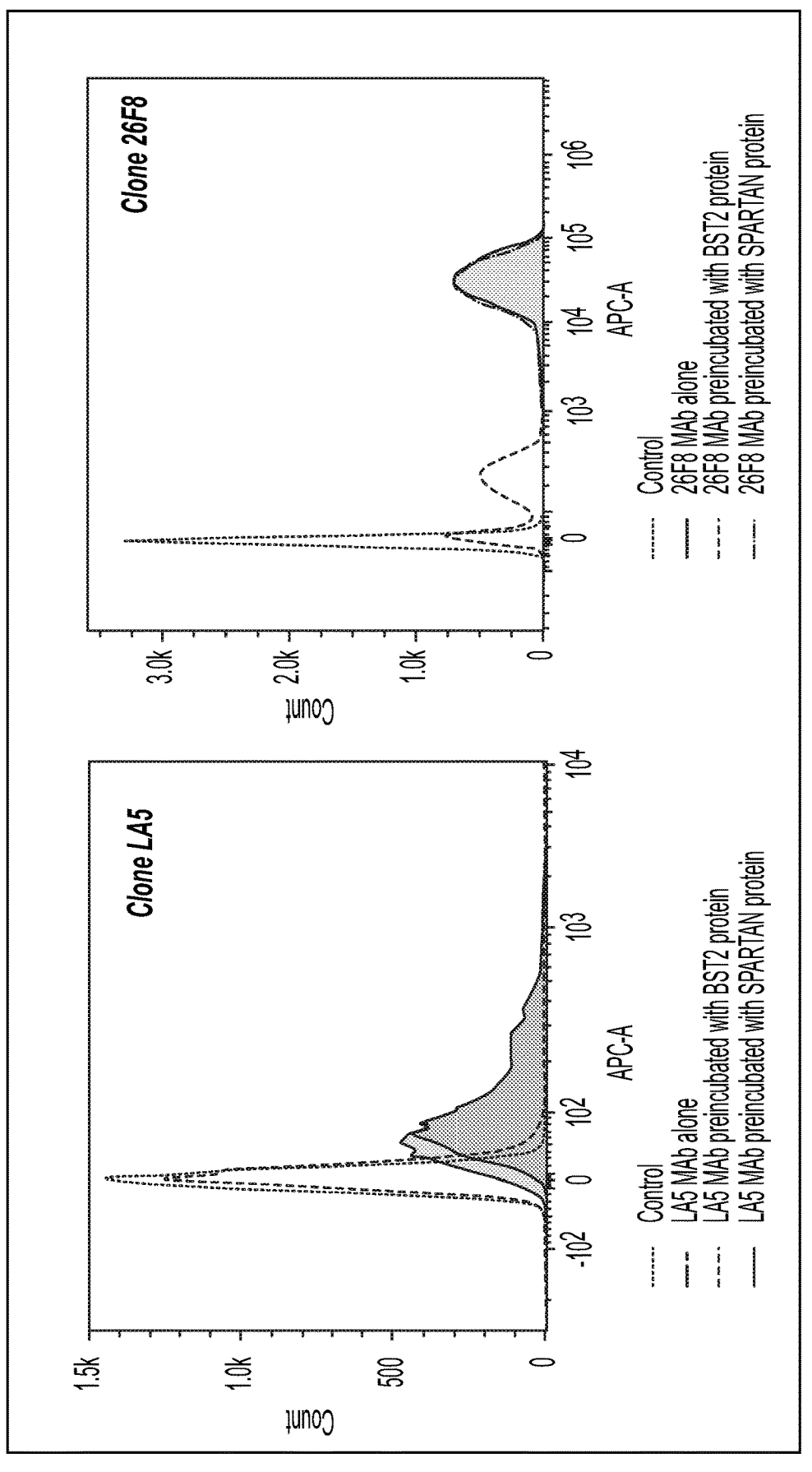

FIG. 15. Specificity comparison of the LA5 and 26F8. Flow cytometry staining of MM1 Cell line using of the generated anti-BST2-long (Clone LA5) mAb and anti-BST2 (Clone 26F8) mAb, preincubated with recombinant BST2 protein or irrelevant protein and using secondary antibody APC conjugated as control. This figure demonstrates the comparability between these two mAbs, in term of specificity.

Figures 16A, 16B, 16C:
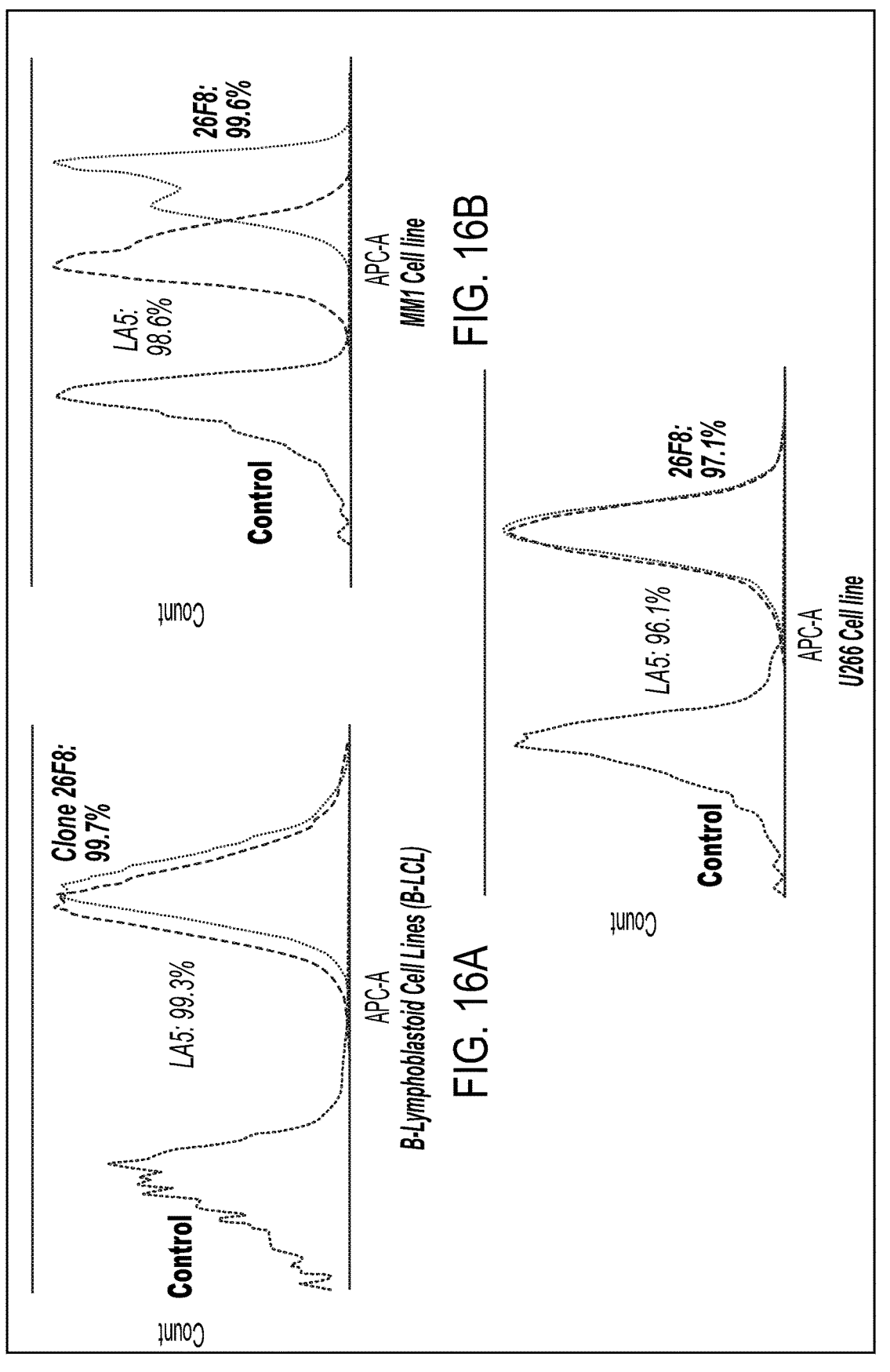

FIGS. 16A-16C. Flow cytometry staining of examples of B cell lines. FACS staining of three cell lines, representing normal (but still transformed) and malignant plasma cells, using the generated monoclonal antibody against the long isoform of BST2 (LA5), and anti-BST2 (26F8), at a concentration of 1 ug/ml. Secondary antibody alone APC-conjugated, was used as a control. FIG. 16A is the B-LCL cell line (normal transformed), FIG. 16B is the MM1 cell line, and FIG. 16C is the U266 cell line.

Figures 17A, 17B, 17C, 17D:
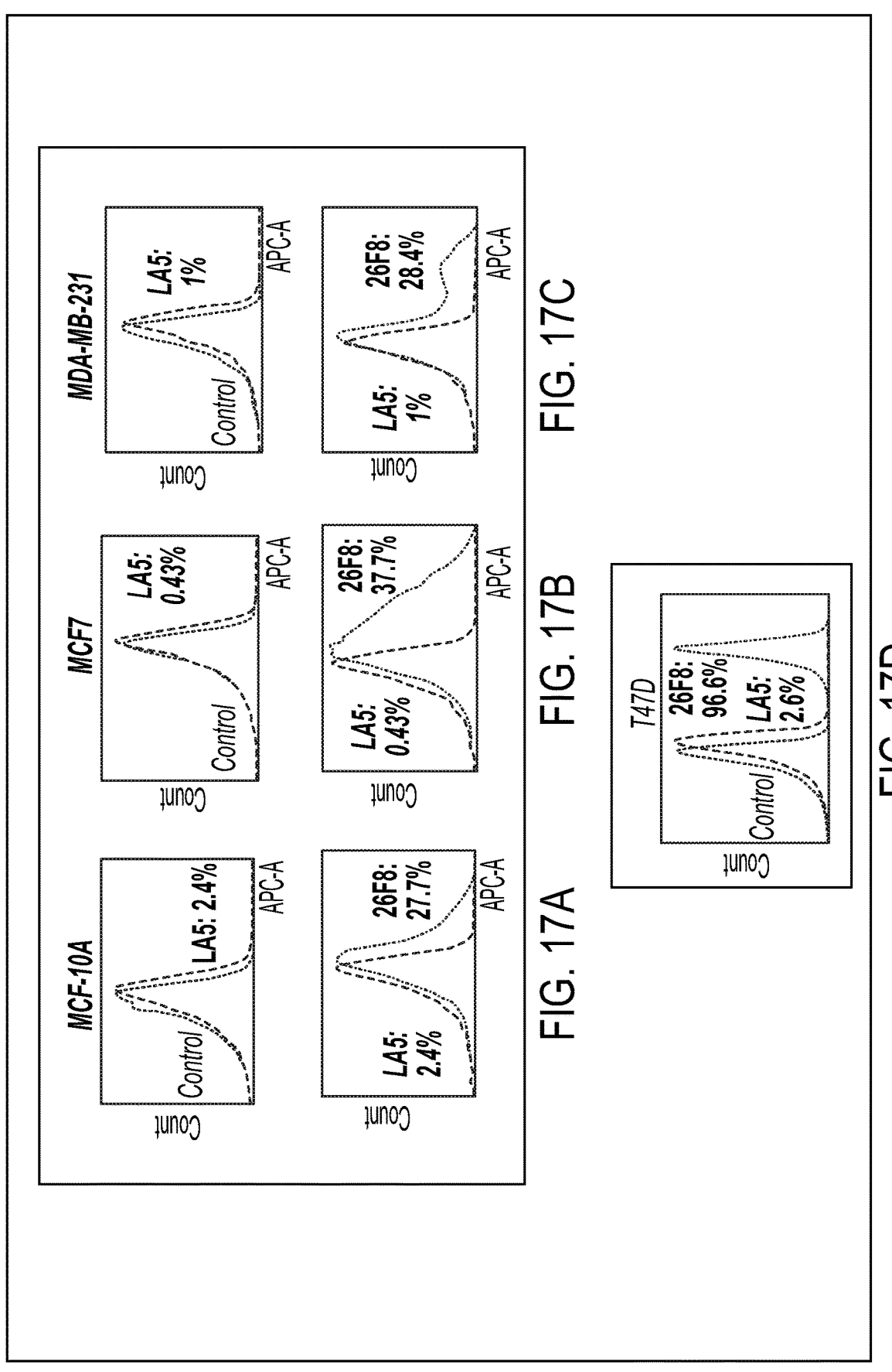

FIGS. 17A-17D. Flow cytometry staining of examples of breast tissue cell lines. FACS staining of four cell lines, representing normal and malignant breast tissue cells, using the mAb against the long isoform of BST2 (clone LA5) and the anti-BST2 (clone 26F8). Secondary antibody APC conjugated were used alone as a control. FIG. 17A is MCF-10A cell line, FIG. 17B is MCF7 cell line, FIG. 17C is MDA-MB-231 cell line, and FIG. 17D is T47D cell line.

Figure 18A:
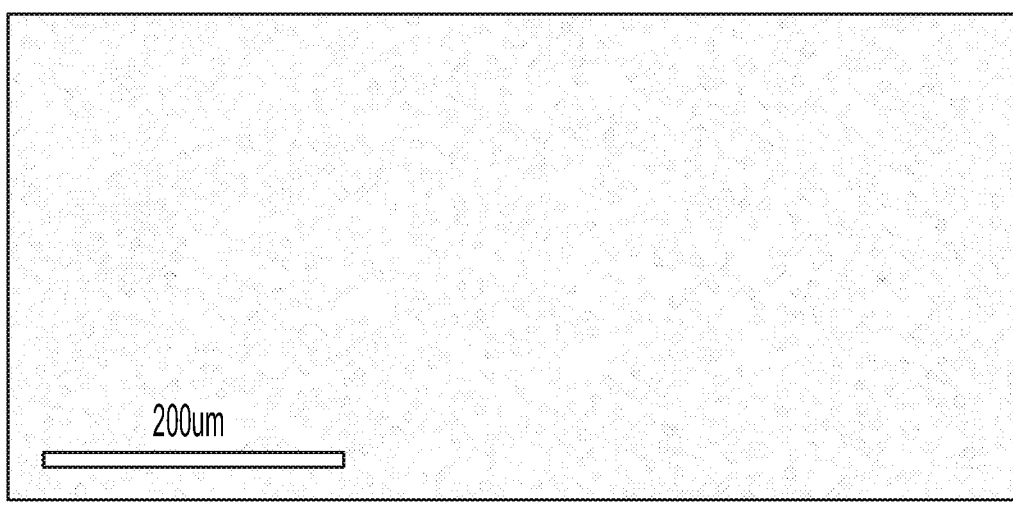
Figure 18B:
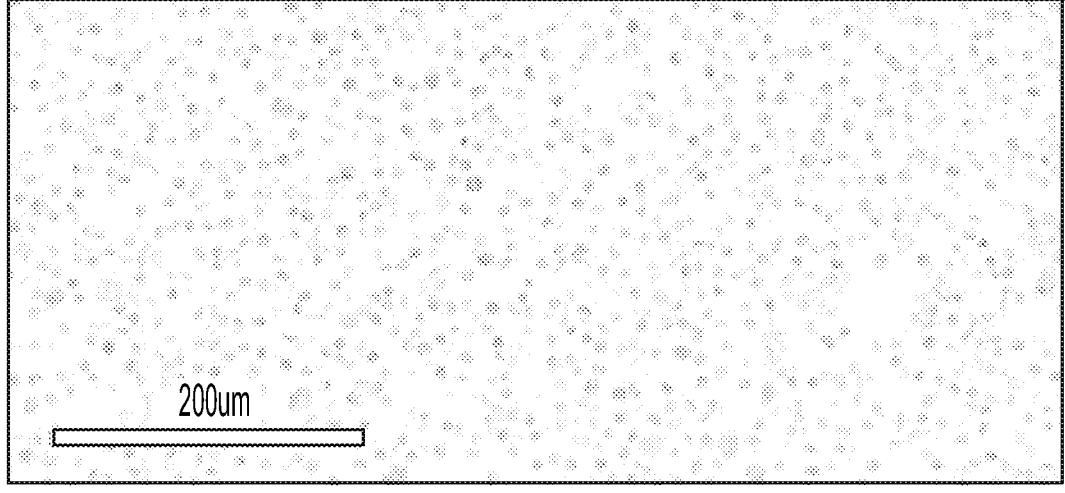
Figure 18C:
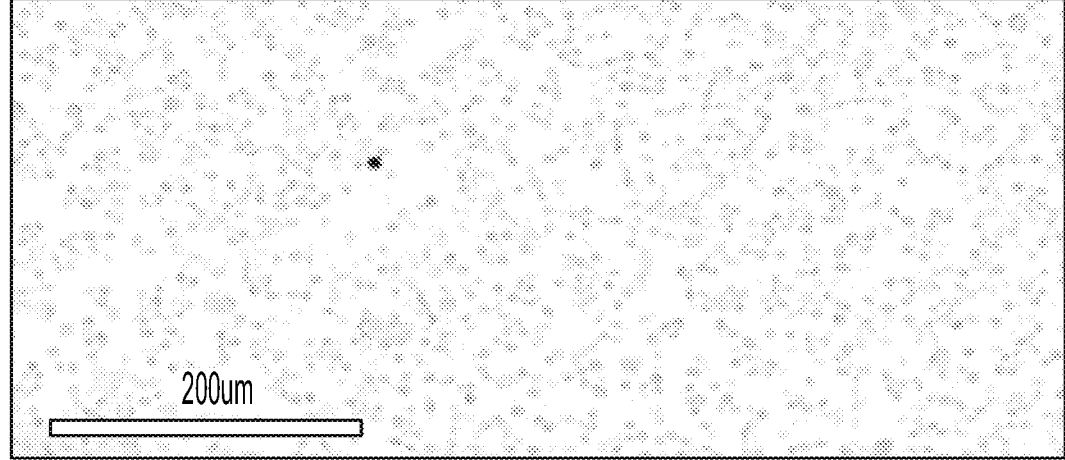

FIGS. 18A-18C. Immunohistochemistry staining of HEK293 cell lines. Staining pattern of the transduced HEK-293 cell lines, using anti-BST2-long (clone LA5) and anti-BST2 (clone 26F8) monoclonal antibodies. FIG. 18A. Negative control (no staining). FIG. 18B. With clone LA5 Mab, cells expressing the long isoform of BST2 demonstrated grainy membranous to cytoplasmic staining, while no staining was observed in cell expressing the medium isoform. FIG. 18C. Positive control using anti-BST2 (clone 26F8) mAb. Membranous to cytoplasmic staining was observed in HEK293 cells expressing both the long and the medium isoforms of BST2 protein. Scale is 200 μm.

Figure 19A:
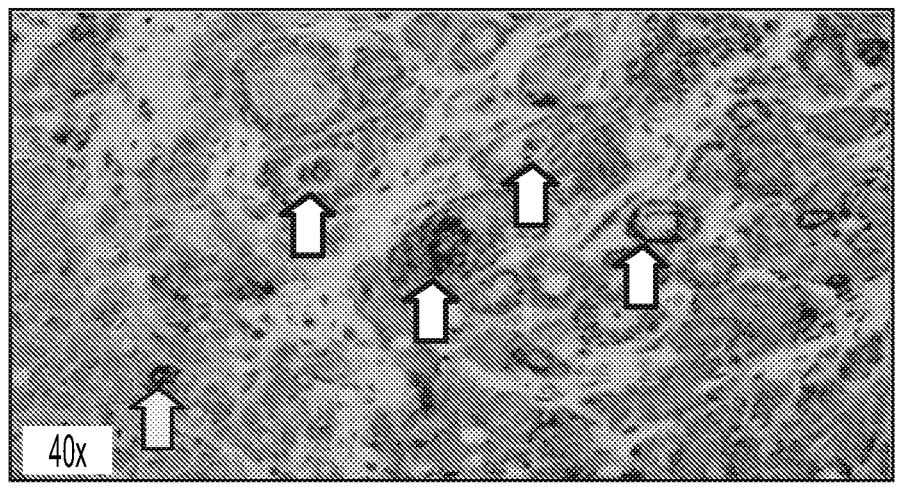
Figure 19B:
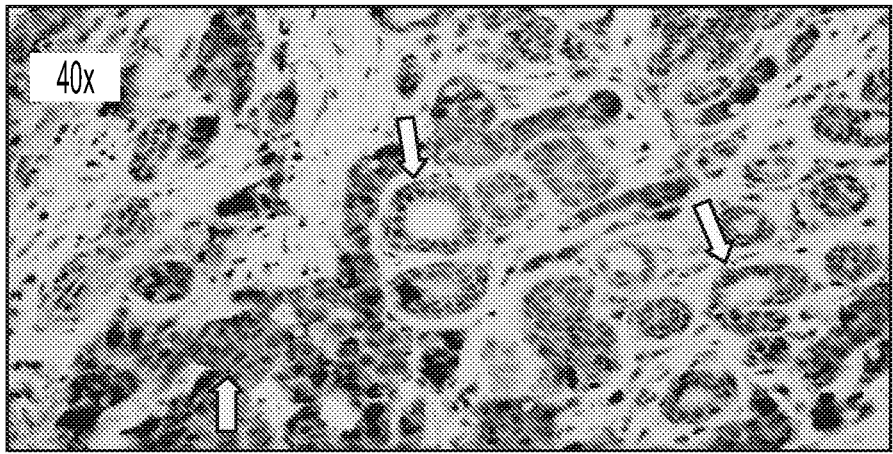

FIGS. 19A-19B. Immunohistochemistry slides of infiltrating ductal breast carcinoma surrounding normal acinus. Immunohistochemistry staining of breast cancer tissue, revealing the expression of the long isoform of BST2 protein. FIG. 19A. Infiltrating ductal breast carcinoma (arrow in bottom left of image) surrounding normal acinus (four arrows in middle of image), using anti-BST2 clone 26F8 mAb. This antibody stained both the normal and malignant cells. FIG. 19B. Infiltrating ductal breast carcinoma (arrow in bottom left of image) surrounding normal acinus (downward-pointing arrows in middle and right of image), using anti-BST2-long clone LA5 mAb. This antibody stained the malignant cells only.

Figure 20A:
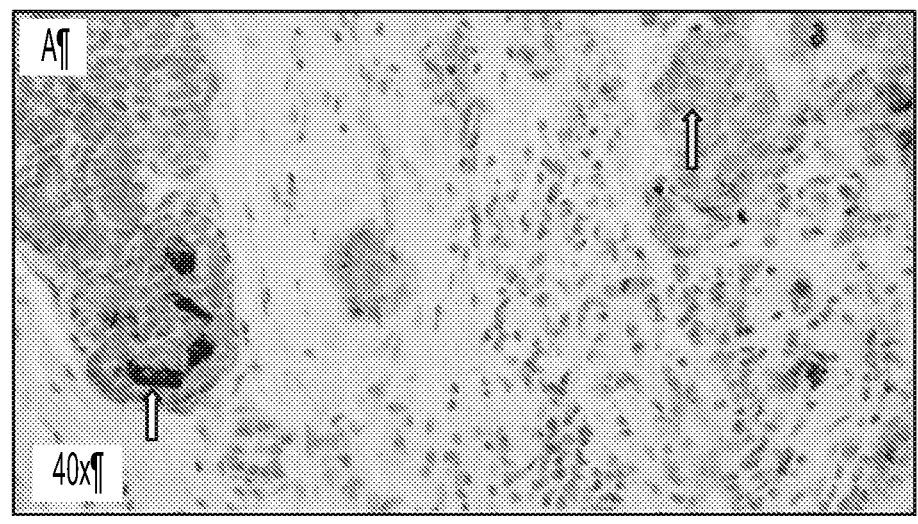
Figure 20B:
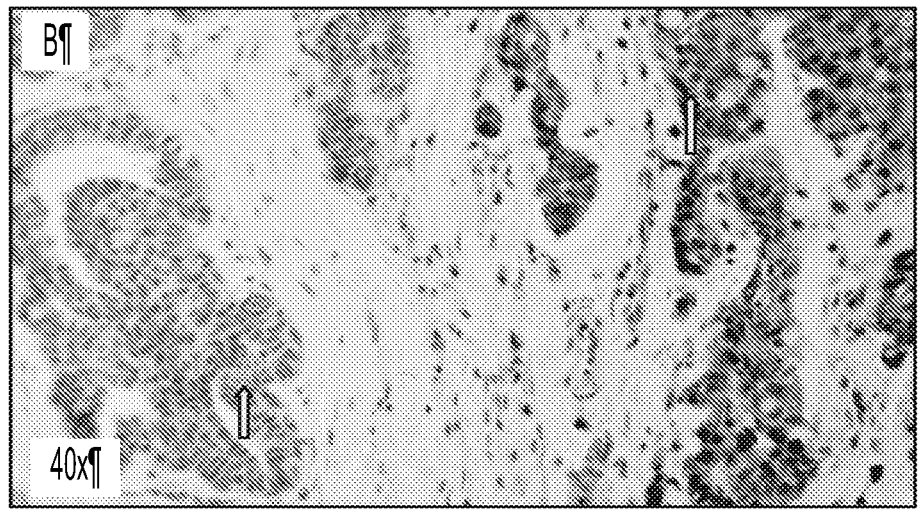

FIGS. 20A-20B. Immunohistochemistry slides of infiltrating ductal breast carcinoma surrounding normal ducts. Immunohistochemistry staining of breast cancer tissue reveal the expression of the long isoform of BST2 protein in malignant cells. FIG. 20A. Infiltrating ductal breast carcinoma (arrow at right of image) surrounding normal ducts (arrow at left of image), using anti-BST2 clone 26F8 mAb. This antibody stained both the normal and malignant cells. FIG. 20B. Infiltrating ductal breast carcinoma (arrow at top right of image) surrounding normal ducts (arrow at bottom left of image), using anti-BST2-long clone LA5 mAb. This antibody stained the malignant cells only.

Figures 21A, 21B, 21C, 21D, 21E, 21F:
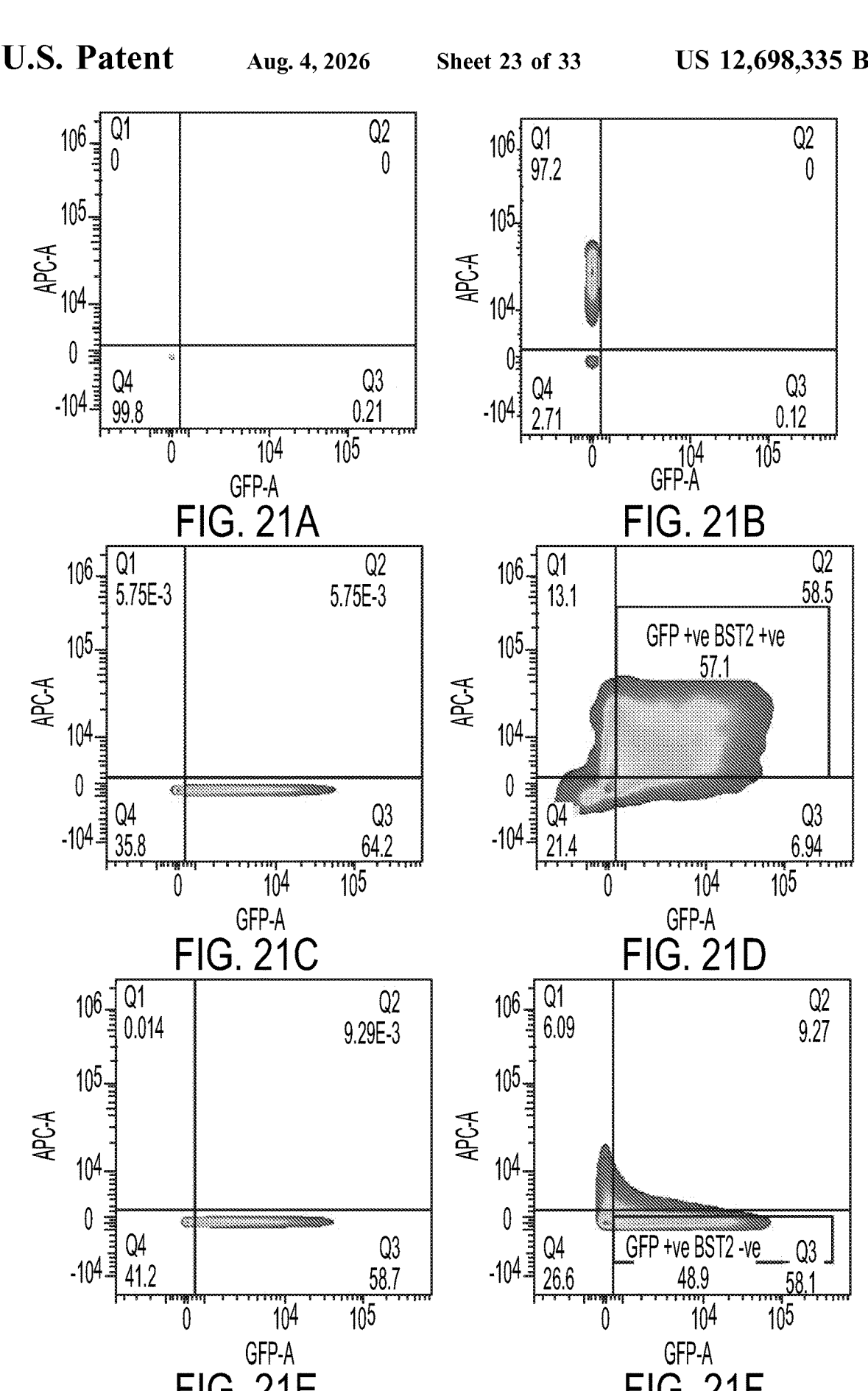

FIGS. 21A-21F. Silencing of BST2 molecule on T47D breast cancer cell line. Flow cytometry dot plots of T47D cell lines. FIGS. 21A and 21B: Dot plot figures of flow cytometry staining of T47D-WT, using secondary antibodies conjugated with Allophycocyanin (APC) alone as a control (FIG. 21A) and anti-BST2 clone 26F8 in a concentration of 2 ug/ml and secondary antibodies conjugated with APC (FIG. 21B). FIGS. 21C and 21D: Dot plot figures of flow cytometry staining of T47D-NS, using secondary antibodies conjugated with APC alone as a control (FIG. 21C) and anti-BST2 clone 26F8 in a concentration of 2 ug/ml and secondary antibodies conjugated with APC (FIG. 21D). FIG. 21C shows a population of cells (64.2%) that is GFP positive, while FIG. 21D demonstrates a percentage of GFP +ve and APC +ve cells=57.1%. These GFP +ve, BST2+ve cells were collected, via cell sorting, and considered as T47D cell line with a nonsilenced transduction (T47D-NS). FIGS. 21E and 21F: Dot plot figures of flow cytometry staining of T47D-BST2-Silenced, using secondary antibodies conjugated with APC alone as a control (FIG. 21E) and anti-BST2 clone 26F8 in a concentration of 2 ug/ml and secondary antibodies conjugated with APC (FIG. 21F). FIG. 21E shows a population of cells (58.7%) that is GFP positive, while FIG. 21D demonstrates a percentage of GFP +ve and APC −ve cells=48.9%. These GFP +ve, BST2−ve cells were collected, via cell sorting, and considered as T47D cell line with a BST2 silenced transduction (T47D BST2-Silenced).

Figure 22:
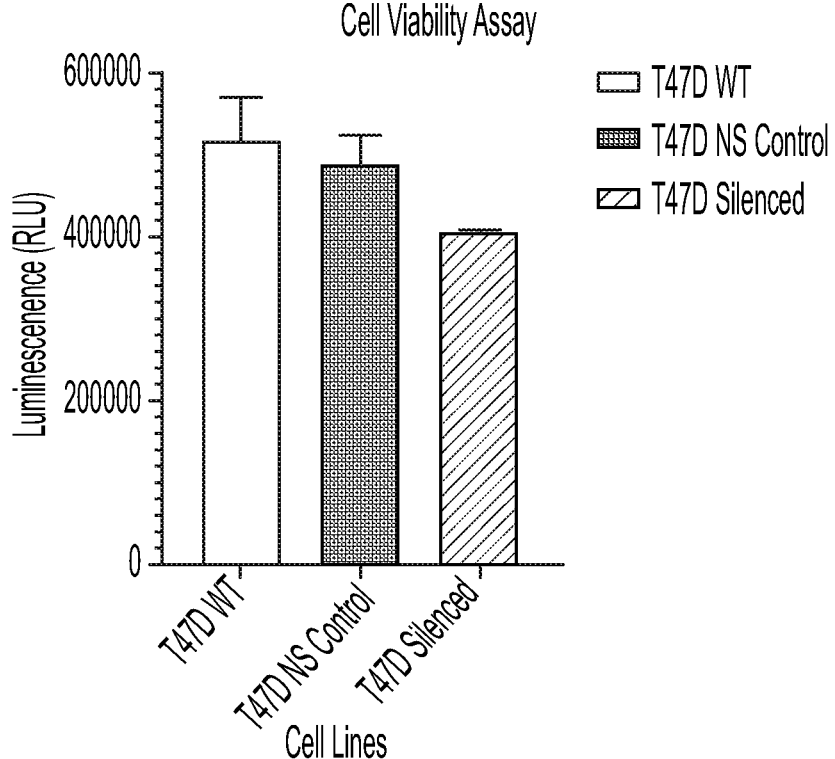

FIG. 22. Cell Viability assay. This figure shows the statistically significant reduction in the viability of T47D cell line with silenced BST2 (P<0.05) (right bar), compared to T47D WT (left bar) and T47D Nonsilenced (NS) transfectant (middle bar).

Figure 23:
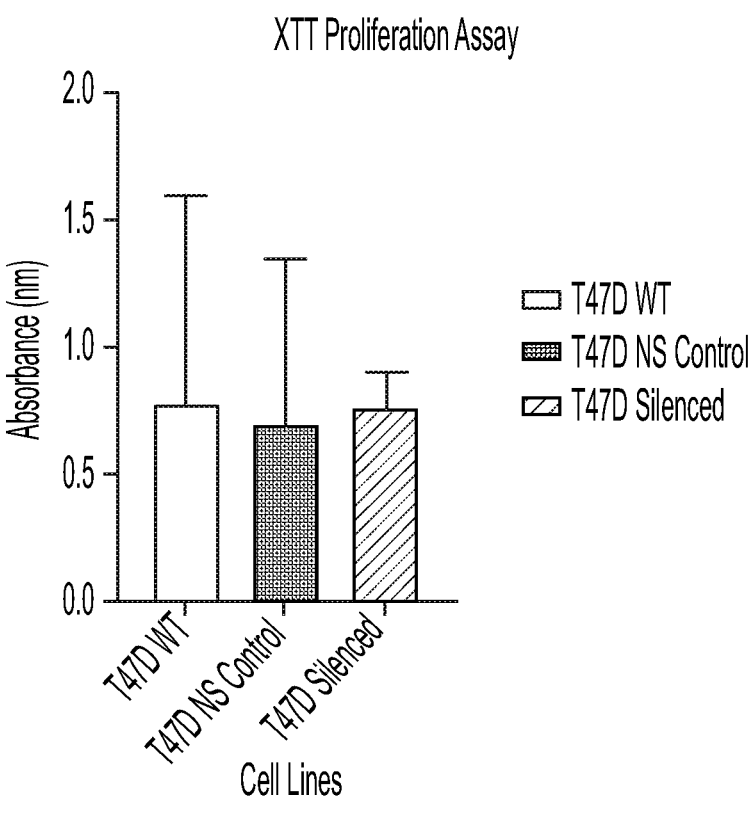

FIG. 23. Cell Proliferation assay. This figure shows no statistically significant change in the proliferation of T47D cell line with silenced BST2 (P value=0.6) (right bar), compared to T47D WT (left bar) and T47D Nonsilenced (NS) transfectant (middle bar).

Figure 24:
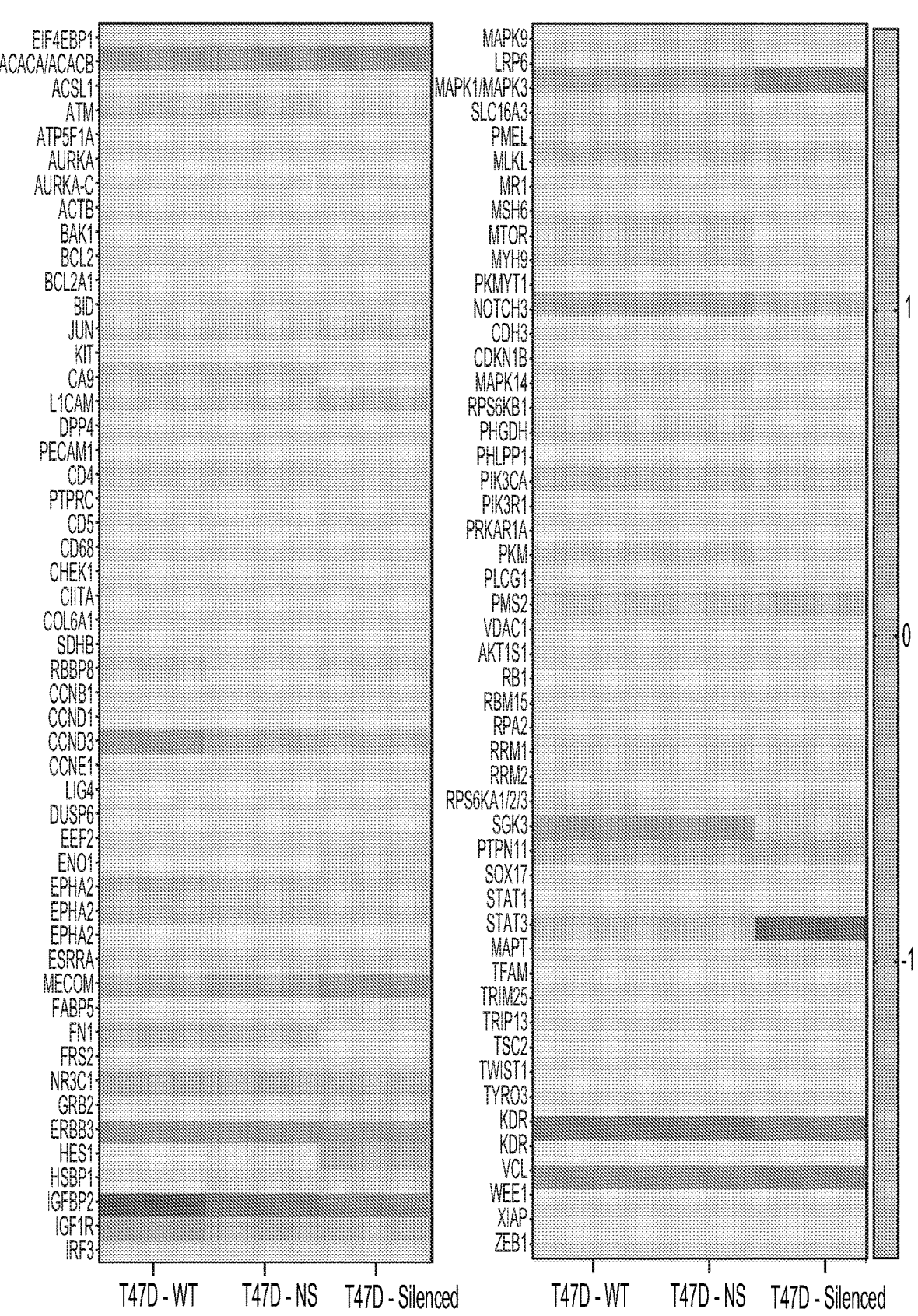

FIG. 24. Heatmap of T47D cell lines. This heatmap visualize changes in the protein expression of 99 genes associated with the silencing of BST2 gene in T47D cell lines. The red color (at the top of the far right bar) suggests an increase above the median value, while the green color (at the bottom of the far right bar) suggests a decrease below the median value.

Figure 25:
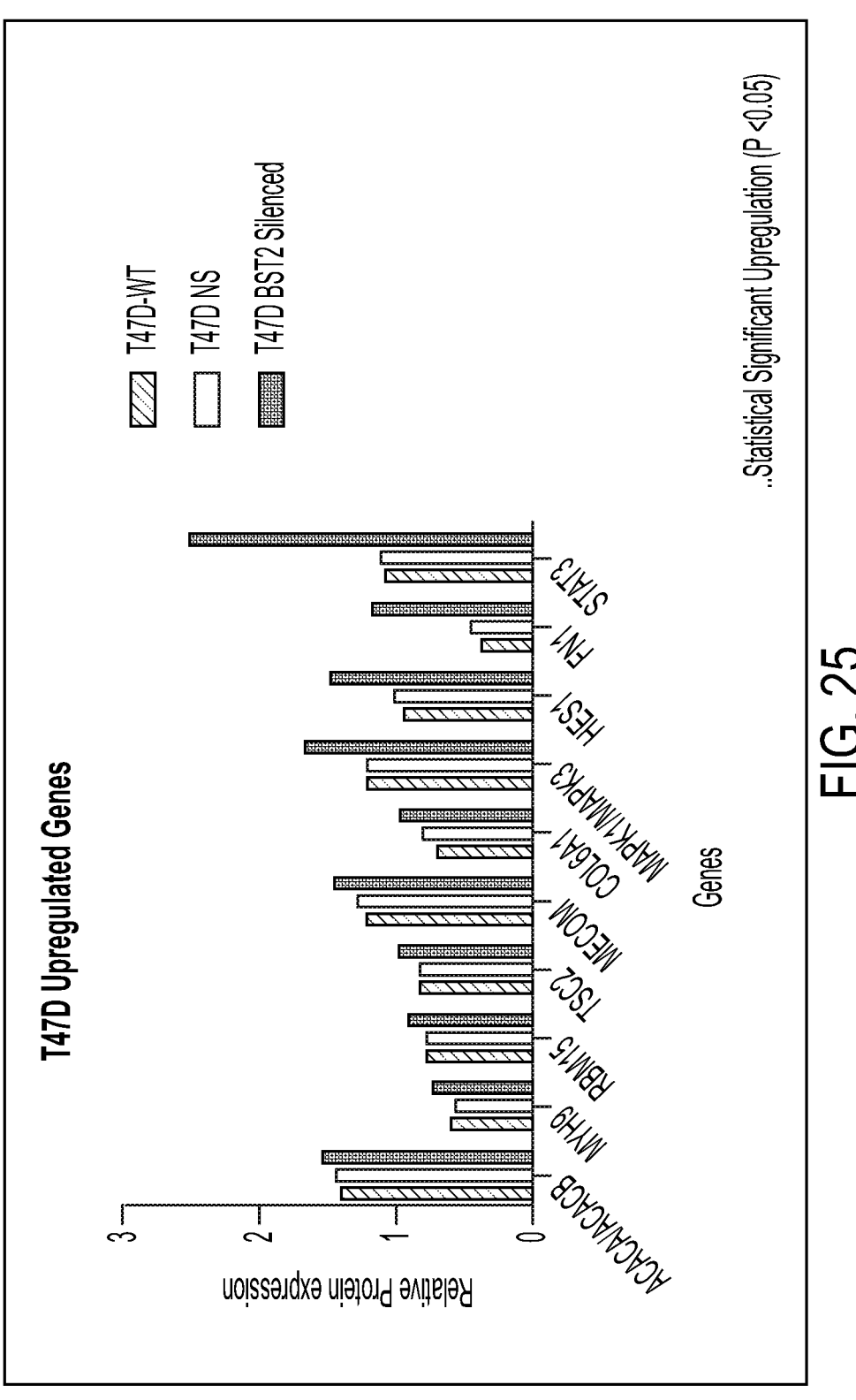

FIG. 25. T47D upregulated genes after BST2 Silencing. This figure compares the level of protein expression of 10 genes among the T47D-WT (red; in a grouping of three bars, the bar on the left), T47D-NS (orange; in a grouping of three bars, the bar in the middle) and T47D-BST2 Silenced (blue; in a grouping of three bars, the bar on the right) cell lines. There was a statistically significant upregulation of the following genes with the silencing of BST2: MAPK1/MAPK3, HES1, FN1 and STAT3 (P value<0.05).

FIG. 26 T47D downregulated genes after BST2 Silencing. This figure compares the level of protein expression of 10 genes among the T47D-WT (red; in a grouping of three bars, the bar on the left), T47D-NS (orange; in a grouping of three bars, the bar in the middle) and T47D-BST2 Silenced (blue; in a grouping of three bars, the bar on the right) cell lines. There was no statistically significant downregulation after silencing BST2 gene.

FIG. 27 tabulates results of immunohistochemistry studies utilizing tissue microarrays of breast cancer samples and normal breast and normal other tissues upon exposure to a commercially available anti-BST2 antibody (MAb 26F8) or an anti-BST2 antibody of the present disclosure. (MAb LA5). Antigen retrieval conditions: Epitope retrieval solution (ER1) citrate-based (pH 6.0), referred to herein as H1. Analysis methods: Using the analysis software Halo (HALO 3.1.1076.449), the analyzable area of the tumor, normal epithelial cells, stroma or parenchymal, and mesenchymal were annotated manually. Individual algorithms were set by training with different antibodies. The cytoplasm positive in the selected areas were scored using the algorithms set by the inventors, intensity (0, 1+, 2+, or 3+) and extension (0-100%) were recorded, and total percentages were summed.

Figure 28:
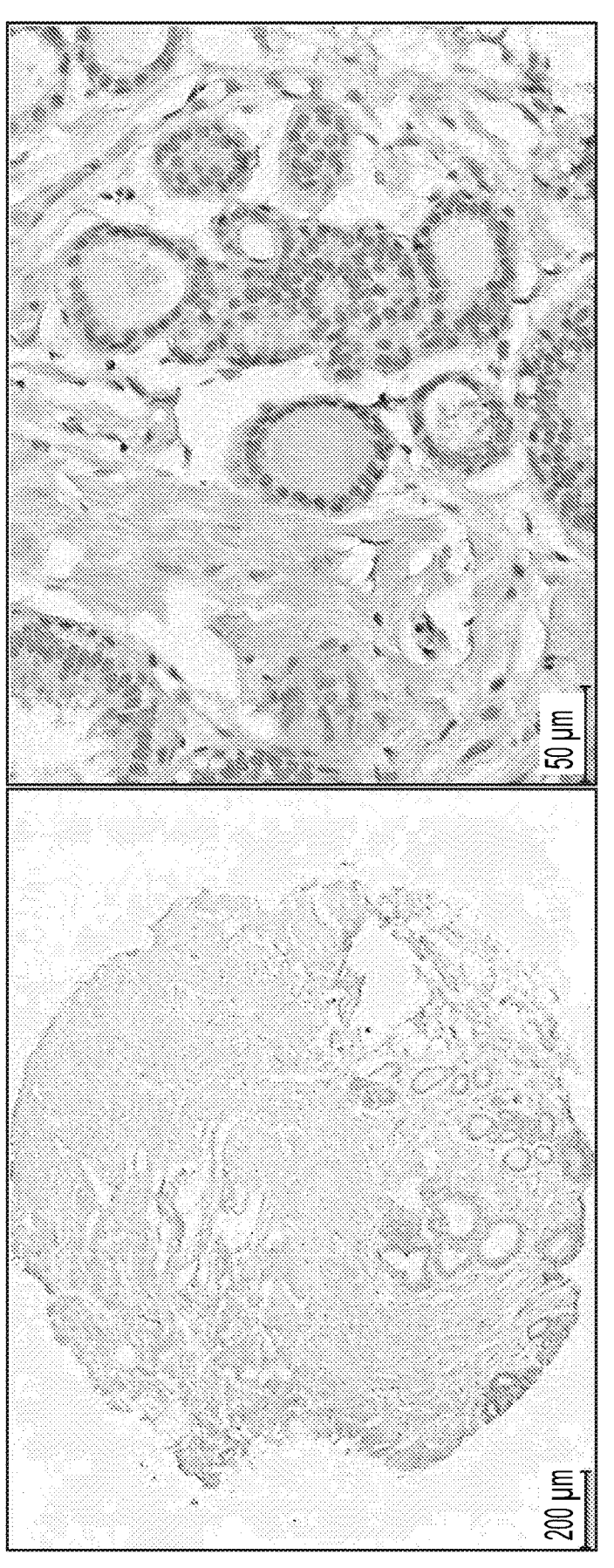

FIG. 28 demonstrates anti-BST2 (Mab 26F8) negative staining (H1, an antigen retrieval solution used for staining) in normal breast, sample 42070 F1, image 13329 (left panel, 8×; right panel, 40×).

Figure 29:
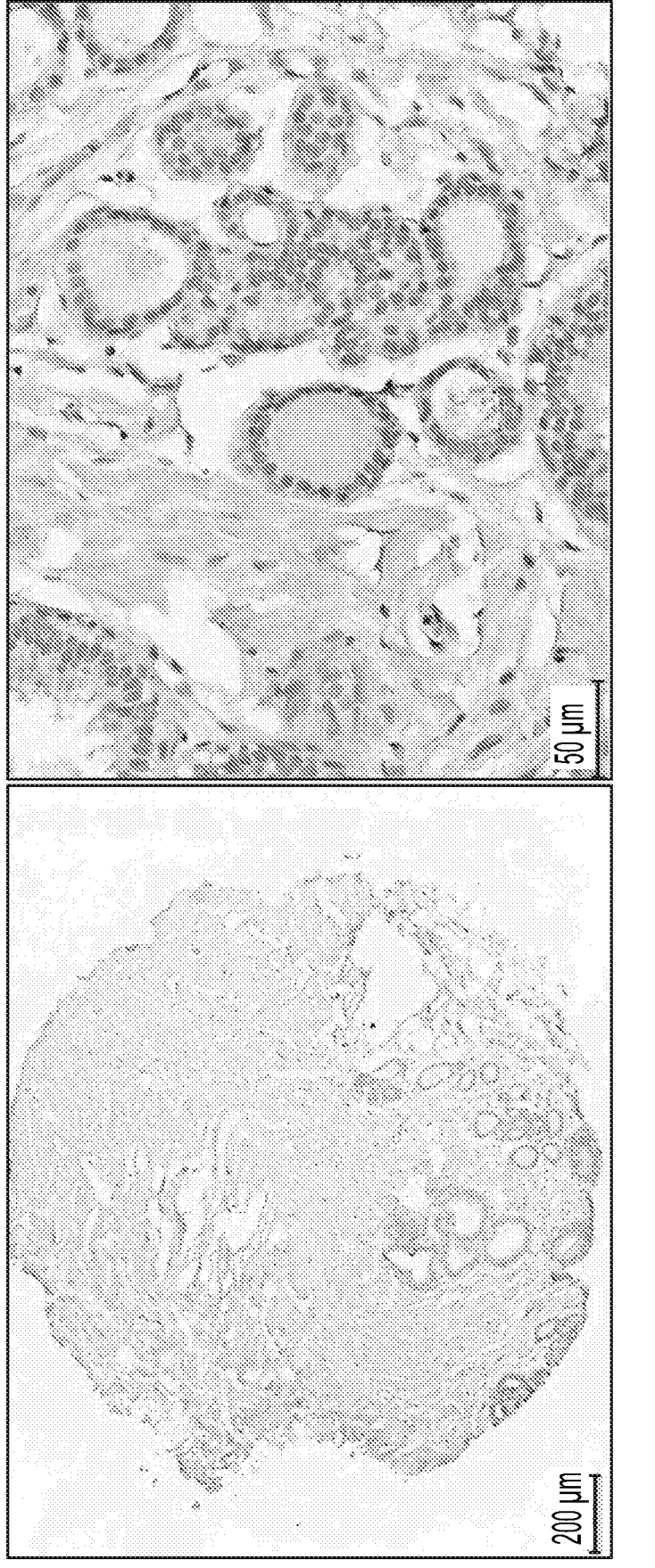

FIG. 29 shows staining with the anti-BST2 long isoform of the present disclosure, (MAb LA5) negative staining in normal breast, sample 42070 F1, image 13330 (left panel, 8×; right panel, 40×). The image in FIG. 29 is a consecutive slice of the image of FIG. 28.

Figure 30:
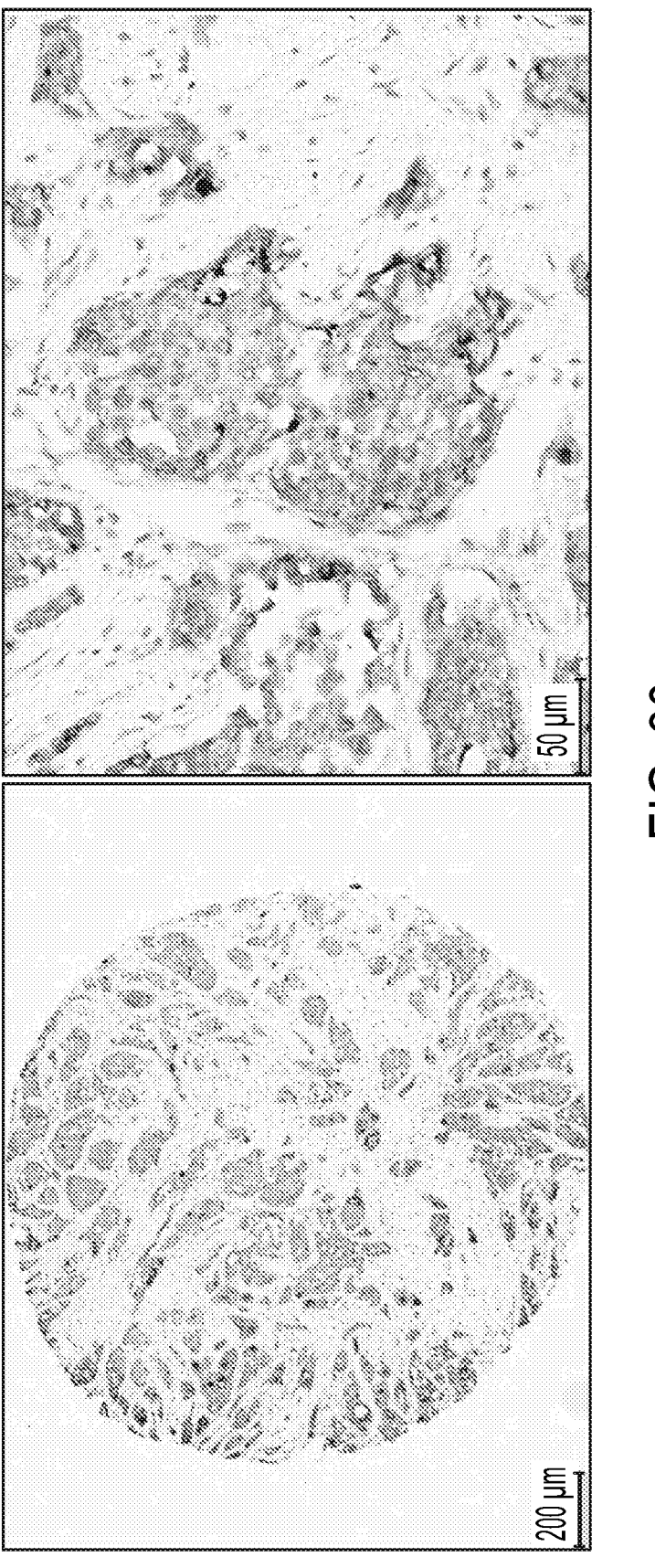

FIG. 30 shows anti-BST2 (Mab 26F8) positive staining in breast invasive ductal carcinoma (BIDC), sample 42070 C8 image 13329 (left panel, 8×; right panel, 40×).

Figure 31:
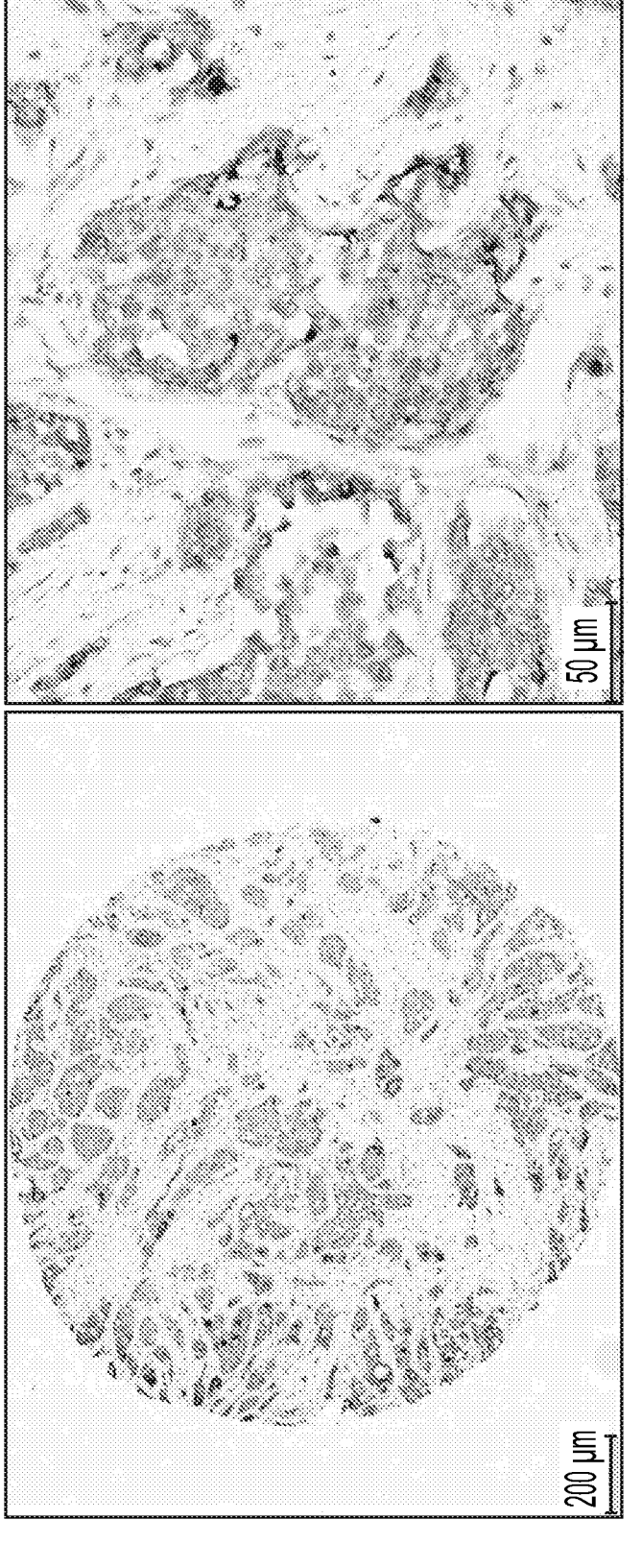

FIG. 31 demonstrates anti-BST2 long isoform (MAb LA5) positive staining in BIDC, sample 42070 C8 image 13330 (L, 8×; R, 40×).

While various embodiments of the disclosure have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the disclosure described herein may be employed.

DETAILED DESCRIPTION

I. Examples of Definitions

In keeping with long-standing patent law convention, the words "a" and "an" when used in the present specification in concert with the word comprising, including the claims, denote "one or more." Some embodiments of the disclosure may consist of or consist essentially of one or more elements, method steps, and/or methods of the disclosure. It is contemplated that any method or composition described herein can be implemented with respect to any other method or composition described herein and that different embodiments may be combined.

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." It is specifically contemplated that x, y, or z may be specifically excluded from an embodiment.

Throughout this application, the term "about" is used according to its plain and ordinary meaning in the area of cell and molecular biology to indicate that a value includes the standard deviation of error for the device or method being employed to determine the value.

The term "binding" or "binds" refers to a direct association between two molecules, due to, for example, covalent, electrostatic, hydrophobic, and ionic and/or hydrogen-bond interactions, including interactions such as salt bridges and water bridges. "Immunologically reactive" means that the selective binding agent or antibody of interest will bind with antigens present in a biological sample. The term "immune complex" refers the combination formed when an antibody or selective binding agent binds to an epitope on an antigen.

The term "comprising," which is synonymous with "including," "containing," or "characterized by," is inclusive or open-ended and does not exclude additional, unrecited elements or method steps. The phrase "consisting of" excludes any element, step, or ingredient not specified. The phrase "consisting essentially of" limits the scope of described subject matter to the specified materials or steps and those that do not materially affect its basic and novel characteristics. It is contemplated that embodiments described in the context of the term "comprising" may also be implemented in the context of the term "consisting of" or "consisting essentially of."

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

The terms "individual," "subject," and "patient," used interchangeably herein, refer to an animal, preferably a mammalian (including non-primate and primate), including, but not limited to, murines, simians, humans, mammalian farm animals (e.g., bovine, porcine, ovine), mammalian sport animals (e.g., equine), and mammalian pets (e.g., canine and feline); preferably the term refers to humans.

As used herein, the terms "treatment", "treating", and the like, refer to obtaining a desired pharmacologic or physiologic effect. The effect may be therapeutic in terms of a partial or complete cure for a disease, symptom, and/or adverse effect attributable to the disease. "Treatment," as used herein, includes administration of a compound of the present invention for treatment of a disease or condition in a mammal, particularly in a human, and includes: (a) inhibiting the disease, i.e., arresting its development; (b) providing palliative care, i.e., reducing and preventing the suffering of a patient; and (c) relieving the disease, i.e., causing regression of the disease or disorder or alleviating symptoms or complications thereof. Dosage regimens may be adjusted to provide the optimum desired response.

BST2 has variable degrees of expression in the body and with respect to most organs. Different isoforms of BST2 are generated by posttranscriptional modification. The present disclosure addresses distribution of the BST2 long isoform in cancer, including at least in B cells and breast tissue cell lines. In particular aspects, the distribution was examined utilizing a novel monoclonal antibody (anti-BST2-long mAb). This new mAb demonstrates a superior ability to detect breast cancer cells embedded in normal tissue, by recognizing specifically the malignant cells while distinguishing and excluding the surrounding normal cells. In particular embodiments, this ability of the mAb provides a useful diagnostic value in detecting infiltrations of breast cancer cells, including malignant breast ductal carcinoma, in ectopic tissues.

In other embodiments of the disclosure, the role of BST2 in breast cancer is characterized. In specific cases, the role in breast cancer is examined using a loss of function approach with BST2-targeting short hairpin RNA (shRNA) in the T47D cell line. Silencing BST2 was associated with a statistically significant reduction in the viability of T47D (p value<0.05) but with no impact on the proliferation (p value=0.6). In particular aspects, the downstream effects of silencing BST2 was evaluated through Reverse Phase Protein Array (RPPA) and which revealed a statistically significant upregulation of 4 genes: MAPK1/MAPK3, HES1, FN1 and STAT3 (P value<0.05). All of these genes play different roles in the survival mechanisms that breast cancer cells may initiate when a critical pathway becomes compromised. As the cellular adaptive response to BST2 silencing is characterized, this disclosure provides approaches for tumor resistance mechanisms in embodiments wherein BST2 protein is utilized as a target in breast cancer therapeutics.

II. BST2 and Related Compositions

The disclosure concerns at least BST2-related peptides, polypeptides, compositions, antibodies, and so forth. Methods of utilizing these compositions are also encompassed herein. BST2 is also referred to in the art as HM1.24, tetherin, and CD317.

The structure of BST2 protein comprises four parts: a cytoplasmic tail representing the amino terminal domain, a transmembrane domain, an extracellular domain and a glycophosphatidylinositol (GPI)—anchor, representing the carboxyl terminal of the protein (6). Being attached to the plasma membrane by two structurally-different anchors gives BST2 an unusual topology. The presence of the GPI—anchor infers that the localization of BST2 is within plasma membrane microdomain (7). BST2 is assembled in dimers through disulfide bonds and can also be found in the cytoplasm, mainly within the trans Golgi network (TGN), as a consequence of Clathrin-mediated internalization from the surface, with data suggesting a continuous cycling of the protein between the cell membrane and the TGN (7).

Figure 1:
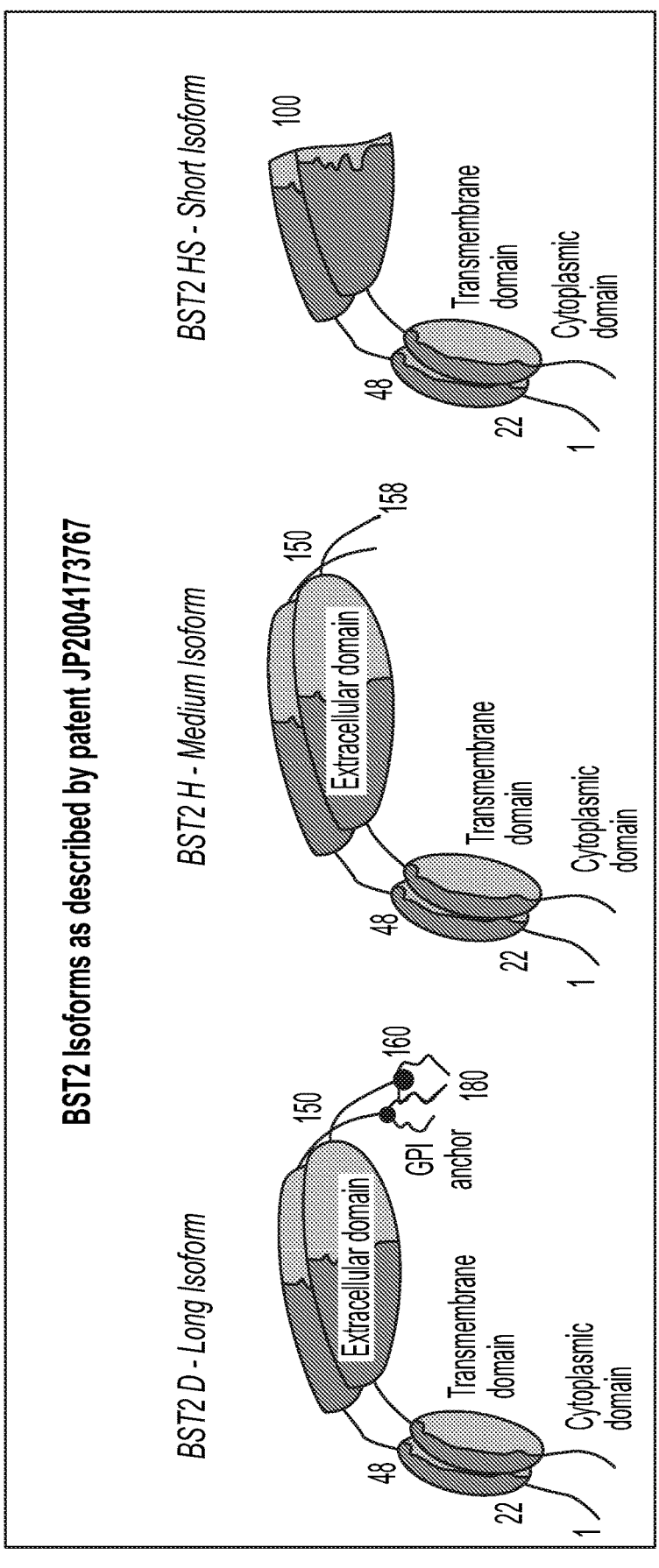
FIG. 1. Examples of BST2 Isoforms. An illustration of three isoforms described in patent JP2004173767: BST2 D—long isoform with 180 amino acids, BST2 H—Medium isoform with 158 amino acids, and BST2 HS—short isoform with 100 amino acids.
Figure 2:
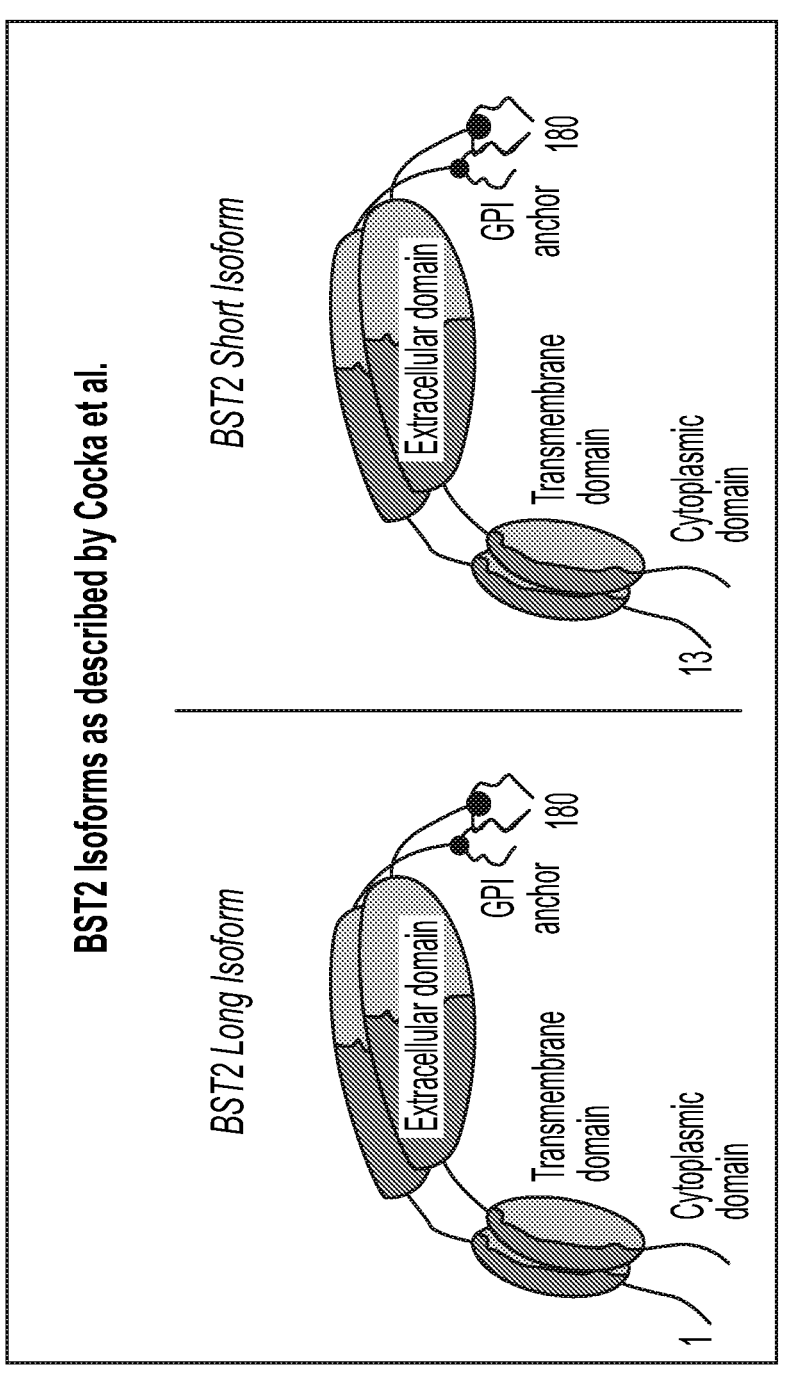
FIG. 2. Examples of BST2 Isoforms. An illustration of two isoforms described by Cocka et al. (2012). BST2 long isoform with 180 amino acids and BST2 short isoform with 168 amino acids, lacking the first 12 amino acids.

Different research groups described various isoforms of BST2 protein, as a result of alternative splicing. In 2005, a Japanese group identified three splice variants of BST2: BST2-D, BST2-H and BST2-HS (patent no. JP2004173767) (27). These variants differed in the length of the protein and partially in the sequence of amino acids. The isoforms were defined as followed: BST2-D (the long isoform) is 180 amino acids, BST2-H (the medium isoform) is 158 amino acids and BST2-HS (the short isoform) is only 100 amino acids (FIG. 1).

In 2012, Cocka et al. described two isoforms of Tetherin/BST2, a long isoform and a short isoform (28). As a consequence of alternative translation initiation, these isoforms were unrelated to those described earlier by the Japanese patent, with the short isoform lacking the first 12 amino acids that presents in the long isoform. Moreover, Cocka et al. demonstrated that these isoforms were associated with distinct antiviral and signaling activities.

These BST2 isoforms may merge with a similar or a different isoform, forming homo- or heterodimers, respectively. Mechanisms that govern such interactions between these isoforms to build dimers are not well understood; however, this formation of homo- and heterodimers may have substantial effects on the functional roles of BST2. Although both isoforms have the ability to restrict viral budding and release, through tethering the viral particles, the short isoform is more resistant to Vpu-mediated HIV antagonism. BST2 is a known activator of the Nuclear Factor—Kappa B (NF-kappa B) pathway, a signaling pathway that is involved in many biological activities, including the regulation of immune responses and inflammation (28). Unregulated activation of this pathway has been associated with carcinogenesis processes, including proliferation, migration and invasion (29). The long BST2 isoform appeared as a potent activator of the NF-kappa B pathway, while the short isoform displayed no activation. Moreover, the short isoform exhibited an ability to modulate the effect of the long isoform on this pathway, and heterodimers demonstrated reduced NF-kappa B signaling. Also, increasing the number of short BST2 isoforms, relative to the long isoform, diminished the activity of this pathway, suggesting an inhibitory role for the short isoform in regulating Nuclear Factor—Kappa B pathway signaling by the BST2—long isoform (28).

The present disclosure provides BST2 peptides useful for a variety of applications, such as generation of an antibody thereto or useful for vaccination, engineered antigen receptors, cells comprising the peptides, antibodies thereto, and/or receptors, and methods of making and using the peptides, antibodies, and/or cells that express them. In particular embodiments, the disclosure encompasses any antibody that binds such peptides. In certain embodiments, the peptides comprise, consist of, or consist essentially of sequence from BST2, including the long form of BST2, such as SEQ ID NO:1 (EVERLRRENQVLSVRIADKKYYPS), SEQ ID NO:2 (RENQVLSVRIADKKYYPS), or SEQ ID NO:4 (RENQVLSVRI). Aspects of the disclosure relate to an isolated peptide comprising at least 70% (or 75%, 80%, 85%, 90%, or 95%) sequence identity to a peptide with the amino acid sequence of SEQ ID NO:1, SEQ ID NO:2, or SEQ ID NO:4. In some embodiments, the peptide has at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:1, SEQ ID NO:2, or SEQ ID NO:4.

Peptides encompassed herein include those derived from the long form of BST2, which is as follows:

```
                                            (SEQ ID NO: 3)
   1  mastsydycr vpmedgdkrc klllgigilv lliivilgvp
      liiftikans eacrdglrav 61  mecrnvthll qqelteaqkg fqdveaqaat cnhtvmalma
      sldaekaqgq kkveelegei 121  ttlnhklqda saeverlrre nqvlsvriad kkyypssqds
      ssaaapqlli vllglsallq.
```

In some embodiments, the peptide comprises at least 4 contiguous amino acids of a peptide of SEQ ID NO:1, SEQ ID NO:2, or SEQ ID NO:4. In some embodiments, the peptide comprises at least 4, 5, 6, 7, 8, or 9 contiguous amino acids of a peptide of SEQ ID NO:1, SEQ ID NO:2, or SEQ ID NO:4. In some embodiments, the peptide comprises or consists of or consists essentially of SEQ ID NO:1, SEQ ID NO:2, or SEQ ID NO:4. In some embodiments, the peptide has at least, at most, exactly, or consists of 7, 8, 9, 10, 11, 12, 13, 14, 15, 16, 17, 18, 19, 20, 21, 22, 23, or 24 amino acids (or any range derivable therein). In some embodiments, the peptide is immunogenic. The term immunogenic may refer to the triggering of an immune response, such as a protective immune response. In some embodiments, the peptide is modified. In some embodiments, the modification comprises conjugation to a molecule. The molecule may be an antibody, a lipid, an adjuvant, or a detection moiety (tag). In some embodiments, the peptide comprises 100% sequence identity to a peptide of SEQ ID NO:1, SEQ ID NO:2, or SEQ ID NO:4. Peptides of the disclosure also include those that have at least 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% sequence identity to a peptide of SEQ ID NO:1, SEQ ID NO:2, or SEQ ID NO:4. The peptides of the disclosure may have 1, 2, or 3 substitutions relative to a peptide of SEQ ID NO:1, SEQ ID NO:2, or SEQ ID NO:4. In some embodiments, the peptide has at least or has at most 1, 2, 3, 4, or 5 substitutions relative to a peptide of SEQ ID NO:1, SEQ ID NO:2, or SEQ ID NO:4.

The disclosure comprises the generation of an antagonist anti-BST2-Long isoform antibody. Mice were immunized with a peptide-Keyhole limpet hemocyanin (KLH) comprising the amino acid sequence EVERLRRENQVLSVRIAD-KKYYPS (SEQ ID NO:1), which is located at the BST2 protein positions: 133-156. The total number of residues is 24. It has a molecular weight: 2949.32 g/mol and an Isoelectric point: pH=10. The peptide-KLH conjugated was used for immunization and the screening of the generated antibodies was performed in an ELISA assay, developed against the peptide-KLH and peptide alone, to distinguish the specific antibodies against the peptide sequence.

In another embodiment, a peptide to immunize mice is a shorter version that makes the target even more specific to the long isoform (RENQVLSVRIADKKYYPS; SEQ ID NO:2). The positive antibodies selected after the screening of supernatants from hybridomas containing antibodies were LA1, LA5, LA8, LA15, BM2, BM5, BM7 and BM8. All the antibodies recognize the peptide non KLH. Using the supernatant of antibodies for FACS staining of HEK-293 cells transduced to express the medium and long isoforms respectively, LA1, LA5, LA15 and BM7, showed binding preferentially to the long but not medium isoforms.

Yet further aspects relate to nucleic acids encoding the peptides, polypeptides, fusion proteins, and engineered antigen receptors. The disclosure also describes nucleic acid vectors comprising one or more nucleic acids of the disclosure, and cells comprising the peptides, fusion proteins, polypeptides, engineered antigen receptors, bispecific antibodies, and/or nucleic acids of the disclosure. Also provided are compositions comprising the peptides, polypeptides, cells, nucleic acids, or engineered TCRs of the disclosure. Further aspects relate to a method of making an engineered cell comprising transferring a nucleic acid or vector of the disclosure into a cell.

Nucleic acids of the disclosure include those that encode for complementarity-determining regions (CDRs), variable regions, engineered antigen receptors, polypeptides, and fusion proteins encompassed herein. In some embodiments, the nucleic acid comprises one of SEQ ID NOS:5, 6, 9, 11, 13, 14, 15, 18, 19, 21, 22, 28, 31, 32, 34, 35, 36, 39, 41, 43, 44, 45, 48, 49, 51, 52, 53, 56, 58, 60, or 61, or a fragment thereof. In some embodiments, the nucleic acid comprises a nucleotide with at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to one of SEQ ID NOS:5, 6, 9, 11, 13, 14, 15, 18, 19, 21, 22, 28, 31, 32, 34, 35, 36, 39, 41, 43, 44, 45, 48, 49, 51, 52, 53, 56, 58, 60, or 61, or a fragment thereof.

Embodiments of the disclosure include engineered antigen receptors or bispecific or multi-specific antibodies (such as engagers) that comprise antibodies that bind the long isoform of BST2. In specific embodiments, the engineered antigen receptors are chimeric antigen receptors or engineered T-cell receptors. In specific cases, the engineered antigen receptors or bispecific or multi-specific antibodies comprise a LA5 scFv comprising a CDR-H1 that comprises an amino acid sequence as set forth in SEQ ID NO: 8 (GFNIKDYY), CDR-H2 that comprises the amino acid sequence as set forth in SEQ ID NO: 10 (IDPENGDT), CDR-H3 that comprises the amino acid sequence as set forth in SEQ ID NO: 12 (KRGD), CDR-L1 that comprises the amino acid sequence as set forth in SEQ ID NO: 17 (QSIVHSNGNTY), CDR-L2 that comprises the amino acid sequence of KVS, and CDR-L3 that comprises the amino acid sequence as set forth in SEQ ID NO: 20 (FQGSHAPFT). In other cases, the engineered antigen receptors or bispecific or multi-specific antibodies comprise a LA1 scFv comprising a CDR-H1 comprises an amino acid sequence as set forth in SEQ ID NO: 38 (GYTFTEDT), CDR-H2 comprises the amino acid sequence as set forth in SEQ ID NO: 40 (INPNKGGT), CDR-H3 comprises the amino acid sequence as set forth in SEQ ID NO: 42 (ATLVDY), CDR-L1 comprises the amino acid sequence as set forth in SEQ ID NO: 30 (QNVGTN), CDR-L2 comprises the amino acid sequence of SAS, and CDR-L3 comprises the amino acid sequence as set forth in SEQ ID NO: 33

(QQYNSYPLT). In specific cases, the engineered antigen receptors or bispecific or multi-specific antibodies comprise a BM7 scFv comprising a CDR-H1 comprises an amino acid sequence as set forth in SEQ ID NO: 55 (GFSLSTSGVG), CDR-H2 comprises the amino acid sequence as set forth in SEQ ID NO: 57 (IWWDDDE), CDR-H3 comprises the amino acid sequence as set forth in SEQ ID NO: 59 (ARRYYGDAMDY), CDR-L1 comprises the amino acid sequence as set forth in SEQ ID NO: 47 (QSLVHSNGHTY), CDR-L2 comprises the amino acid sequence of KVS, and CDR-L3 comprises the amino acid sequence as set forth in SEQ ID NO: 50 (SQSTHVPYT).

III. BST2 Antibodies

In particular embodiments of the disclosure, the particular peptides from BST2 are utilized for generation of antibodies of any kind.

Certain embodiments of the present disclosure are directed to an antibody, e.g., a monoclonal antibody that recognizes BST2 or a cell expressing the same. The disclosure is also directed to a hybridoma cell line that produces the antibody, and to methods of treating cancer using the antibody. The antibody recognizes and specifically binds the long isoform of human BST2 in its native form, which is expressed on the cellular membrane.

The term "antibody" is used herein in the broadest sense and refers generally to a molecule that contains at least one antigen binding site that immunospecifically binds to a particular antigen target of interest. The term "antibody" thus includes but is not limited to antibodies and variants thereof, fragments of antibodies and variants thereof, peptibodies and variants thereof, and antibody mimetics that mimic the structure and/or function of an antibody or a specified fragment or portion thereof, including single chain antibodies and fragments thereof. The term "antibody," thus includes full-length antibodies or their variants as well as fragments thereof. Binding of an antibody to a target can cause a variety of effects, such as but not limited to, it modulates, decreases, increases, antagonizes, agonizes, mitigates, alleviates, blocks, inhibits, abrogates or interferes with at least one target activity or binding, or with receptor activity or binding, in vitro, in situ, and/or in vivo.

The present disclosure, thus, encompasses antibodies capable of binding to BST2 or portions thereof, including but not limited to Fab, Fab' and F(ab')2, facb, pFc', Fd, Fv or scFv fragments; diabodies; linear antibodies; single-chain antibody molecules; and multi-specific antibodies formed from antibody fragments.

Accordingly, the term "antibody" is used in the broadest sense and specifically covers, for example, single anti-BST2 monoclonal antibodies (including agonist, antagonist, and neutralizing antibodies), anti-BST2 antibody compositions with poly-epitopic specificity, single chain anti-BST2 antibodies, and fragments of anti-BST2 antibodies.

The term "monoclonal antibody" as used herein refers to an antibody obtained from a population of substantially homogeneous antibodies, i.e., the individual antibodies comprising the population are identical except for possible naturally occurring mutations that may be present in minor amounts. In certain aspects a monoclonal antibody that specifically binds a long isoform of BST2 peptide is described.

Specific antibody fragments of the present disclosure include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-46) which consists of a single variable, (v) isolated CDR regions, (vi) F(ab')2 fragments, a bivalent fragment comprising two linked Fab fragments, (vii) single chain Fv molecules (scFv), wherein a VH domain and a VL domain are linked by a peptide linker which allows the two domains to associate to form an antigen binding site (Bird et al., 1988, Science 242:423-26, Huston et al., 1988, Proc. Natl. Acad. Sci. U.S.A. 85:5879-83), (viii) bispecific single chain Fv (WO 03/11161) and (ix) "diabodies" or "triabodies", multivalent or multispecific fragments constructed by gene fusion (Tomlinson et. al., 2000, Methods Enzymol. 326:461-79; WO94/13804; Holliger et al., 1993, Proc. Natl. Acad. Sci. U.S.A. 90:6444-48). The antibody fragments may be modified. For example, the molecules may be stabilized by the incorporation of disulfide bridges linking the VH and VL domains (Reiter et al., 1996, Nature Biotech. 14:1239-1245).

"Fv" is the minimum antibody fragment that contains a complete antigen-recognition and binding site. This region consists of a dimer of one heavy-chain and one light-chain variable domain in tight, non-covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "scFv" antibody fragments comprise the VH and VL domains of antibody, wherein these domains are present in a single polypeptide chain. Preferably, the Fv polypeptide further comprises a polypeptide linker between the VH and VL domains that enables the sFv to form the desired structure for antigen binding. For a review of scFv, see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) Proc. Natl. Acad. Sci. USA 90:6444.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, the antibody will be purified to greater than 95% by weight of antibody as determined by the Lowry method, and most preferably more than 99% by weight; to a degree sufficient to obtain at least 15 residues of N-terminal or internal amino acid sequence by use of a spinning cup sequenator; or to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As use herein, the term "specifically binds to" or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (KD) of $<1\times10^{-6}$ M, $<1\times10^{-7}$ M, $<1\times10^{-8}$ M, $<1\times10^{-9}$ M, or $<1\times10^{-10}$ M.

"Antibody-dependent cell-mediated cytotoxicity" or ADCC refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRI, FcγRII and FcγRIII Fc expression on hematopoietic cells is summarized in Table 3 on page 464 of Ravetch and Kinet, Annu. Rev. Immunol. 9: 457-92 (1991).

"Binding affinity" generally refers to the strength of the sum total of non-covalent interactions between a single binding site of a molecule (e.g., of an antibody) and its binding partner (e.g., an antigen). Unless indicated otherwise, as used herein, "binding affinity", "bind to", "binds to" or "binding to" refers to intrinsic binding affinity that reflects a 1:1 interaction between members of a binding pair (e.g., antibody Fab fragment and antigen). The affinity of a molecule X for its partner Y can generally be represented by the dissociation constant (KD). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative and exemplary embodiments for measuring binding affinity.

The "KD" or "KD value" according to this invention is in one embodiment measured by surface plasmon resonance using BiaCore® (Cytiva) or OCTET platform (ForteBIO).

The term "conformational epitope" as used herein refers to amino acid residues of the antigen that come together on the surface when the polypeptide chain folds to form the native protein.

A. Monoclonal Antibodies

The anti-BST2 antibodies may be monoclonal antibodies. Monoclonal antibodies may be prepared using hybridoma methods, such as those described by Kohler and Milstein (1975) Nature 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

An immunizing agent typically includes the BST2 polypeptide, peptide, or a fusion protein thereof. In certain aspects, an immunizing agent is a virus-like particle (VLP) with a BST2 peptide displayed on its surface. Generally, either peripheral blood mononuclear cells enriched in plasma B cells are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding (1986) Monoclonal Antibodies: Principles and Practice, Academic Press, pp. 59-103). Immortalized cell lines may be transformed mammalian cells, particularly myeloma cells of rodent, bovine and human origin. Rat or mouse myeloma cell lines may be employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Particular immortalized cell lines are those that fuse efficiently, support stable high-level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, J. (1984) Immunol. 133:3001; Brodeur et al. (1987) Monoclonal Antibody Production Techniques and Applications, Marcel Dekker, Inc., New York, pp. 51-631).

The culture medium in which the hybridoma cells are cultured can then be assayed for the presence of monoclonal antibodies directed against BST2 or the BST2 peptides described herein. The binding specificity of monoclonal antibodies produced by the hybridoma cells can be determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined using BiaCore® or OCTET platform.

The monoclonal antibodies secreted by the subclones may be isolated or purified from the culture medium or ascites fluid by conventional immunoglobulin purification procedures such as protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures, e.g., by using oligonucleotide probes that are capable of binding specifically to genes encoding the heavy and light chains of murine antibodies. The hybridoma cells of the invention serve as a preferred source of such DNA. Once isolated, the DNA may be placed into expression vectors, which are then transfected into host cells, such as, simian COS cells, Chinese hamster ovary (CHO) cells, or myeloma cells that do not otherwise produce immunoglobulin protein, in order to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al., supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bifunctional or multifunctional antibody with non-identical antigenic binding specificities, each of which may be monovalent, bivalent, or multivalent.

The antibodies of the present disclosure may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

The anti-BST2 monoclonal antibodies of the invention may be whole or an antigen-binding fragment of the antibody that binds to a BST2 polypeptide or peptide, preferably a native sequence BST2 polypeptide. Furthermore, in certain embodiments the monoclonal antibody is identified as having recognition of a BST2 protein expressed by at least one cancer cell line or tumor tissue.

In one non-limiting embodiment the monoclonal antibody is produced by hybridoma cell line, wherein said antibody or functional fragment thereof binds to a BST2 protein and wherein said antibody or functional fragment thereof binds a CSC, neoplastic cell, tumor tissue or antigen thereof as said antibody or functional fragment thereof.

B. Human and Humanized Antibodies

The monoclonal antibodies of the present invention can be human or humanized to reduce the immunogenicity for use in humans. Humanized forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al. (1986) Nature 321:522; Riechmann et al. (1988) Nature 332:323; and, Presta (1992) Curr. Op. Struct. Biol. 2:593).

Methods for humanizing non-human antibodies are well known in the art. An example approach is to make mouse-human chimeric antibodies having the original variable region of the murine monoclonal antibodies, joined to constant regions of a human immunoglobulin. Chimeric antibodies and methods for their production are known in the art. See, e.g., Cabilly et al., European Patent EP0125023 (published Mar. 3, 2002); Taniguchi et al., European Patent EP0171496 (published May 26, 1993); Morrison et al., European Patent Application EP0173494 (published Jan. 18, 1986); Neuberger et al., International Publication No. WO/1986/01533, (published Mar. 13, 1986); Kudo et al., European Patent Application EP0184187 (published Jun. 11, 1986); Robinson et al., International Publication No. WO/1987/002671 (published May 7, 1987); Liu et al. (1987) Proc. Natl. Acad. Sci. USA 84:3439; Sun et al. (1987) Proc. Natl. Acad. Sci. USA 84:214; Better et al. (1988) Science 240:1041. These references are incorporated herein by reference. Generally, DNA segments encoding the H and L chain antigen-binding regions of the murine mAb can be cloned from the mAb-producing hybridoma cells, which can then be joined to DNA segments encoding CH and CL regions of a human immunoglobulin, respectively, to produce murine-human chimeric immunoglobulin-encoding genes.

A chimeric antibody can be further humanized by replacing sequences of the Fv variable region which are not directly involved in antigen binding with equivalent sequences from human Fv variable regions. General methods for generating humanized antibodies are provided by Morrison, S. L., 1985, Science 229:1202-1207 by Oi et al., 1986, BioTechniques 4:214, and by Queen et al. U.S. Pat. Nos. 5,585,089, 5,693,761 and 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from 7E3, an anti-GPIIbIIIa antibody producing hybridoma. The recombinant DNA encoding the chimeric antibody can then be cloned into an appropriate expression vector.

Generally, in a humanized antibody the CDR regions are of murine origin, whereas the remainder of the variable regions are of human origin. Humanization can be essentially performed following the method of Winter and coworkers (Jones et al. (1986) Nature 321:522; Riechmann et al. (1988) Nature 332:323; Verhoeyen et al. (1988) Science 239:1534), by substituting rodent CDRs or CDR sequences for the corresponding sequences of a human antibody. See also U.S. Pat. No. 5,225,539 and Beidler et al. 1988 J. Immunol. 141:4053.

Human antibodies can also be produced using various techniques known in the art, including phage display libraries (Hoogenboom and Winter, J. Mol. Biol., 227:381 (1991); Marks et al. J. Mol. Biol., 222:581 (1991)). The techniques of Cole et al. and Boemer et al. are also available for the preparation of human monoclonal antibodies (Cole et al., Monoclonal Antibodies and Cancer Therapy, Alan R. Liss, p. 77 (1985) and Boerner et al. J. Immunol., 147(1):86 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al. Bio/Technology 10:779 (1992); Lonberg et al. Nature 368:856 (1994); Morrison, Nature 368:812 (1994); Fishwild et al. Nature Biotechnology 14:845 (1996); Neuberger, Nature Biotechnology 14:826 (1996); Lonberg and Huszar, Intern. Rev. Immunol. 13:65 (1995).

C. Examples of Specific BST2 Antibodies

The examples herein encompass generation of at least the LA5, LA1, and BM7 antibodies that bind the long form of BST2. Certain monoclonal antibodies were generated from the sequence of SEQ ID NO:1 and are encompassed herein.

LA5 Antibody

Analysis of the LA5/H9 hybridoma embodiment of a BST2 antibody is as follows:

(SEQ ID NO: 5)

```
TGGAGTATCAACGCAGAGTACATGGGGATATGAACACTGTTTTCTCTACA

GTCACTGAATCTCAAGGTCCTTACAATGAAATGCAGCTGGGTCATCTTCT

TCCTGATGGCAGTGGTTATAGGAATCAATTCAGAGGTTCAGCTGCAGCAG

TCTGGGGCAGAGCTTGTGAGGTCAGGGGCCTCAGTCAACTTGTCCTGCAC

AGCTTCTGGCTTCAACATTAAAGACTACTATATACACTGGGTGAAGCAGA

GGCCTGAACGGGGCCTGGAGTGGATTGGATGGATTGATCCTGAGAATGGT

GATACTGAATATGCCCCGGAGTTCCAGGGCAAGGCCTCTATGACTGCAGA

CACATCCTCCAACACAGCCTACCTGCAGCTCAGCAGCCTGACATCTGAGG

ACACTGCCGTCTATTACTGTAAGCGAGGGGACTGGGGCCAAGGGACTCTG

GTCACTGTCTCTGCAGCCAAAACGACACCCCCATCTGTCTATCCACTGGC

CCCTGGATCTGCTGCCCAAACTAACTCCATGGTGACCCTGGGATGCCTGG

TCAAGGGCTATTTCCCTGAGCCAGTGACAGTGACCTGGAACTCTGGATCC

CTGTCCAGCGGTGTGCACACCTTCCCAGCAAGCTTGGCGTAATCATGGTC

ATAGCTGTTTCCTGTGTGAAATTGTTATCCGCTCACAATTCCACACAACA

TACGAGCCGGAAGCATAAAGTGTAAAGCCTGGGGGTGCCTAATGAGTGAG

CTAACTCACATTAATTGCGTTGCGCTCACTGCCCGCTTTCCAGTCGGGAA
```

-continued

```
ACCTGTCGTGCCAGCTGCATTAATGAATCGGCCAACGCGCGGGGAGAGGC

GGTTTGCGTATTGGGCGCTCTTCCGCTTCCTCGCTCACTGACTCGCTGCG

CTCGGTCGTTCGGCTGCGGCGAGCGGTATCAGCTCACTCAAAGGCGGTAA

TACGGTTATCCACAGAATCAGGGGATACGCAGAAAGAACATGTGAGCAA

AGGCCAGCAAAAGCCAGGGACCGTAAAAGCCGCGTTGCTGCGTTTTCATA

GGCTCCGCCCCCCTGACGAGCATCACAAAATCGACGCCTCAGTCAGAAGG
```

The underlined portion in SEQ ID NO:5 is the nucleotide sequence of the heavy variable region, whereas the remaining sequence is vector sequence. The underlined portion is SEQ ID NO:6

```
(GAGGTTCAGCTGCAGCAGTCTGGGGCAGAGCTTGTGAGGTCAGGGGCCT

CAGTCAACTTGTCCTGCACAGCTTCTGGCTTCAACATTAAAGACTACTAT

ATACACTGGGTGAAGCAGAGGCCTGAACGGGGCCTGGAGTGGATTGGATG

GATTGATCCTGAGAATGGTGATACTGAATATGCCCCGGAGTTCCAGGGCA

AGGCCTCTATGACTGCAGACACATCCTCCAACACAGCCTACCTGCAGCTC

AGCAGCCTGACATCTGAGGACACTGCCGTCTATTACTGTAAGCGAGGGGA

CTGGGGCCAAGGGACTCTGGTCACTGTCTCTGCAG),
``` and protein encoded by SEQ ID NO: 6 is as follows:
```
                                    (SEQ ID NO: 7)
EVQLQQSGAELVRSGASVNLSCTASGFNIKDYYIHWVKQRPERGLEWIGW

IDPENGDTEYAPEFQGKASMTADTSSNTAYLQLSSLTSEDTAVYYCKRGD

WGQGTLVTVSA
```

One Example of a VH Sequence in the pRACE Vector is as Follows:
Raw Sequences for VH in pRACE are as Follows:

```
                                    (SEQ ID NO: 22)
GGTTGGTATCAACGCAGAGTACATGGGGACATATGAACACTGTTTTCTCT

ACAGTCACTGAATCTCAAGGTCCTTACAATGAAATGCAGCTGGGTCATCT

TCTTCCTGATGGCAGTGGTTATAGGAATCAATTCAGAGGTTCAGCTGCAG

CAGTCTGGGGCAGAGCTTGTGAGGTCAGGGGCCTCAGTCAACTTGTCCTG

CACAGCTTCTGGCTTCAACATTAAAGACTACTATATACACTGGGTGAAGC

AGAGGCCTGAACGGGGCCTGGAGTGGATTGGATGGATTGATCCTGAGAAT

GGTGATACTGAATATGCCCCGGAGTTCCAGGGCAAGGCCTCTATGACTGC

AGACACATCCTCCAACACAGCCTACCTGCAGCTCAGCAGCCTGACATCTG

AGGACACTGCCGTCTATTACTGTAAGCGAGGGGACTGGGGCCAAGGGACT

CTGGTCACTGTCTCTGCAGCCAAAACGACACCCCCATCTGTCTATCCACT

GGCCCCTGGATCTGCTGCCCAAACTAACTCCATGGTGACCCTGGGATGAA

GCTTGGCGTAATCATGGTCATAGCTGTTTCCTGTGTGAAATTGTTATCCG

CTCACAATTCCACACAACATACGAGCCGGAAGCATAAAGTGTAAAGCCTG

GGGTGCCTAATGAGTGAGCTAACTCACATTAATTGCGTTGCGCTCACTGC

CCGCTTTCCAGTCGGGAAACCTGTCGTGCCAGCTGCATTAATGAATCGGC

CAACGCGCGGGGAGAGGCGGTTTGCGTATTGGGCGCTCTTCCGCTTCCTC

GCTCACTGACTCGCTGCGCTCGGTCGTTCGGCTGCGGCGAGCGGTATCAG
```

-continued

```
CTCACTCAAAGGCGGTAATACGGTTATCCACAGAATCAGGGGATAACGCA

GGAAAGAACATGTGAGCAAAAGCCAGCAAAAGGCCAGGAACCGTAAAAAG

GCCGCGTTGCTGGCGTTTTCCATAGGCTCCGCCCCCTGACGAGCATCACA

AAAATCGACGCTCAGTCAGAGGTGGCGAAACCCGACAGGACTATAAGATA

CAGGCGTTTCCCCTGGAGCTCCTCGTGCGCTCTCTGTCGACCTGCGCTAC
```

Complementarity-Determining Regions (CDR) for SEQ ID NO:7:
The Heavy Chain CDR Sequences in SEQ ID NO:7 are as Follows:

```
CDR1 is GFNIKDYY (SEQ ID NO: 8) which is encoded
by ggcttcaacattaaagactactat (SEQ ID NO: 9).

CDR2 is IDPENGDT (SEQ ID NO: 10) which is encoded
by attgatcctgagaatggtgatact (SEQ ID NO: 11).

CDR3 is KRGD (SEQ ID NO: 12) which is encoded by
aagcgaggggac (SEQ ID NO: 13)
```

Below describes for clone VL (K): the variable region light (VL) sequences.

```
                                    (SEQ ID NO: 14)
AGCTGAGTATCAACGCAGAGTACATGGGGACTGATCAGTCTCCTCAGGCT

GTCTCCTCAGGTTGCCTCCTCAAAATGAAGTTGCCTGTTAGGCTGTTGGT

GCTGATGTTCTGGATTCCTGCTTCCAGCAGTGATGTTTTGATGACCCAAA

CTCCACTCTCCCTGCCTGTCAGTCTTGGAGATCAAGCCTCCATCTCTTGC

AGATCTAGTCAGAGCATTGTACATAGTAATGGAAACACCTATTTAGAATG

GTTCCTGCAGAAACCAGGCCAGTCTCCAAAGCTCCTGATCTACAAAGTTT

CCAACCGATTTTCTGGGGTCCCAGACAGGTTCAGTGGCAGTGGATCAGGG

ACAGATTTCACACTCAAGATCAGCAGAGTGGAGGCTGAGGATCTGGGAGT

TTATTACTGCTTTCAAGGTTCACATGCTCCATTCACGTTCGGCTCGGGGA

CAGAGTTGGAAATAAAACGGGCTGATGCTGCACCAACTGTATCCATCTTC

CCACCATCCAGTGAGCAAGCTTGGCGTAATCATGGTCATAGCTGTTTCCT

GTGTGAAATTGTTATCCGCTCACAATTCCACACAACATACGAGCCGGAAG

CATAAAGTGTAAAGCCTGGGGTGCCTAATGAGTGAGCTAACTCACATTAA

TTGCGTTGCGCTCACTGCCCGCTTTCCAGTCGGGAAACCTGTCGTGCCAG

CTGCATTAATGAATCGGCCAACGCGCGGGGAGAGGCGGTTTGCGTATTGG

GGCGCTCTTCCGCTTCCTCGCTCACTGACTCGCTGCGCTCGGTCGTTCGG

CTGCGGCGAGCGGTATCAGCTCACTCAAAGGCGGTAATACGGTTATCCAC

AGAATCAGGGGATAACGCAGAAAGAACATGTGAGCAAAAGGCCAGCAAAA

GGCCAGGAACCGTAAAAAGGCCGCGTTGCTGGCGTTTTTCCATAGGCTCC

GCCCCCTGACGAGCATCACAAAATCGACGCTCAAGTCAGAGGTGGCGAAA

CCCGACAGGACTATAAGATACCAGGCGTTTCCCCTGAAGCTCCCTCGTG

CGCTCTCTGTTCGACCCTGCGCTACGATACTGTCGCTTCTCCTTCGGAGC
```

The underlined portion in SEQ ID NO:14 is the nucleotide sequence of the light variable region, whereas the remaining sequence is vector sequence. The underlined portion is SEQ ID NO:15

(GATGTTTTGATGACCCAAACTCCACTCTCCCTGCCTGTCAGTCTTGGAG

ATCAAGCCTCCATCTCTTGCAGATCTAGTCAGAGCATTGTACATAGTAAT

GGAAACACCTATTTAGAATGGTTCCTGCAGAAACCAGGCCAGTCTCCAAA

GCTCCTGATCTACAAAGTTTCCAACCGATTTTCTGGGGTCCCAGACAGGT

TCAGTGGCAGTGGATCAGGGACAGATTTCACACTCAAGATCAGCAGAGTG

GAGGCTGAGGATCTGGGAGTTTATTACTGCTTTCAAGGTTCACATGCTCC

ATTCACGTTCGGCTCGGGGACAGAGTTGGAAATAAAAC), and protein encoded by SEQ ID NO: 15 is as
follows:

(SEQ ID NO: 16)
DVLMTQTPLSLPVSLGDQASISCRSSQSIVHSNGNTYLEWFLQKPGQSPK

-continued
LLIYKVSNRFSGVPDRFSGSGSGTDFTLKISRVEAEDLGVYYCFQGSHAP

FTFGSGTELEIK

The Light Chain CDR Sequences in SEQ ID NO:16 are as
Follows:

CDR1 is QSIVHSNGNTY (SEQ ID NO: 17) that is
encoded by cagagcattgtacatagtaatggaaacacctat (SEQ
ID NO: 18).

CDR2 is KVS that is encoded by aaagtttcc (SEQ ID
NO: 19).

CDR3 is FQGSHAPFT (SEQ ID NO:20) that is
encoded by tttcaaggttcacatgctccattcacg (SEQ ID NO:
21).

LA1 Antibody

```
Sequences for Hybridoma: LA-1 (isotype: IgG1, kappa)
VL: mouse kappa
VL Consensus Sequence starting from Frame 1 (FR1,), showing + strand
VL Nucleotide sequence:
                                              (SEQ ID NO: 28)
GACATTGTGATGACCCAGTCTCAAAAATTCATGTCCACATCAGTAGGAGACA
GGGTCAGCGTCACCTGCAAGGCCAGTCAGAATGTGGGTACTAACGTAGCCTGGTAT
CAACAGAAACCAGGGCAATCTCCCAAAGCACTGATTCACTCGGCATCCTACCGGTA
CAGTGGAGTCCCTGATCGCTTCACAGGCAGTGGATCTGGGACAGATTTCACTCTCAC
CATCAGCAATGTGCAGTCTGAAGACTTGGCAGAGTATTTCTGTCAGCAATATAACAG
CTATCCGCTCACGTTCGGTGCTGGGACCAAGCTGGAGCTGAAA VL Amino acid sequence:
                                              (SEQ ID NO: 29)
DIVMTQSQKFMSTSVGDRVSVTCKASQNVGTNVAWYQQKPGQSPKALIHSASY
RYSGVPDRFTGSGSGTDFTLTISNVQSEDLAEYFCQQYNSYPLTFGAGTKLELK CDR1:
                                              (SEQ ID NO: 30)
QNVGTN
(DNA sequence: CAGAATGTGGGTACTAAC; (SEQ ID NO: 31))

CDR2: SAS (DNA sequence: TCGGCATCC; (SEQ ID NO: 32))

CDR3:
                                              (SEQ ID NO: 33)
QQYNSYPLT
(DNA sequence: CAGCAATATAACAGCTATCCGCTCACG; (SEQ ID NO: 34))

Raw sequences for VL(κ) in pRACE
                                              (SEQ ID NO: 35)
CCCAAACTAAAATAGGGCAGCAGTGGTATCAACGCAGAGTACATGGGGGAA
ATACATCAGATCAGCATGGGCATCGAGATGGAGTCACAGACTCAGGTCTTTGTTTAC
ATGTTGCTGTGGTTGTCTGGTGTTGATGGAGACATTGTGATGACCCAGTCTCAAAAA
TTCATGTCCACATCAGTAGGAGACAGGGTCAGCGTCACCTGCAAGGCCAGTCAGAA
TGTGGGTACTAACGTAGCCTGGTATCAACAGAAACCAGGGCAATCTCCCAAAGCAC
TGATTCACTCGGCATCCTACCGGTACAGTGGAGTCCCTGATCGCTTCACAGGCAGTG
GATCTGGGACAGATTTCACTCTCACCATCAGCAATGTGCAGTCTGAAGACTTGGCAG
AGTATTTCTGTCAGCAATATAACAGCTATCCGCTCACGTTCGGTGCTGGGACCAAGC
TGGAGCTGAAACGGGCTGATGCTGCACCAACTGTATCCATCTTCCCACCATCCAGTG
AGCAAGCTTGGCGTAATCATGGTCATAGCTGTTTCCTGTGTGAAATTGTTATCCGCTC
ACAATTCCACACAACATACGAGCCGGAAGCATAAAGTGTAAAGCCTGGGGTGCCTA
ATGAGTGAGCTAACTCACATTAATTGCGTTGCGCTCACTGCCCCGCTTTCCAGTCGGG
AAACCTGTCGTGCCAGCTGCATTAATGAATCGGCCAACGCGCGGGGAGAGGCGGTT
TGCGTATTGGGCGCTCTTCCGCTTCCTCGCTCACTGACTCGCTGCGCTCGGTCGTTC
GGCTGCGGCGAGCGGTATCAGCTCACTCAAAGGCGGTAATACGGTTATCCACAGAA
TCAGGGGATAACGCACGAAAGAACATGTGAGCAAAAGGCCAGCAAAGGCCAGGA
ACCGTAAAAAGGGCGCGTTGCTGGCGTTTTTCCATAGGCTCCGCCCCCTGACAGCAT
CACAAAATCGACGCTCAGTCAAGGTGGCGAATCCGGACAGGACTATAAGAATACCA
GGCGTTTCCCCATGGAAGTTCCTCGGGCGTCCTTCCTGTCCCGACCCTGCCGCTACC
GGAATACCTGGTCGCCTTTCTCCCCATCC VH: mouse IgG1
VH Consensus Sequence starting from Frame 1 (FR1), showing + strand
VH Nucleotide sequence:
                                              (SEQ ID NO: 36)
GAGGTCCAGCTGCAACAGTCTGGACCTGAGCTGGTGAAGCCTGGGGCTTCAG
TGAAGATATCCTGCAAGACTTCTGGATACACATTCACTGAAGACACCATGCACTGGG
```

-continued
```
TGAAGCAGAGCCATGGAAAGAGCCTTGAGTGGATTGGAGGTATTAATCCTAACAAG
GGTGGTACTAGCTACAACCAGAAGTTCAAGGACAAGGCCACATTGACTGTAGACAA
GTCCTCCAGCACAGCCTACATGGAGCTCCGCAGCCTGACATCTGAGGATTCTGCAGT
CTATTACTGTGCTACGCTGGTAGACTACTGGGGCCAAGGCACCACTCTCACAGTCTC
CTCA
```

VH Amino acid sequence:

(SEQ ID NO: 37)
```
EVQLQQSGPELVKPGASVKISCKTSGYTFTEDTMHWVKQSHGKSLEWIGGINPNKGGTS
YNQKFKDKATLTVDKSSSTAYMELRSLTSEDSAVYYCATLVDYWGQGTTLTVSS
```

CDR1:

(SEQ ID NO: 38)
```
GYTFTEDT
```
(DNA sequence: GGATACACATTCACTGAAGACACC; (SEQ ID NO: 39))

CDR2:

(SEQ ID NO: 40)
```
INPNKGGT
```
(DNA sequence: ATTAATCCTAACAAGGGTGGTACT; (SEQ ID NO: 41))

CDR3:

(SEQ ID NO: 42)
```
ATLVDY;
```
(DNA sequence: GCTACGCTGGTAGACTAC; (SEQ ID NO: 43))

Raw sequences for VH in pRACE (SEQ ID NO: 44)
```
TCATTACTACTATAGGGGCAAGCAGTGGTATCAACGCAGAGTACATGGGGAT
ATGTCCAATGTCCTCTCCTCAGACACTGAACACACTGACTCTAACCATGGGATGGAG
CTGGATCTTTCTCTTTCTCCTGTCAGGAACTGCAGGTGTCCTCTCTGAGGTCCAGCTG
CAACAGTCTGGACCTGAGCTGGTGAAGCCTGGGGCTTCAGTGAAGATATCCTGCAA
GACTTCTGGATACACATTCACTGAAGACACCATGCACTGGGTGAAGCAGAGCCATG
GAAAGAGCCTTGAGTGGATTGGAGGTATTAATCCTAACAAGGGTGGTACTAGCTAC
AACCAGAAGTTCAAGGACAAGGCCACATTGACTGTAGACAAGTCCTCCAGCACAGC
CTACATGGAGCTCCGCAGCCTGACATCTGAGGATTCTGCAGTCTATTACTGTGCTAC
GCTGGTAGACTACTGGGGCCAAGGCACCACTCTCACAGTCTCCTCAGCCAAAACGA
CACCCCCATCTGTCTATCCACTGGCCCCTGGATCTGCTGCCCAAACTAACTCCATGG
TGACCCTGGGATGCCTGGTCAAGGGCTATTTCCCTGAGCCAGTGACAGTGACCTGGA
ACTCTGGATCCCAAGCTTGGCGTAATCATGGTCATAGCTGTTTCCTGTGTGAAATTGT
TATCCGCTCACAATTCCACACAACATACGAGCCGGAAGCATAAAGTGTAAAGCCTG
GGGTGCCTAATGAGTGAGCTAACTCACATTAATTGCGTTGCGCTCACTGCCCGCTTT
CCAGTCGGGAAACCTGTCGTGCCAGCTGCATTAATGAATCGGCCAACGCGCGGGGA
GAGGCGGTTTGCGTATTGGGCGCTCTTCCGCTTCCTCGCTCACTGACTCGCTGCGCTC
GGTCGTTCGGCTGCGGGCGAGCGGTATCAGCTCACTCAAAGGCGGTAATACGGTTAT
CCACAGAATCAGGGGATAACGCAGGAAAGAACATGTGAGCAAAAGGCCAGCAAAA
GGCCAGGACCCGTAAAAAGGCCGCGTTGCTGGCGTTTTCCAATAGCCTCCGCCCCCC
CTGACGAGCATCACAAAAAATCGACGCT
```

BM7 Antibody
  Hybridoma: BM7 (isotype: IgG1, kappa)

VL: mouse kappa
VL Consensus Sequence starting from Frame 1 (FR1), showing + strand
VL Nucleotide sequence:

(SEQ ID NO: 45)
```
GATGTTGTGATGACCCAAACTCCAGTCTCCCTGCCTGTCAGTCTTGGAGATCA
AGCCTCCATCTCTTGCAGATCTACTCAGAGCCTTGTACACAGTAATGGACACACCTA
TTTACATTGGTACCTGCAGAAGCCAGGCCAGTCTCCTAAGCTCCTGATCTACAAAGT
TTCCAACCGATTTTCTGGGGTCCCAGACAGGTTCAGTGGCACTGGATCAGGGACAGA
TTTCACACTCAAGATCAGCAGAGTGGAGGCTGAGGATCTGGGAGTTTATTTCTGCTC
TCAAAGTACACATGTTCCGTACACGTTCGGAGGGGGGACCAAGCTGGAAATAAAA
```

VL Amino acid sequence:

(SEQ ID NO: 46)
```
DVVMTQTPVSLPVSLGDQASISCRSTQSLVHSNGHTYLHWYLQKPGQSPKLLIYKVSNR
FSGVPDRFSGTGSGTDFTLKISRVEAEDLGVYFCSQSTHVPYTFGGGTKLEIK
```

CDR1:

(SEQ ID NO: 47)
```
QSLVHSNGHTY
```
(DNA sequence: CAGAGCCTTGTACACAGTAATGGACACACCTAT; (SEQ
ID NO: 48))

CDR2: KVS (DNA sequence: AAAGTTTCC; (SEQ ID NO: 49))

CDR3:

(SEQ ID NO: 50)

SQSTHVPYT
(DNA sequence: TCTCAAAGTACACATGTTCCGTACACG (SEQ ID NO: 51))

Raw sequences for VL(κ) in pRACE (SEQ ID NO: 52)

GGCAGCAGTGGTATCAACGCAGAGTACATGGGGGATCAGTCTCCTCAGGCTG
TCTCCTCAGGCTTGCCTCCTCAAAATGAAGTTGCCTGTTAGGCTGTTGGTGCTGATGT
TCTGGATTCCTGCTTCCAGCAGTGATGTTGTGATGACCCAAACTCCAGTCTCCCTGCC
TGTCAGTCTTGGAGATCAAGCCTCCATCTCTTGCAGATCTACTCAGAGCCTTGTACA
CAGTAATGGACACACCTATTTACATTGGTACCTGCAGAAGCCAGGCCAGTCTCCTAA
GCTCCTGATCTACAAAGTTTCCAACCGATTTTCTGGGGTCCCAGACAGGTTCAGTGG
CACTGGATCAGGGACAGATTTCACACTCAAGATCAGCAGAGTGGAGGCTGAGGATC
TGGGAGTTTATTTCTGCTCTCAAAGTACACATGTTCCGTACACGTTCGGAGGGGGGA
CCAAGCTGGAAATAAAACGGGCTGATGCTGCACCAACTGTATCCATCTTCCCACCAT
CCAGTGAGCAAGCTTGGCGTAATCATGGTCATAGCTGTTTCCTGTGTGAAATTGTTA
TCCGCTCACAATTCCACACAACATACGAGCCGGAAGCATAAAGTGTAAAGCCTGGG
GTGCCTAATGAGTGAGCTAACTCACATTAATTGCGTTGCGCTCACTGCCCGCTTTCC
AGTCGGGAAACCTGTCGTGCCAGCTGCATTAATGAATCGGCCAACGCGCGGGGAGA
GGCGGTTTGCGTATTGGGCGCTCTTCCGCTTCCTCGCTCACTGACTCGCTGCGCTCGG
TCGTTCGGCTGCGGCGAGCGGTATCAGCTCACTCAAAGGCGGTAATACGGTTATCCA
CAGAATCAGGGGATAACGCAGGAAAGAACATGTGAGCAAAAGGCCAGCAAAAGGC
CAGGAACCGTAAAAAGGCCGCGTTGCTGGCGTTTTTCCATAGGCTCCGCCCCCCCTG
ACGAGCATCACAAAAATCGACGCTCAAGTCANAGGTGGCGAAACCCGACAGGACTA
TNAAGATACCAGGCGTTTCCCCCTGGAAGCTCCCTCGTGCGCTCTCCTGNTCCNACC
TGCCGCTTACCGNAAACTGTCCGCN

VH: mouse IgG1
VH Consensus Sequence starting from Frame 1 (FR1,), showing + strand
VH Nucleotide sequence:

(SEQ ID NO: 53)

CAAGTTACTCTAAAAGAGTCTGGCCCTGGGATATTGAAGCCCTCACAGACCC
TCAGTCTGACTTGTTCTTTCTCTGGGTTTTCACTGAGCACTTCTGGTGTGGGTGTAGG
CTGGATTCGTCAGCCTTCAGGGAAGGGTCTGGAGTGGCTGGCACACATTTGGTGGGA
TGATGATGAGTACTATAACCCATCCCTGAAGAGCCAGCTCACAATCTCCAAGGATAC
CTCCAGAAACCAGGTATTCCTCAAGATCACCAGTGTGGACACTTCAGATACTGCCAC
TTACTACTGTGCTCGCCGATACTACGGGGACGCTATGGACTACTGGGGTCAAGGAAC
CGCAGTCACCGTCTCCTCC

VH Amino acid sequence:

(SEQ ID NO: 54)

QVTLKESGPGILKPSQTLSLTCSFSGFSLSTSGVGVGWIRQPSGKGLEWLAHIWWDDDE
YYNPSLKSQLTISKDTSRNQVFLKITSVDTSDTATYYCARRYYGDAMDYWGQGTAVTV
SS

CDR1:

(SEQ ID NO: 55)

GFSLSTSGVG
(DNA sequence: GGGTTTTCACTGAGCACTTCTGGTGTGGGT; (SEQ ID NO: 56))

CDR2:

(SEQ ID NO: 57)

IWWDDDE
(DNA sequence: ATTTGGTGGGATGATGATGAG (SEQ ID NO: 58))

CDR3:

(SEQ ID NO: 59)

ARRYYGDAMDY
(DNA sequence: GCTCGCCGATACTACGGGGACGCTATGGACTAC (SEQ ID NO: 60))

Raw sequences for VH in pRACE (SEQ ID NO: 61)

TCATTAATAAGGGGGGCAAGCAGTGGTATCAACGCAGAGTACATGGGGACA
CAAGTGTGCAGACATGGACAGGCTTACTTCTTCATTCCTGCTGCTGATTGTCCCTGCA
TATGTCTTGTCCCAAGTTACTCTAAAAGAGTCTGGCCCTGGGATATTGAAGCCCTCA
CAGACCCTCAGTCTGACTTGTTCTTTCTCTGGGTTTTCACTGAGCACTTCTGGTGTGG
GTGTAGGCTGGATTCGTCAGCCTTCAGGGAAGGGTCTGGAGTGGCTGGCACACATTT
GGTGGGATGATGATGAGTACTATAACCCATCCCTGAAGAGCCAGCTCACAATCTCCA
AGGATACCTCCAGAAACCAGGTATTCCTCAAGATCACCAGTGTGGACACTTCAGATA
CTGCCACTTACTACTGTGCTCGCCGATACTACGGGGACGCTATGGACTACTGGGGTC
AAGGAACCGCAGTCACCGTCTCCTCCGCCAAAACGACACCCCCATCGTCTATCCAC
TGGCCCCTGGATCTGCTGCCCAAACTAACTCCATGGTGACCCTGGGATGCCTGGTCA
AGGGCTATTTCCCTGAGCCAGTGACAGTGACCTGGAACTCTGGATCCCAAGCTTGGC
GTAATCATGGTCATAGCTGTTTCCTGTGTGAAATTGTTATCCGCTCACAATTCCACAC
AACATACGAGCCGGAAGCATAAAGTGTAAAGCCTGGGGTGCCTAATGAGTGAGCTA
ACTCACATTAATTGCGTTGCGCTCACTGCCCGCTTTCCAGTCGGGAAACCTGTCGTG
CCAGCTGCATTAATGAATCGGCCAACGCGCGGGGAGAGGCGGTTTGCGTATTGGGC
GCTCTTCCGCTTCCTCGCTCACTGACTCGCTGCGCTCGGTCGTTCGGCTGCGGCGAGC
GGTATCAGCTCACTCAAAGGCGGTAATACGGTTATCCACAGAATCAGGGGATACGC

-continued
AGAAGAACATGTGAGCAAAAGGCCAGCAAAAGGCCAGGAACCGTAAAAGGCCGCG
TTGCTGGCGTTTTTCCATAGGCTCGCCCCCCTGACGAGCATCACAAAAAATCGACGC
TCAGTCAGAGGTGGCGAAACCGAC Embodiments of the disclosure comprise compositions that comprise antibodies or functionally active fragments thereof that bind SEQ ID NO:1, SEQ ID NO:2, and/or SEQ ID NO:4. Although the antibodies may be of any kind, in specific cases the antibody is a monoclonal antibody. Also encompassed herein are functionally active fragments thereof such as a single-chain variable fragment (scFv), Fv, Fab, and F(ab')2. The antibody or functionally active fragment thereof may or may not be humanized.

Aspects of the disclosure relate to an antibody or an antigen-binding portion thereof, the antibody comprising three heavy chain CDRs (CDR-H) and three light chain CDRs (CDR-L), wherein the antibody is characterized by one or more of the following characteristics: CDR-H1 comprises an amino acid sequence as set forth in SEQ ID NO: 8 (GFNIKDYY), CDR-H2 comprises the amino acid sequence as set forth in SEQ ID NO: 10 (IDPENGDT), CDR-H3 comprises the amino acid sequence as set forth in SEQ ID NO: 12 (KRGD), CDR-L1 comprises the amino acid sequence as set forth in SEQ ID NO: 17 (QSIVHSNG-NTY), CDR-L2 comprises the amino acid sequence of KVS, and CDR-L3 comprises the amino acid sequence as set forth in SEQ ID NO: 20 (FQGSHAPFT); and wherein said antibody or antigen-binding portion thereof binds to BST2, including the long form of BST2. In particular embodiments, the antibody is characterized by having all of the above-referenced characteristics. In some embodiments, the antibody comprises an antigen binding variable region comprising the amino acid sequence of CDR-H1 of SEQ ID NO:8 or an amino acid sequence with at least 80, 85, 90, 95, 96, 97, 98, or 99% sequence identity to SEQ ID NO:8. In some embodiments, the antibody comprises an antigen binding variable region comprising the amino acid sequence of CDR-H2 of SEQ ID NO:10 or an amino acid sequence with at least 80, 85, 90, 95, 96, 97, 98, or 99% sequence identity to SEQ ID NO:10. In some embodiments, the antibody comprises an antigen binding variable region comprising the amino acid sequence of CDR-H3 of SEQ ID NO:12 or an amino acid sequence with at least 80, 85, 90, 95, 96, 97, 98, or 99% sequence identity to SEQ ID NO:12. In some embodiments, the antibody comprises an antigen binding variable region comprising the amino acid sequence of CDR-L1 of SEQ ID NO:17 or an amino acid sequence with at least 80, 85, 90, 95, 96, 97, 98, or 99% sequence identity to SEQ ID NO:17. In some embodiments, the antibody comprises an antigen binding variable region comprising the amino acid sequence of CDR-L3 of SEQ ID NO:20 or an amino acid sequence with at least 80, 85, 90, 95, 96, 97, 98, or 99% sequence identity to SEQ ID NO:20.

Aspects of the disclosure relate to an antibody or an antigen-binding portion thereof, the antibody comprising three heavy chain CDRs (CDR-H) and three light chain CDRs (CDR-L), wherein the antibody is characterized by one or more of the following characteristics: CDR-H1 comprises an amino acid sequence as set forth in SEQ ID NO: 38 (GYTFTEDT), CDR-H2 comprises the amino acid sequence as set forth in SEQ ID NO: 40 (INPNKGGT), CDR-H3 comprises the amino acid sequence as set forth in SEQ ID NO: 42 (ATLVDY), CDR-L1 comprises the amino acid sequence as set forth in SEQ ID NO: 30 (QNVGTN), CDR-L2 comprises the amino acid sequence of SAS, and CDR-L3 comprises the amino acid sequence as set forth in SEQ ID NO: 33 (QQYNSYPLT); and wherein said antibody or antigen-binding portion thereof binds to BST2, including the long form of BST2. In particular embodiments, the antibody is characterized by having all of the above-referenced characteristics. In some embodiments, the antibody comprises an antigen binding variable region comprising the amino acid sequence of CDR-H1 of SEQ ID NO:38 or an amino acid sequence with at least 80, 85, 90, 95, 96, 97, 98, or 99% sequence identity to SEQ ID NO:38. In some embodiments, the antibody comprises an antigen binding variable region comprising the amino acid sequence of CDR-H2 of SEQ ID NO:40 or an amino acid sequence with at least 80, 85, 90, 95, 96, 97, 98, or 99% sequence identity to SEQ ID NO:40. In some embodiments, the antibody comprises an antigen binding variable region comprising the amino acid sequence of CDR-H3 of SEQ ID NO:42 or an amino acid sequence with at least 80, 85, 90, 95, 96, 97, 98, or 99% sequence identity to SEQ ID NO:42. In some embodiments, the antibody comprises an antigen binding variable region comprising the amino acid sequence of CDR-L1 of SEQ ID NO:30 or an amino acid sequence with at least 80, 85, 90, 95, 96, 97, 98, or 99% sequence identity to SEQ ID NO:30. In some embodiments, the antibody comprises an antigen binding variable region comprising the amino acid sequence of CDR-L3 of SEQ ID NO:33 or an amino acid sequence with at least 80, 85, 90, 95, 96, 97, 98, or 99% sequence identity to SEQ ID NO:33.

Aspects of the disclosure relate to an antibody or an antigen-binding portion thereof, the antibody comprising three heavy chain CDRs (CDR-H) and three light chain CDRs (CDR-L), wherein the antibody is characterized by one or more of the following characteristics: CDR-H1 comprises an amino acid sequence as set forth in SEQ ID NO: 55 (GFSLSTSGVG), CDR-H2 comprises the amino acid sequence as set forth in SEQ ID NO: 57 (IWWDDDE), CDR-H3 comprises the amino acid sequence as set forth in SEQ ID NO: 59 (ARRYYGDAMDY), CDR-L1 comprises the amino acid sequence as set forth in SEQ ID NO: 47 (QSLVHSNGHTY), CDR-L2 comprises the amino acid sequence of KVS, and CDR-L3 comprises the amino acid sequence as set forth in SEQ ID NO: 50 (SQSTHVPYT); and wherein said antibody or antigen-binding portion thereof binds to BST2, including the long form of BST2. In particular embodiments, the antibody is characterized by having all of the above-referenced characteristics. In some embodiments, the antibody comprises an antigen binding variable region comprising the amino acid sequence of CDR-H1 of SEQ ID NO:55 or an amino acid sequence with at least 80, 85, 90, 95, 96, 97, 98, or 99% sequence identity to SEQ ID NO:55. In some embodiments, the antibody comprises an antigen binding variable region comprising the amino acid sequence of CDR-H2 of SEQ ID NO:57 or an amino acid sequence with at least 80, 85, 90, 95, 96, 97, 98, or 99% sequence identity to SEQ ID NO:57. In some embodiments, the antibody comprises an antigen binding variable region comprising the amino acid sequence of CDR-H3 of SEQ ID NO:59 or an amino acid sequence with at least 80, 85, 90, 95, 96, 97, 98, or 99% sequence identity to SEQ ID NO:59. In some embodiments, the antibody comprises an antigen binding variable region comprising the amino acid sequence of CDR-L1 of SEQ ID NO:47 or an amino acid sequence with at least 80, 85, 90, 95, 96, 97, 98, or 99% sequence identity to SEQ ID NO:47. In some embodiments, the antibody comprises an antigen binding variable region comprising the amino acid sequence of CDR-L3 of SEQ ID NO:50 or an amino acid sequence with at least 80, 85, 90, 95, 96, 97, 98, or 99% sequence identity to SEQ ID NO:50.

In some embodiments, the variable region comprises an amino acid sequence with at least 70% sequence identity to one or more of SEQ ID NOS:7, 37, 54, 16, 46, or 29. In some embodiments, the variable region comprises an amino acid sequence with at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to one or more of SEQ ID NOS:7, 37, 54, 16, 46, or 29. In some embodiments, the variable region comprises the amino acid sequence of one of SEQ ID NOS: 7, 37, 54, 16, 46, or 29, including in at least some cases one or more of SEQ ID NOS: 7, 37, 54, 16, 46, or 29. In some embodiments, an engineered antigen receptor of any kind comprises an amino acid sequence with at least 70% sequence identity to one or more of SEQ ID NOS:7 and 16. In some embodiments, the engineered antigen receptor comprises an amino acid sequence with at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to one of SEQ ID NOS: 7, 37, 54, 16, 46, or 29.

A CDR may comprise 1, 2, 3, 4, 5, 6, 7, 8, 9, 10, 11, 12, 13, 14, 15, 16, 16, 18, 19, 20, 21, 22, 23, or more contiguous amino acid residues (or any range derivable therein) flanking one or both sides of a particular CDR sequence in the context of the variable region of the heavy chain and/or light chain of the BST2 antibody polypeptide; therefore, there may be one or more additional amino acids at the N-terminal or C-terminal end of a particular CDR sequence, such as those shown in the variable regions of SEQ ID NOS: 7, 37, 54, 16, 46, or 29. Alternatively, or in combination, a CDR may also be a fragment of a CDR described herein and may lack at least 1, 2, 3, 4, or 5 amino acids from the C-terminal or N-terminal end of a particular CDR sequence.

Examples of Antigen Binding Regions (ABR, Also Referred to as CDR)

In alternative embodiments to description elsewhere herein, the ABR for LA5/H9 hybridoma are as follows:

```
For VH::
                                (SEQ ID NO: 23)
ABR1: FNIKDYYIH (27-35)

(SEQ ID NO: 24)
ABR2: WIGWIDPENGDTEYA (47-61)

(SEQ ID NO: 12)
ABR3: KRGD (97-100)

For VL(K)::
                                (SEQ ID NO: 25)
BR1: QSIVHSNGNTYLE (27-39)

(SEQ ID NO: 26)
ABR2: LLIYKVSNRFS (51-61)

(SEQ ID NO: 27)
ABR3: FQGSHAPF (94-101)
```

As described elsewhere herein, the LA5 antibody was analyzed after purification. KD Affinity was performed by OCTET platform, capturing Fc portion to anti-mouse antibodies biosensors and using the full-length BST2 protein.

KD=4.61 nM. Binding to primary cells was performed by FACS on lineage B cells, including a couple of multiple myeloma cell lines (MM1 and U266) and a surrogate normal transformed B cell line (B-LCL). Although LA5 antibody did not selectively bind to MM vs surrogate normal B cell, it demonstrated that MM exclusively expressed long isoform, since it was compared to a commercial available clone (26F8) that recognizes all the three isoforms (short, medium and long). The percentage of stained cells was around 98% in both surrogate normal and MM cells. To prove specificity to tumor cells, further studies are performed using a proper normal cell control.

In immunohistochemistry staining of human infiltrating ductal breast carcinoma tissues, LA5 differentially recognized only tumor cells and not surrounding normal duct and acinus. Thus, the LA5 antibody and other antibodies encompassed herein in certain embodiments serve as a diagnostic tool in breast cancer and in at least some cases as a therapeutic tool, including for metastatic cancer, in some embodiments.

In some embodiments, any of the compositions described herein are comprised in a pharmaceutical composition that is formulated for parenteral administration, intravenous injection, intramuscular injection, inhalation, or subcutaneous injection. In some embodiments, any composition is comprised in a liposome, lipid-containing nanoparticle, or in a lipid-based carrier. In some embodiments, the compositions of the disclosure are formulated as a vaccine. In some embodiments, the composition further comprises an adjuvant.

In some embodiments, the compositions of the disclosure are formulated as a vaccine or immunogenic composition. In some embodiments, the compositions and methods of the disclosure provide for prophylactic therapies to prevent cancer, reduce the severity of cancer, delay the onset of cancer, and so forth. In some embodiments, the composition further comprises an adjuvant. Adjuvants are known in the art and include, for example, TLR agonists and aluminum salts.

IV. Pharmaceutical Compositions of Antibodies

In other embodiments there is provided a pharmaceutical composition including an antibody as described herein with a pharmaceutically acceptable carrier, diluent or excipient.

In the preparation of the pharmaceutical compositions comprising the antibodies described in the teachings herein, a variety of vehicles and excipients and routes of administration may be used, as will be apparent to the skilled artisan. Representative formulation technology is taught in, inter alia, Remington: The Science and Practice of Pharmacy, 19th Ed., Mack Publishing Co., Easton, Pa. (1995) and Handbook of Pharmaceutical Excipients, 3rd Ed, Kibbe, A. H. ed., Washington D.C., American Pharmaceutical Association (2000); hereby incorporated by reference in their entirety.

The pharmaceutical compositions will generally comprise a pharmaceutically acceptable carrier and a pharmacologically effective amount of an antibody, or mixture of antibodies.

As used herein, "pharmaceutically acceptable carrier" comprises any standard pharmaceutically accepted carriers known to those of ordinary skill in the art in formulating pharmaceutical compositions. Thus, the antibodies or peptides, by themselves, such as being present as pharmaceutically acceptable salts, or as conjugates, may be prepared as formulations in pharmaceutically acceptable diluents, for example, saline, phosphate buffer saline (PBS), aqueous ethanol, or solutions of glucose, mannitol, dextran, propylene glycol, oils (e.g., vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or as solid formulations in appropriate excipients.

The pharmaceutical compositions may further comprise one or more buffers (e.g., neutral buffered saline or phosphate buffered saline), carbohydrates (e.g., glucose, sucrose or dextrans), mannitol, proteins, polypeptides or amino acids such as glycine, antioxidants (e.g., ascorbic acid, sodium metabisulfite, butylated hydroxytoluene, butylated hydroxyanisole, etc.), bacteriostats, chelating agents such as EDTA or glutathione, adjuvants (e.g., aluminium hydroxide), solutes that render the formulation isotonic, hypotonic or weakly hypertonic with the blood of a recipient, suspending agents, thickening agents, and/or preservatives. Alternatively, compositions of the present disclosure may be formulated as a lyophilized powder.

While any suitable carrier known to those of ordinary skill in the art may be employed in the compositions of this disclosure, the type of carrier will typically vary depending on the mode of administration.

For parenteral administration, the compositions can be administered as injectable dosages of a solution or suspension of the substance in a physiologically acceptable diluent with a pharmaceutical carrier that can be a sterile liquid such as sterile pyrogen free water, oils, saline, glycerol, polyethylene glycol or ethanol. Additionally, auxiliary substances, such as wetting or emulsifying agents, surfactants, pH buffering substances and the like can be present in compositions.

Other components of pharmaceutical compositions are those of petroleum, animal, vegetable, or synthetic origin, for example, non-aqueous solutions of peanut oil, soybean oil, corn oil, cottonseed oil, ethyl oleate, and isopropyl myristate. Antibodies can be administered in the form of a depot injection or implant preparation which can be formulated in such a manner as to permit a sustained release of the active ingredient. An exemplary composition may comprise antibody at 5 mg/ml, formulated in aqueous buffer consisting of 50 mM L-histidine, 150 mM NaCl, adjusted to pH 6.0 with HCl.

Typically, the compositions are prepared as injectables, either as liquid solutions or suspensions, or solid or powder forms suitable for reconstitution with suitable vehicles, including by way of example and not limitation, sterile pyrogen free water, saline, buffered solutions, dextrose solution, etc., prior to injection. The preparation also can be emulsified or encapsulated in liposomes or micro particles such as polylactide, polyglycolide, or copolymers, or other known encapsulating technologies.

The pharmaceutical compositions described herein may be presented in unit-dose or multi-dose containers, such as sealed ampules or vials. Such containers are typically sealed in such a way to preserve the sterility and stability of the formulation until use. In general, formulations may be stored as suspensions, solutions or emulsions in oily or aqueous vehicles, as indicated above. Alternatively, a pharmaceutical composition may be stored in a lyophilized condition requiring only the addition of a sterile liquid carrier immediately prior to use.

V. Uses for Anti-BST2 Antibodies

The anti-BST2 antibodies of the disclosure have various utilities. In one embodiment, an anti-BST2 is provided for use in a method of treatment of a disease, such as cancer. The method of the disclosure may include the step of providing an antibody or BST2 antigen-binding fragment thereof, as described above, to a subject requiring said treatment. In specific embodiments, methods of the disclosure detect infiltrations of cancer cells in ectopic tissues; as a specific embodiment, methods are utilized that encompass detecting infiltrations of breast cancer cells, including malignant breast ductal carcinoma, in ectopic tissues of any kind.

Methods of immune-targeting cancer cells using antibodies or antibody fragments are well known in the art. U.S. Pat. No. 6,306,393, for instance, describes the use of anti-CD22 antibodies in the immunotherapy of B-cell malignancies, and U.S. Pat. No. 6,329,503 describes immune-targeting of cells that express serpentine transmembrane antigens. Antibodies described herein (including humanized or human monoclonal antibodies or fragments or other modifications thereof, optionally conjugated to cytotoxic or other agents) can be introduced into a patient such that the antibody binds to cancer cells and mediates the destruction of the cells and the tumor and/or inhibits the growth of the cells or the tumor.

Without intending to limit the disclosure, mechanisms by which such antibodies can exert a therapeutic effect may include, for example, complement-mediated cytolysis, antibody-dependent cellular cytotoxicity (ADCC) modulating the physiologic function of the tumor antigen, inhibiting binding or signal transduction pathways, modulating tumor cell differentiation, altering tumor angiogenesis factor profiles, modulating the secretion of immune stimulating or tumor suppressing cytokines and growth factors, modulating cellular adhesion, DNA crosslink, DNA alkylation, DNA intercalation, microtubule inhibition, and/or by inducing apoptosis.

In one embodiment, the invention provides a method of treating or preventing a disease comprising administering an antibody of the disclosure to a patient, preferably a human patient. In certain embodiments, the disease to be treated or prevented is a cancer.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulvar cancer, thyroid cancer, hepatic carcinoma, anal carcinoma, penile carcinoma, as well as head and neck cancer.

For the prevention or treatment of disease, the appropriate dosage of an antibody will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 0.1 to 20 mg/kg of molecule is an initial candidate dosage for administration to the patient, whether, for example, by one or more separate administrations, or by continuous infusion. A typical daily dosage might range from about 0.1 mg/kg to 20 mg/kg or more, depending on the factors mentioned above. An exemplary dosage of ADC to be administered to a patient is in the range of about 0.1 to about 30 mg/kg of patient weight.

For repeated administrations over several days or longer, depending on the condition, the treatment is sustained until a desired suppression of disease symptoms occurs. An exemplary dosing regimen comprises administering an initial loading dose of about 4 mg/kg, followed by a weekly maintenance dose of about 2 mg/kg of the antibody. Other dosage regimens may be useful. The progress of this therapy is easily monitored by conventional techniques and assays.

An antibody may be combined in a pharmaceutical combination formulation, or dosing regimen as combination therapy, with a second compound having anti-cancer properties. The second compound of the pharmaceutical combination formulation or dosing regimen preferably has complementary activities to the antibody of the combination such that they do not adversely affect each other.

The second compound may be a chemotherapeutic agent, cytotoxic agent, cytokine, growth inhibitory agent, anti-hormonal agent, aromatase inhibitor, protein kinase inhibitor, lipid kinase inhibitor, anti-androgen, antisense oligonucleotide, ribozyme, gene therapy vaccine, anti-immune checkpoint antibodies, cytokines, anti-angiogenic agent and/or cardioprotectant. Such molecules are suitably present in combination in amounts that are effective for the purpose intended. A pharmaceutical composition containing an antibody may also have a therapeutically effective amount of a chemotherapeutic agent such as a tubulin-forming inhibitor, a topoisomerase inhibitor, or a DNA binder.

Other therapeutic regimens may be combined with the administration of an anticancer agent identified in accordance with this disclosure. The combination therapy may be administered as a simultaneous or sequential regimen. When administered sequentially, the combination may be administered in two or more administrations. The combined administration includes co-administration, using separate formulations or a single pharmaceutical formulation, and consecutive administration in either order, wherein there is a time period while both (or all) active agents simultaneously exert their biological activities.

The combination therapy may provide "synergy" and prove "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

Treatment is meant to include therapeutic, prophylactic, palliative, or suppressive treatment for the disease, disorder or undesirable condition. Treatment encompasses administration of the subject antibodies in an appropriate form prior to the onset of disease symptoms and/or after clinical manifestations, or other manifestations, of the disease to reduce disease severity, halt disease progression, or eliminate the disease. Prevention of the disease includes prolonging or delaying the onset of symptoms of the disorder or disease, preferably in a subject with increased susceptibility to the disease.

In certain aspects, the therapeutic preparations can use non-modified antibodies or antibodies conjugated with a therapeutic compound, such as a toxin or cytotoxic molecule, depending on the functionality of the antibody. Generally, when non-modified antibodies are used, they will typically have a functional Fc region. By "functional Fc region" herein is meant a minimal sequence for effecting the biological function of Fc, such as binding to Fc receptors, particularly Fc$\gamma$R (e.g., Fc$\gamma$ RI, Fc$\gamma$RII, and Fc$\gamma$ RIII).

Without being bound by theory, it is believed that the Fc region may affect the effectiveness of anti-tumor monoclonal antibodies by binding to Fc receptors immune effector cells and modulating cell mediated cytotoxicity, endocytosis, phagocytosis, release of inflammatory cytokines, complement mediate cytotoxicity, and antigen presentation. In this regard, polyclonal antibodies, or mixtures of monoclonals will be advantageous because they will bind to different epitopes and, thus, have a higher density of Fc on the cell surface as compared to when a single monoclonal antibody is used. Of course, to enhance their effectiveness in depleting targeted cells, or where non-modified antibodies are not therapeutically effective, antibodies conjugated to toxins or cytotoxic agents may be used.

The antibody compositions may be used either alone or in combination with other therapeutic agents to increase efficacy of traditional treatments or to target abnormal cells not targeted by the antibodies. The antibodies and antibody compositions of the invention may include, for example, PEGylated antibodies and/or pre-targeting constructs of the antibodies. Combining the antibody therapy method with a chemotherapeutic, radiation or surgical regimen may be preferred in patients that have not received chemotherapeutic treatment, whereas treatment with the antibody therapy may be indicated for patients who have received one or more chemotherapies. Additionally, antibody therapy can also enable the use of reduced dosages of concomitant chemotherapy, particularly in patients that do not tolerate the toxicity of the chemotherapeutic agent very well. Furthermore, treatment of cancer patients with the antibody with tumors resistant to chemotherapeutic agents might induce sensitivity and responsiveness to these agents in combination.

In one aspect, the antibodies are used adjunctively with therapeutic cytotoxic agents, including, by way of example and not limitation, busulfan, thioguanine, idarubicin, cytosine arabinoside, 6-mercaptopurine, doxorubicin, daunorubicin, etoposide, and hydroxyurea. Other agents useful as adjuncts to antibody therapy are compounds directed specifically to the abnormal cellular molecule found in the disease state. These agents will be disease specific.

The amount of the compositions needed for achieving a therapeutic effect will be determined empirically in accordance with conventional procedures for the particular purpose. Generally, for administering the compositions ex vivo or in vivo for therapeutic purposes, the compositions are given at a pharmacologically effective dose. By "pharmacologically effective amount" or "pharmacologically effective dose" is an amount sufficient to produce the desired physiological effect or amount capable of achieving the desired result, particularly for treating or retreating the disorder or disease condition, including reducing or eliminating one or more symptoms or manifestations of the disorder or disease.

As an illustration, administration of antibodies to a patient suffering from cancer provides a therapeutic benefit not only when the underlying disease is eradicated or ameliorated, but also when the patient reports a decrease in the severity or duration of the symptoms associated with the disease. Therapeutic benefit also includes halting or slowing the progression of the underlying disease or disorder, regardless of whether improvement is realized.

The amount administered to the subject will vary depending upon what is being administered, the purpose of the administration, such as prophylaxis or therapy, the state or condition of the subject, the manner of administration, the number of administrations, interval between administrations, and the like. These can be determined empirically by those skilled in the art and may be adjusted for the extent of the therapeutic response. Factors to consider in determining an appropriate dose include, but are not limited to, size and weight of the subject, the age and sex of the subject, the severity of the symptom, the stage of the disease, method of delivery, half-life of the antibodies, and efficacy of the antibodies. Stage of the disease to consider includes whether the disease is acute or chronic, relapsing or remitting phase, and the progressiveness of the disease. Determining the dosages and times of administration for a therapeutically effective amount is well within the skill of the ordinary person in the art.

For any compositions of the present disclosure, the therapeutically effective dose is readily determined by methods well known in the art. For example, an initial effective dose can be estimated from cell culture or other in vitro assays. For example, Sliwkowsky, M X et al. (1999) Semin. Oncol. 26.suppl. 12:60 describes in vitro measurements of antibody dependent cellular cytotoxicity. A dose can then be formulated in animal models to generate a circulating concentration or tissue concentration, including that of the IC50 as determined by the cell culture assays.

In addition, the toxicity and therapeutic efficacy are generally determined by cell culture assays and/or experimental animals, typically by determining the LD50 (lethal dose to 50% of the test population) and ED50 (therapeutically effectiveness in 50% of the test population). The dose ratio of toxicity and therapeutic effectiveness is the therapeutic index. Preferred are compositions, individually or in combination, exhibiting high therapeutic indices. Determination of the effective amount is well within the skill of those in the art, particularly given the detailed disclosure provided herein. Guidance is also found in standard reference works, for example Fingl and Woodbury, General Principles In: The Pharmaceutical Basis of Therapeutics pp. 1-46 (1975), and the references cited therein.

To achieve an initial tolerizing dose, consideration is given to the possibility that the antibodies may be immunogenic in humans and in non-human primates. The immune response may be biologically significant and may impair the therapeutic efficacy of the antibody even if the antibody is partly or chiefly comprised of human immunoglobulin sequences, for example, in the case of a chimeric or humanized antibody. Within certain embodiments, an initial high dose of antibody is administered such that a degree of immunological tolerance to the therapeutic antibody is established. The tolerizing dose is sufficient to prevent or reduce the induction of an antibody response to repeat administration of the committed progenitor cell specific antibody.

Ranges for the tolerizing dose are, for example, between 10 mg/kg body weight to 50 mg/kg body weight, inclusive. In some embodiments, ranges for the tolerizing dose are between 20 and 40 mg/kg, inclusive. In still other embodiments, ranges for the tolerizing dose are between 20 and 25 mg/kg, inclusive.

Within these therapeutic regimens, the therapeutically effective dose of antibodies may be administered in the range of 0.1 to 10 mg/kg body weight, inclusive. In certain embodiments, therapeutically effective doses are in the range of 0.2 to 5 mg/kg body weight, inclusive. In other embodiments, therapeutically effective doses are in the range of 0.5 to 2 mg/kg, inclusive. Within alternative embodiments, the subsequent therapeutic dose or doses may be in the same or different formulation as the tolerizing dose and/or may be administered by the same or different route as the tolerizing dose.

Antibody compositions may be formulated for any appropriate manner of administration, including for example, oral, nasal, mucosal, intravenous, intraperitoneal, intradermal, subcutaneous, and intramuscular administration.

For the purposes of this disclosure, the methods of administration are chosen depending on the condition being treated, the form of the subject antibodies, and the pharmaceutical composition.

Administration of the antibody compositions can be done in a variety of ways, including, but not limited to, continuously, subcutaneously, intravenously, orally, topically, transdermal, intraperitoneal, intramuscularly, and intravesically. For example, microparticle, microsphere, and microencapsulate formulations are useful for oral, intramuscular, or subcutaneous administrations. Liposomes and nanoparticles are additionally suitable for intravenous administrations. Administration of the pharmaceutical compositions may be through a single route or concurrently by several routes. For instance, intraperitoneal administration can be accompanied by intravenous injections. Preferably the therapeutic doses are administered intravenously, intraperitoneally, intramuscularly, or subcutaneously.

The compositions may be administered once or several times. In some embodiments, the compositions may be administered once per day, a few or several times per day, or even multiple times per day, depending upon, among other things, the indication being treated and the judgment of the prescribing physician.

Administration of the compositions may also be achieved through sustained release or long-term delivery methods, which are well known to those skilled in the art. By "sustained release or" "long term release" as used herein is meant that the delivery system administers a pharmaceutically therapeutic amount of such compounds for more than a day, preferably more than a week, and most preferable at least about 30 days to 60 days, or longer. Long term release systems may comprise implantable solids or gels containing the antibodies, such as biodegradable polymers described above; pumps, including peristaltic pumps and fluorocarbon propellant pumps; osmotic and mini-osmotic pumps; and the like.

The method of the disclosure contemplates the administration of single monoclonal antibodies and any antibody that recognizes the particular antigens recognized by these antibodies, as well as combinations, of different monoclonal antibodies. Two or more monoclonal antibodies may provide an improved effect compared to a single antibody. Alternatively, a combination of an antibody with an antibody that binds a different antigen may provide an improved effect compared to a single antibody. Such monoclonal antibodies cocktails may have certain advantages inasmuch as they contain monoclonal antibodies, which exploit different effector mechanisms or combine directly cytotoxic monoclonal antibodies with monoclonal antibodies that rely on immune effector functionality. Such monoclonal antibodies in combination may exhibit synergistic therapeutic effects.

In certain embodiments the compositions and methods described herein in can be administered for the treatment of cancer. Therapeutically effective doses can be determined by one of skill in the art and will depend on the severity and course of the disease, the patient's health and response to treatment, the patient's age, weight, height, sex, previous medical history and the judgment of the treating physician.

In some methods of the disclosure, the cancer cell is a tumor cell. The cancer cell may be in a patient. The patient may or may not have a solid tumor. In such cases, embodiments may further involve performing surgery on the patient, such as by resecting all or part of the tumor. BST2 antibodies described herein can be administered as an anti-cancer treatment, whether or not additional cancer therapies have been administered and/or will be administered. Anti-cancer treatments may be administered to the patient before, after, or at the same time as an additional treatment. In some embodiments, patients may be administered the BST2 antibody systemically or locally, including directly, endoscopically, intratracheally, intratumorally, intravenously, intralesional, intramuscularly, intraperitoneally, regionally, percutaneously, topically, intra-arterially, intravesical, or subcutaneously. Anti-cancer BST2 antibody compositions may be administered 1, 2, 3, 4, 5, 6, 7, 8, 9, 10, 11, 12, 13, 14, 15, 16, 17, 18, 19, 20 or more times, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months.

Methods of treating cancer may further include administering to the patient a cancer therapy in addition to the BST2 antibody, which may be administered more than one time. The additional therapy may be chemotherapy, radiation, surgery, immunotherapy, hormone therapy, or a combination thereof. Chemotherapy includes, but is not limited to, docetaxel, cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxotere, taxol, transplatinum, 5-fluorouracil, vincristin, vinblastin, methotrexate, gemcitabine, oxaliplatin, irinotecan, topotecan, or any analog or derivative variant thereof. Radiation therapy includes, but is not limited to, X-ray irradiation, UV-irradiation, γ-irradiation, electron-beam radiation, or microwaves. It is specifically contemplated that any of the compounds or derivatives or analogs, can be used with these combination therapies.

In some embodiments, the cancer for which the individual is in need of treatment may be breast, bladder, blood, bone, bone marrow, brain, colorectal, esophagus, gastrointestinal, head and neck, kidney, liver, lung, nasopharynx, neck, ovary, pancreas, prostate, skin, stomach, testicular, tongue, or uterus cell, as examples only. In certain aspects the cancer is breast cancer or multiple myeloma and may or may not be metastatic.

VI. Methods of Detection

In another embodiment, anti-BST antibodies may be used in diagnostic assays for BST2, e.g., detecting its expression in specific cells, tissues, organs, or serum.

"Detecting" refers to determining the presence, absence, or amount of an analyte (such as a BST2 protein) in a sample, and can include quantifying the amount of the analyte in a sample or per cell in a sample.

"Diagnostic" refers to identifying the presence or nature of a pathologic condition. Diagnostic methods differ in their specificity and sensitivity. While a particular diagnostic method may not provide a definitive diagnosis of a condition, it suffices if the method provides a positive indication that aids in diagnosis.

The present disclosure relates to diagnostic assays, both quantitative and qualitative for detecting levels of BST2 polypeptide in cells, organs, tissues and bodily fluids, including determination of normal and abnormal levels. Assay techniques that can be used to determine levels of a polypeptide, such as the long isoform of BST2 of the present disclosure, in a sample derived from a host are well-known to those of skill in the art. Such assay methods include, but are not limited to, radioimmunoassays, immunohistochemistry assays, in situ hybridization assays, competitive-binding assays, Western Blot analyses and ELISA assays. Among these, ELISAs are frequently used to detect a gene's expressed protein in biological fluids. An ELISA assay initially comprises preparing an antibody specific to BST2, preferably a monoclonal antibody. In addition, a reporter antibody generally is prepared which binds specifically to BST2. The reporter antibody is attached to a detectable reagent such as a radioactive, biotin, fluorescent or enzymatic reagent, for example horseradish peroxidase enzyme or alkaline phosphatase.

The above tests can be carried out on samples derived from subjects' bodily fluids and tissue extracts (homogenates or solubilized tissue) such as from tissue biopsy and autopsy material. Levels of BST2, determined in cells and tissues from a patient suspected of suffering from cancer by measuring the polypeptide or by transcription levels, are compared to levels of BST2 in normal or control cells or tissues. Increased levels of BST2 measured in the subject as compared to levels in the same cells, tissues, or bodily fluids obtained from normal, healthy individuals are indicative of cancer. By "increased levels" it is meant an increase in measured BST2 levels in a subject as compared to BST2 levels in the same normal cells or tissues. Detection of increased BST2 levels is useful in the diagnosis of various cancers including, but not limited to, breast cancer, pancreatic cancer, prostate cancer, melanoma, colon cancer, lung cancer, and thyroid cancer.

Further, monitoring of BST2 levels in a subject diagnosed with cancer is useful in determining the onset of metastases in cancers that have not yet metastasized and in determining the stage of the cancer. For example, detection of BST2 can be used in a method of monitoring cancer in a subject that has not metastasized for the onset of metastasis. In specific embodiments, metastasis of breast cancer is assayed. In this method, a subject suffering from a cancer that is not known to have metastasized may be identified. BST2 levels in a sample from the subject are then measured. These measured BST2 levels are then compared with levels of BST2 from a normal control sample. An increase in measured BST2 levels in the subject versus the normal control is associated with a cancer that has metastasized.

The stage of cancer in a subject suffering from cancer can also be determined. In this method a subject suffering from cancer is identified. BST2 levels in a sample of tissue from the patient are measured to establish a baseline BST2 level for said patient. BST2 levels in samples of the same tissue are then determined at subsequent time periods such as scheduled check-ups with the subject's physician. Measured BST2 levels are then compared with the baseline BST2 levels for the patient. In this method, an increase in measured BST2 levels in the subject versus baseline BST2 levels in the subject is associated with a cancer that is progressing and a decrease in measured BST2 levels versus baseline BST2 levels is associated with a cancer that is regressing or in remission. Increases in measured BST2 levels as compared to baseline BST2 levels established for the subject may also be indicative of metastases.

In one embodiment, BST2 immunohistochemistry functions as an "index diagnostic" to assign risk based on the presence of BST2 expression. Therefore, based on this and other parameters (e.g., size of lesion), one can determine whether or not different therapeutic modalities (i.e., chemotherapy, radiation therapy, surgery) should be used. In a related aspect, methods for monitoring progression of pre-malignancy into a malignant phenotype are disclosed. For example, by using serial sampling (i.e., biopsy) of the tissue and observing the state of BST2 expression in the lesions, one can determine whether or not the pre-malignancies are progressing in a way that would indicate whether therapeutic intervention is advised or is successful.

One aspect of the disclosure includes a method to determine the likelihood of a group of cells to become cancerous, e.g., the cells or glands become pre-malignancies or progress to cancerous lesions. The invention utilizes an agent, such as an antibody, that specifically binds to BST2 protein to assess levels of BST2 in tissue and cells. BST2 expression in cells and tissue may also be assessed using nucleic acid analysis, such as selective amplification, or hybridization methods, immunohistochemistry, and western blot. A level of BST2 above normal or control levels, indicates an increased likelihood that premalignant disease is present, i.e., that the cells or tissues are premalignant.

VII. Sample Preparation

In certain aspects, methods involve obtaining a sample from an individual, including one that is known to have cancer or that is suspected of having cancer, including suspected of having metastatic cancer. The methods of obtaining provided herein may include methods of biopsy, such as fine needle aspiration, core needle biopsy, vacuum assisted biopsy, incisional biopsy, excisional biopsy, punch biopsy, shave biopsy or skin biopsy. In certain embodiments the sample is obtained from a biopsy from ovarian or endometrial tissue by any of the biopsy methods previously mentioned. The sample may be obtained from any other source including but not limited to blood, serum, plasma, sweat, hair follicle, buccal tissue, tears, menses, feces, or saliva. In certain aspects of the current methods, any medical professional such as a doctor, nurse or medical technician may obtain a biological sample for testing. Yet further, the biological sample can be obtained without the assistance of a medical professional.

A sample may include but is not limited to, tissue, cells, or biological material from cells or derived from cells of a subject. The biological sample may be a heterogeneous or homogeneous population of cells or tissues. The biological sample may be obtained using any method known to the art that can provide a sample suitable for the analytical methods described herein. The sample may be obtained by non-invasive methods including but not limited to: scraping of the skin or cervix, swabbing of the cheek, saliva collection, urine collection, feces collection, collection of menses, tears, or semen.

The sample may be obtained by methods known in the art. In certain embodiments the samples are obtained by biopsy. In other embodiments the sample is obtained by swabbing, endoscopy, scraping, phlebotomy, or any other methods known in the art. In some cases, the sample may be obtained, stored, or transported using components of a kit of the present methods. In some cases, multiple samples, such as multiple plasma or serum samples may be obtained for diagnosis by the methods described herein. In other cases, multiple samples, such as one or more samples from one tissue type (for example ovaries or related tissues) and one or more samples from another specimen (for example serum) may be obtained for diagnosis by the methods. Samples may be obtained at different times are stored and/or analyzed by different methods. For example, a sample may be obtained and analyzed by routine staining methods or any other cytological analysis methods.

In some embodiments the biological sample may be obtained by a physician, nurse, or other medical professional such as a medical technician, endocrinologist, cytologist, phlebotomist, radiologist, or a pulmonologist. The medical professional may indicate the appropriate test or assay to perform on the sample. In certain aspects a molecular profiling business may consult on which assays or tests are most appropriately indicated. In further aspects of the current methods, the patient or subject may obtain a biological sample for testing without the assistance of a medical professional, such as obtaining a whole blood sample, a urine sample, a fecal sample, a buccal sample, or a saliva sample.

In other cases, the sample is obtained by an invasive procedure including but not limited to: biopsy, needle aspiration, blood draw, endoscopy, or phlebotomy. The method of needle aspiration may further include fine needle aspiration, core needle biopsy, vacuum assisted biopsy, or large core biopsy. In some embodiments, multiple samples may be obtained by the methods herein to ensure a sufficient amount of biological material.

General methods for obtaining biological samples are also known in the art. Publications such as Ramzy, Ibrahim Clinical Cytopathology and Aspiration Biopsy 2001, which is herein incorporated by reference in its entirety, describes general methods for biopsy and cytological methods.

In some embodiments of the methods described herein, a medical professional need not be involved in the initial diagnosis or sample acquisition. An individual may alternatively obtain a sample through the use of an over the counter (OTC) kit. An OTC kit may contain a means for obtaining said sample as described herein, a means for storing said sample for inspection, and instructions for proper use of the kit. In some cases, molecular profiling services are included in the price for purchase of the kit. In other cases, the molecular profiling services are billed separately. A sample suitable for use by the molecular profiling business may be any material containing tissues, cells, nucleic acids, genes, gene fragments, expression products, gene expression products, or gene expression product fragments of an individual to be tested. Methods for determining sample suitability and/or adequacy are provided.

In some embodiments, the subject may be referred to a specialist such as an oncologist and/or pathologist. The specialist may likewise obtain a biological sample for testing or refer the individual to a testing center or laboratory for submission of the biological sample. In some cases, the medical professional may refer the subject to a testing center or laboratory for submission of the biological sample. In other cases, the subject may provide the sample.

VIII. Engineered Cells and Engineered Anti-BST2
Receptors

Embodiments of the disclosure include use of any anti-
body encompassed herein as part of an antigen recognition
domain for any synthetic receptor that targets BST2. In
specific cases, the antibodies are part or all of an extracel-
lular domain linked in a fusion protein whose other com-
ponents may include a transmembrane domain and cyto-
plasmic domains that may or may not be involved in
signaling. In particular embodiments, any cells may harbor
such an engineered receptor, but in specific cases the cells
are utilized for adoptive cell therapy. In specific embodi-
ments, the cells are immune cells including at least T cells
of any kind, NK cells, NK T cells, tumor-infiltrating lym-
phocytes, B cells, macrophages, or they may be stem cells.

Particular embodiments provide for one or more cell
compositions for treatment of any cancer, including any
cancer that has cells that express BST2, wherein the cells
express an engineered receptor that comprises any anti-
BST2 antibody encompassed herein. The cellular composi-
tions may or may not be formulated for storage, transport,
and/or delivery.

In particular embodiments, the cells are engineered to
express one or more heterologous antigen receptors, such as
engineered TCRs, CARs, and so on. The heterologous
antigen receptors are engineered such that they are syntheti-
cally generated by the hand of man. The cells may be
autologous with respect to a recipient or they may be
allogeneic with respect to a recipient.

A. T Cell Receptors

In some embodiments, the engineered heterologous anti-
gen receptors that target BST2 with antibodies encompassed
herein include recombinant TCRs and/or TCRs cloned from
naturally occurring T cells. A "T cell receptor" or "TCR"
refers to a molecule that contains a variable a and β chains
(also known as TCRα and TCRβ, respectively) or a variable
γ and δ chains (also known as TCRγ and TCRδ, respec-
tively) and that is capable of specifically binding to an
antigen peptide bound to an MHC receptor. In some embodi-
ments, the TCR is in the αβ form.

Typically, TCRs that exist in αβ and γδ forms are gen-
erally structurally similar, but T cells expressing them may
have distinct anatomical locations or functions. A TCR can
be found on the surface of a cell or in soluble form.
Generally, a TCR is found on the surface of T cells (or T
lymphocytes) where it is generally responsible for recog-
nizing antigens bound to major histocompatibility complex
(MHC) molecules. In some embodiments, a TCR also can
contain a constant domain, a transmembrane domain and/or
a short cytoplasmic tail (see, e.g., Janeway et al, 1997). For
example, in some aspects, each chain of the TCR can
possess one N-terminal immunoglobulin variable domain,
one immunoglobulin constant domain, a transmembrane
region, and a short cytoplasmic tail at the C-terminal end. In
some embodiments, a TCR is associated with invariant
proteins of the CD3 complex involved in mediating signal
transduction. Unless otherwise stated, the term "TCR"
should be understood to encompass functional TCR frag-
ments thereof. The term also encompasses intact or full-
length TCRs, including TCRs in the αβ form or γδ form.

Thus, for purposes herein, reference to a TCR includes
any anti-BST2 TCR or functional fragment, such as an
antigen-binding portion of a TCR that binds to a specific
antigenic peptide bound in an MHC molecule, i.e. MHC-
peptide complex. An "antigen-binding portion" or antigen-
binding fragment" of a TCR, which can be used interchangeably, refers to a molecule that contains a portion of the
structural domains of a TCR, but that binds the antigen (e.g.
MHC-peptide complex) to which the full TCR binds. In
some cases, an antigen-binding portion contains the variable
domains of a TCR, such as variable a chain and variable β
chain of a TCR, sufficient to form a binding site for binding
to a specific MHC-peptide complex, such as generally where
each chain contains three complementarity determining
regions.

In some embodiments, the variable domains of the TCR
chains associate to form loops, or complementarity deter-
mining regions (CDRs) analogous to immunoglobulins,
which confer antigen recognition and determine peptide
specificity by forming the binding site of the TCR molecule
and determine peptide specificity. Typically, like immuno-
globulins, the CDRs are separated by framework regions
(FRs) (see, e.g., Jores et al., 1990; Chothia et al., 1988;
Lefranc et al., 2003). In some embodiments, CDR3 is the
main CDR responsible for recognizing processed antigen,
although CDR1 of the alpha chain has also been shown to
interact with the N-terminal part of the antigenic peptide,
whereas CDR1 of the beta chain interacts with the C-ter-
minal part of the peptide. CDR2 is thought to recognize the
MHC molecule. In some embodiments, the variable region
of the β-chain can contain a further hypervariability (HV4)
region.

In some embodiments, the TCR chains contain a constant
domain. For example, like immunoglobulins, the extracel-
lular portion of TCR chains (e.g., a-chain, β-chain) can
contain two immunoglobulin domains, a variable domain
(e.g., $V_a$ or Vp; typically amino acids 1 to 116 based on
Kabat numbering Kabat et al., "Sequences of Proteins of
Immunological Interest, US Dept. Health and Human Ser-
vices, Public Health Service National Institutes of Health,
1991, 5$^{th}$ ed.) at the N-terminus, and one constant domain
(e.g., a-chain constant domain or $C_a$, typically amino acids
117 to 259 based on Kabat, β-chain constant domain or Cp,
typically amino acids 117 to 295 based on Kabat) adjacent
to the cell membrane. For example, in some cases, the
extracellular portion of the TCR formed by the two chains
contains two membrane-proximal constant domains, and
two membrane-distal variable domains containing CDRs.
The constant domain of the TCR domain contains short
connecting sequences in which a cysteine residue forms a
disulfide bond, making a link between the two chains. In
some embodiments, a TCR may have an additional cysteine
residue in each of the α and β chains such that the TCR
contains two disulfide bonds in the constant domains.

In some embodiments, the TCR chains can contain a
transmembrane domain. In some embodiments, the trans-
membrane domain is positively charged. In some cases, the
TCR chains contains a cytoplasmic tail. In some cases, the
structure allows the TCR to associate with other molecules
like CD3. For example, a TCR containing constant domains
with a transmembrane region can anchor the protein in the
cell membrane and associate with invariant subunits of the
CD3 signaling apparatus or complex.

Generally, CD3 is a multi-protein complex that can pos-
sess three distinct chains (γ, δ, and ε) in mammals and the
ζ-chain. For example, in mammals the complex can contain
a CD3γ chain, a CD3δ chain, two CD3ε chains, and a
homodimer of CD3ζ chains. The CD3γ, CD3δ, and CD3ε
chains are highly related cell surface proteins of the immu-
noglobulin superfamily containing a single immunoglobulin
domain. The transmembrane regions of the CD3γ, CD3δ,
and CD3ε chains are negatively charged, which is a char-
acteristic that allows these chains to associate with the positively charged T cell receptor chains. The intracellular tails of the CD3γ, CD3δ, and CD3ε chains each contain a single conserved motif known as an immunoreceptor tyrosine-based activation motif or ITAM, whereas each CD3 chain has three. Generally, ITAMs are involved in the signaling capacity of the TCR complex. These accessory molecules have negatively charged transmembrane regions and play a role in propagating the signal from the TCR into the cell. The CD3- and ζ-chains, together with the TCR, form what is known as the T cell receptor complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds. In some embodiments, a TCR for a target antigen (e.g., a cancer antigen) is identified and introduced into the cells. In some embodiments, nucleic acid encoding the TCR can be obtained from a variety of sources, such as by polymerase chain reaction (PCR) amplification of publicly available TCR DNA sequences. In some embodiments, the TCR is obtained from a biological source, such as from cells such as from a T cell (e.g. cytotoxic T cell), T cell hybridomas or other publicly available source. In some embodiments, the T cells can be obtained from in vivo isolated cells. In some embodiments, a high-affinity T cell clone can be isolated from a patient, and the TCR isolated. In some embodiments, the T cells can be a cultured T cell hybridoma or clone. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al., 2009 and Cohen et al., 2005). In some embodiments, phage display is used to isolate TCRs against a target antigen (see, e.g., Varela-Rohena et al., 2008 and Li, 2005). In some embodiments, the TCR or antigen-binding portion thereof can be synthetically generated from knowledge of the sequence of the TCR.

B. Chimeric Antigen Receptors (CARs)

In some embodiments, the T cells are engineered to express one or more CARs comprising one or more extracellular BST2-recognition domains that specifically bind to BST2. In some embodiments, the antigen is a protein expressed on the surface of cells. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MHC) molecule.

In some embodiments, the CAR comprises: a) one or more intracellular signaling domains, b) a transmembrane domain, and c) an extracellular domain comprising a BST2-binding region, which in specific embodiments is an scFv that binds the antigen.

Exemplary antigen receptors, including CARs and recombinant TCRs, as well as methods for engineering and introducing the receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., 2013;

Davila et al., 2013; Turtle et al., 2012; Wu et al., 2012. In some aspects, the genetically engineered antigen receptors include a CAR as described in U.S. Pat. No. 7,446,190, and those described in International Patent Application Publication No.: WO/2014055668 A1.

Certain embodiments of the present disclosure concern the use of nucleic acids, including nucleic acids encoding an BST2-specific CAR polypeptide, including in some cases a CAR that has been humanized to reduce immunogenicity (hCAR), comprising an intracellular signaling domain, a transmembrane domain, and an extracellular domain comprising one or more signaling motifs. In certain embodiments, the CAR may recognize an epitope comprising the shared space between one or more antigens. In certain embodiments, the binding region can comprise complementary determining regions of a monoclonal antibody, variable regions of a monoclonal antibody, and/or antigen binding fragments thereof. In another embodiment, that specificity is derived from a peptide (e.g., cytokine) that binds to a receptor.

It is contemplated that the human CAR nucleic acids may be human genes used to enhance cellular immunotherapy for human patients. In a specific embodiment, the disclosure includes a full-length CAR cDNA or coding region. The antigen binding regions or domain can comprise a fragment of the $V_H$ and $V_L$ chains of a single-chain variable fragment (scFv) derived from a particular human monoclonal antibody, such as those described in U.S. Pat. No. 7,109,304, incorporated herein by reference. The fragment can also be any number of different antigen binding domains of a human antigen-specific antibody. In a more specific embodiment, the fragment is an antigen-specific scFv encoded by a sequence that is optimized for human codon usage for expression in human cells.

The arrangement could be multimeric, such as a diabody or multimers. The multimers are most likely formed by cross pairing of the variable portion of the light and heavy chains into a diabody. The hinge portion of the construct can have multiple alternatives from being totally deleted, to having the first cysteine maintained, to a proline rather than a serine substitution, to being truncated up to the first cysteine. The Fc portion can be deleted. Any protein that is stable and/or dimerizes can serve this purpose. One could use just one of the Fc domains, e.g., either the CH2 or CH3 domain from human immunoglobulin. One could also use the hinge, CH2 and CH3 region of a human immunoglobulin that has been modified to improve dimerization. One could also use just the hinge portion of an immunoglobulin. One could also use portions of CD8alpha.

In some embodiments, the CAR nucleic acid comprises a sequence encoding other costimulatory receptors, such as a transmembrane domain and a modified CD28 intracellular signaling domain. Other costimulatory receptors include, but are not limited to one or more of CD28, CD27, OX-40 (CD134), DAP10, DAP12, and 4-1BB (CD137). In addition to a primary signal initiated by CD3zeta, an additional signal provided by a human costimulatory receptor inserted in a human CAR is important for full activation of T cells and could help improve in vivo persistence and the therapeutic success of the adoptive immunotherapy.

The sequence of the open reading frame encoding the chimeric receptor can be obtained from a genomic DNA source, a cDNA source, or can be synthesized (e.g., via PCR), or combinations thereof. Depending upon the size of the genomic DNA and the number of introns, it may be desirable to use cDNA or a combination thereof as it is found that introns stabilize the mRNA. Also, it may be further advantageous to use endogenous or exogenous non-coding regions to stabilize the mRNA.

It is contemplated that the chimeric construct can be introduced into immune cells as naked DNA or in a suitable vector. Methods of stably transfecting cells by electroporation using naked DNA are known in the art. See, e.g., U.S. Pat. No. 6,410,319. Naked DNA generally refers to the DNA encoding a chimeric receptor contained in a plasmid expression vector in proper orientation for expression.

Alternatively, a viral vector (e.g., a retroviral vector, adenoviral vector, adeno-associated viral vector, or lentiviral vector) can be used to introduce the chimeric construct into immune cells. Suitable vectors for use in accordance with the method of the present disclosure are non-replicating in the immune cells. A large number of vectors are known that are based on viruses, where the copy number of the virus maintained in the cell is low enough to maintain the viability of the cell, such as, for example, vectors based on HIV, SV40, EBV, HSV, or BPV.

In some aspects, the BST2-specific binding, or recognition component is linked to one or more transmembrane and intracellular signaling domains. In some embodiments, the CAR includes a transmembrane domain fused to the extracellular domain of the CAR. In one embodiment, the transmembrane domain that naturally is associated with one of the domains in the CAR is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 zeta, CD3 epsilon, CD3 gamma, CD3 delta, CD45, CD4, CD5, CD8, CD9, CD 16, CD22, CD33, CD37, CD64, CD80, CD86, CD 134, CD137, CD154, ICOS/CD278, GITR/CD357, NKG2D, and DAP molecules. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain.

IX. Detection and Vaccination Kits

A peptide and/or antibody of the disclosure may be included in a kit. The peptide and/or antibody in the kit may be detectably labeled or immobilized on a surface of a support substrate also comprised in the kit. The peptide(s) or antibody may, for example, be provided in the kit in a suitable form, such as sterile, lyophilized, or both.

The support substrate comprised in a kit of the disclosure may be selected based on the method to be performed. By way of nonlimiting example, a support substrate may be a multi-well plate or microplate, a membrane, a filter, a paper, an emulsion, a bead, a microbead, a microsphere, a nanobead, a nanosphere, a nanoparticle, an ethosome, a liposome, a noisome, a transferosome, a dipstick, a card, a celluloid strip, a glass slide, a microslide, a biosensor, a lateral flow apparatus, a microchip, a comb, a silica particle, a magnetic particle, or a self-assembling monolayer.

As appropriate to the method being performed, a kit may further comprise one or more apparatuses for delivery of a composition to a subject or for otherwise handling a composition of the disclosure. By way of a non-limiting example, a kit may include an apparatus that is a syringe, an eye dropper, a ballistic particle applicator, a scoopula, a microslide cover, a test strip holder or cover, and such like.

A detection reagent for labeling a component of the kit may optionally be comprised in a kit for performing a method of the present disclosure. In particular embodiments, the labeling or detection reagent is selected from a group comprising reagents used commonly in the art and including, without limitation, radioactive elements, enzymes, molecules which absorb light in the UV range, and fluorophores such as fluorescein, rhodamine, auramine, allophycocyanin (APC), phycoerythrin (PE), Texas Red, AMCA blue and Lucifer Yellow, or Alexafluor derivatives. In other embodiments, a kit is provided comprising one or more container means and a BST2 peptide or antibody already labeled with a detection reagent selected from a group comprising a radioactive element, an enzyme, a molecule which absorbs light in the UV range, and a fluorophore.

When reagents and/or components comprising a kit are provided in a lyophilized form or as a dry powder, the lyophilized reagent or the powder can be reconstituted by the addition of a suitable solvent. In particular embodiments, the solvent may be a sterile, pharmaceutically acceptable buffer and/or other diluent. It is envisioned that such a solvent may also be provided as part of a kit.

When the components of a kit are provided in one and/or more liquid solutions, the liquid solution may be, by way of non-limiting example, a sterile, aqueous solution. The compositions may also be formulated into an administrative composition. In this case, the container means may itself be a syringe, pipette, topical applicator or the like, from which the formulation may be applied to an affected area of the body, injected into a subject, and/or applied to or mixed with the other components of the kit.

EXAMPLES

The following examples are included to demonstrate certain non-limiting aspects of the disclosure. It should be appreciated by those of skill in the art that the techniques disclosed in the examples that follow represent techniques discovered by the inventors to function well in the practice of the disclosed subject matter. However, those of skill in the art should, in light of the present disclosure, appreciate that many changes can be made in the specific embodiments that are disclosed and still obtain a like or similar result without departing from the spirit and scope of the disclosed subject matter.

Example 1

BST2 Isoforms; Distribution and Use in Cancer Therapeutics

The present example considers methods and compositions for characterization of BST2 with respect to its isoforms, distribution, and functions, particularly with respect to cancer.

In a specific embodiment, the long isoform of BST2 (BST2 long) is preferentially expressed on cancerous cells and is involved in modulating the immune microenvironment by interacting with infiltrating immune cells, such as plasmacytoid dendritic cells (pDCs). In a specific embodiment, the expression of the isoform H of BST2 (BST2 medium) is preferentially expressed or restricted to expression in normal cells.

Embodiments of the present disclosure include generation of anti-human-BST2 mAbs by hybridoma technology, targeting specifically the BST2 long. Embodiments also include characterization of the specificity of the antibodies and performance of pharmacokinetic analysis of selected purified clones to identify the best mAbs candidates for immunohistochemistry (IHC) and for therapeutic use. Also included herein are embodiments regarding use of the generated anti-human-BST2 mAbs to analyze the expression of the long BST2 isoform in cancer and in normal tissues by IHC. Embodiments also include study of the function of BST2 in T47D breast cancer cell line, as an example of a breast cancer cell line.

Example 2

Examples of Materials and Methods

Examples of materials and methods are provided herein. Full length BST2 (BST2—long) vector was commercially available. HEK293 cells were previously transfected with these plasmids and BST2 expression was confirmed by Western Blot analysis. Moreover, these two stable cell lines (HEK293-long, and HEK293-medium) were recognized by the anti-BST2 mAb (26F8) previously generated in our laboratory. Later, using a T cell line with Nuclear Factor of Activated T-cells—Green Fluorescent Protein (NFAT-GFP) construct, there was successful integration of a human immunoglobulin like transcript 7 (ILT7)—Fc epsilon RI gamma protein (FCeRIy) complex and created a report cell line that expresses GFP upon interaction between ILT7 & and its ligand, BST2 (30). HEK293 D cells (expressing the long isoform of BST2) were able to activate NFAT, with a resultant in GFP expression. The HEK293 H (expressing medium isoform of BST2) failed to activate the reporter cells.

In a prior experiment, using the same reported cell system, co-culture of the reporter cells with human breast carcinoma MDA-MB-468, MCF7, and T47D cells induced GFP expression by the reporter cells. In contrast, other nonmalignant cell lines known to express BST2 like HEK293, Vero and CHO failed to induce GFP expression when co-cultured with the same reporter cells (31).

The following materials and methods were utilized in embodiments of the disclosure and are provided merely as illustrations.

Antigen for Mice Immunization

The synthetic peptide (SEQ ID NO:1) used as the antigen for immunization was produced by ThermoFisher Scientific in two forms, peptide alone and Keyhole limpet hemocyanin (KLH)-conjugated peptide.

Injection doses preparation: The immunization doses were emulsified using Incomplete Freund Adjuvant (IFA—InvivoGen). Equal volumes of BST2-Long (D) peptide and IFA were mixed vigorously for several minutes, using a 28 Gauge insulin syringe, until a white emulsion with maximum stability is formed. Each emulsified 20 ul dose contained 10 ug of BST2-D peptide-KLH. On the three additional weekly boost injections, the dose of the peptide was raised to 15 ug.

Animal Work

All animal experiments were conducted according to the University of Texas MD Anderson Cancer Center's Institutional Animal Care and Use Committee (IACUC) guidelines and approved protocols (Protocol IACUC 00000620-RN02). Female Balb/c mice were purchased from Jackson Laboratories (Bar Harbor, ME).

Tail vein blood collection: 50 ul of blood samples were collected from the lateral tail vein. It was punctured with a 28-gauge insulin needle, while mice were restrained. After coagulation, serum was separated. Equal volume of glycerol was added to the serum and samples were stored at −20° C. until serum titration ELISA assay was performed to measure the immune response. A total of three serum samples were collected on day 0 (preimmunization), day 14 (after 5 injections) and day 31 after completing the schedule of immunization.

Immunization, route and schedule: Three 6-8-week-old female Balb/c mice were immunized. On day 0, 50 ul pre-immunization serum sample was taken from each mouse and the first dose of a series of 5 injections was given through a footpad route. These footpad injections were given at 2-day intervals (Day 0, 3, 6, 9 and 12). Three additional weekly injections were given to boost the immune response (Day 15, 22 and 29) to complete a total of 8 injections.

Euthanasia: Following MD Anderson IACUC guidelines, the mice were exposed to Carbon Dioxide (CO2) in the CO2 chamber, at a flow rate of 2 L/min for 6 minutes. Cervical dislocation was performed as a secondary euthanasia method.

Harvesting the popliteal lymph nodes: After euthanasia, the mice were whipped with ethanol 70%, transferred to the tissue culture hood and pinned into a dissection board. Using scissors, a midline incision is made, and the fur was removed. The popliteal lymph node, located at the popliteal fossa and embedded in adipose tissue, was carefully excised to preserve the node structure and integrity. Only the popliteal lymph nodes draining the injected footpad were collected and placed in a petri dish with RPMI-1640 medium.

Hybridoma Generation

The two mice with the highest serum titers were selected for fusion while the third mouse was reserved as a backup. The following materials and media were used:

HAT supplement (50×) (Sigma): this mixture of hypoxanthine (5 mM), aminopterin (20 μM) and thymidine (0.8 mM) was used to prepare the HAT selection medium against unfused or self-fused Sp 2/0 myeloma cells. As a folic acid inhibitor, aminopterin blocks the de novo pathway for nucleoside synthesis in the SP2/0 myeloma cells, which lack the hypoxanthine-guanine phosphoribosyl transferase (HGPRT) enzyme and, hence, lose the ability to utilize nucleotides provided by the salvage pathway.

RPMI-1640 medium (Sigma): used to prepare the selection medium and washing cells.

Polyethylene glycol (PEG 1450): used as the fusing agent in the hybridoma technique. On the day of fusion, 1 ml vial of PEG is maintained at 37° C. until the fusion step.

Rat Supplement (RSCM), used as a growth supplement for the hybridomas.

Fetal Bovine Serum (FBS).

The selection media consists of RPMI-1640 with 10% FBS, 2% HAT supplement 50×, and 3% RSCM.

The following cells were used during the hybridoma generation study:

SP2/0: The myeloma cell line SP2/0 was selected as a partner cell line for hybridoma generation. One week before fusion, SP2/0 murine myeloma cells were thawed, maintained in RPMI-1640 and 10% FBS and expanded to $1 \times 10^8$ cells in petri dishes. On the day of fusion, cells were collected in 50 ml tubes, centrifuged and washed twice with RPMI medium before the fusion process.

Murine lymphocytes: These cells are collected from the excised popliteal lymph nodes. These lymph nodes are dissected with scissors and forced, with a glass pestle, through a sterile stainless-steel strainer, to collect the cells in RPMI medium. The collected lymphocytes are centrifuged (1000 RPM for 3 minutes) and washed twice with RPMI medium before the fusion process.

Both SP2/0 and murine lymphocytes were counted, using cell counting hemocytometer, combined in a ratio of 1:2 (Sp2/0 to lymphocytes) in a 50 ml tube, and centrifuged at 1000 RPM for 5 minutes, in order to pack the cells together and prepare them for the fusion. After discarding the supernatant and loosening the cell pellet, 1 ml pre-warmed (37° C.) PEG was added to the cells while swirling the tube for 45 seconds. The reaction was stopped by adding 24 ml pre-warmed (37° C.) RPMI medium. Fused cells were centrifuged at 1000 RPM for 5 minutes, supernatant was discarded, cell pellet was loosened by gentle tapping and transferred to the selection medium. The hybridoma cells suspension was distributed into six 96 MW plates (150 ul/well) and incubated at 37° C., 5% $CO_2$.

Hybridomas Colony Pickup

Seven days after fusion, ELISA was performed to detect positive wells containing hybridoma colonies. Upon results, the procedure of "single colonies pickup" was performed in two phases at 1-week interval. Well-demarcated colonies were identified, collected with 2 ul pipette and transferred into 96 multi-well plate, containing hypoxanthine and thymidine (HT)-selection media. These colonies were incubated at 37° C. and 5% $CO_2$. A total of 563 colonies were picked up in the two phases:

Phase I: 284 colonies

Phase II: 279 colonies

After 2 days, Primary screening was performed via ELISA.

ELISA Screening

To select the hybridomas capable of producing specific monoclonal antibodies against the BST2-D peptide, ELISA was performed. ELISA plates were coated with a 100 ul coating buffer, containing the BST2-D peptide in a concentration of 1 ug/ml, and incubated overnight at 4° C. Next day, ELISA plates were washed three times with PBST (PBS containing 0.05% v/v Tween®-20) and blocked with 100 ul of blocking buffer (PBS, 1% w/v BSA). After 1-hour blocking at room temperature, 50 ul supernatant from each of the 563 colonies were added to individual wells as the primary antibodies. Anti-BST2 mAb (Clone 26F8) [eBioscience] was used as a positive control and blank wells with secondary antibody only were performed in triplicates. Incubation proceeded for 1 hour followed by three washes. 50 ul of secondary antibody, goat IgG anti-mouse, HRP conjugated (1:2000) was added to each well and incubated for 1 hour. After washing 4 times, the substrate solution (TMB) was added to each well and incubated for 30 minutes. The reaction was stopped with $H_2SO_4$ 0.2N and the OD absorbance values were read at 450 nm. This screening step was repeated twice. The 26 hybridomas were transferred to 24 MW plates containing HT-medium, and incubated for 4-7 days at 37° C., 5% $CO_2$. 2 ml supernatant was collected from each clone for further characterization of the monoclonal antibodies.

For ELISA dilution assay, ELISA plates were coated overnight with 0.5 ug/ml BST2-D peptide and serial dilutions of the pre-collected supernatants were used as primary antibodies (undiluted, 1/15, 1/225 and 1/3375). The clones with the highest OD 450 nm signal were selected to proceed to the next screening assays.

For cell-based ELISA, plates were loaded with parental HEK-293 cells, HEK293 expressing BST2-long, or HEK293-medium at a density of $15 \times 10^4/50$ ul per well and dried at RT overnight. ELISA was performed as described before using 50 ul of supernatants from each monoclonal antibody.

Flow Cytometry Staining and Analysis (FACS)

For flow cytometry assays, cells were detached using 0.05% trypsin-EDTA, counted, washed and resuspend with FACS Buffer (PBS, 2% FBS, 2 mM EDTA). $2 \times 10^5$ cells in 100 ul/well were placed in U-bottom 96-well plate and centrifuged (1000 RPM/3 min/4° C.). The buffer was discarded and 100 ul of the previously collected supernatants with selected monoclonal antibodies were added to the wells and incubated on ice for 30 minutes. After incubation, the plate was washed three times with FACS buffer and 50 ul of diluted (1/250) secondary antibody (Donkey anti-mouse Allophycocyanin (APC) conjugated) were added to the wells and incubated on ice for 20 minutes protected from light. The final wash was repeated 4 times, and the samples were transferred and analyzed at the South Campus Flow Cytometry & Cell Sorting Core Laboratory at MD Anderson Cancer Center. FACS data were analyzed with FlowJo™ Software—for Windows (Version 10.6.1. Ashland, OR: Becton, Dickinson and Company; 2020).

Hybridoma Subcloning

The hybridoma clone (LA5) was expanded in 24 well plates with HT-based media for three days. With a 70% confluency and viability of more than 90%, cells were counted (using hemocytometer), diluted with HT-based media to a concentration of 5 cells/ml, and lastly added 200 ul/well to a 96 well tissue culture plate, using a multichannel pipet. The hybridomas were cultured for 7-10 days at 37° C., 5% $CO_2$. Screening was performed by ELISA as described before against BST2 D peptide. The absorbance values were read as 450 OD and the two wells with the highest OD signal were maintained and transferred into a 24-well plate. Two days later, HT-based medium was substituted with RPMI-FBS 10% and the clones were transferred to T25. Further expansion into T75 was performed for the purpose of monoclonal antibody purification.

Purification and Concentration of the Monoclonal Antibodies

After expansion and incubation of the selected hybridomas, 300 ml of the mAb-rich supernatants were collected, centrifuged and filtered through 0.45-micron membrane. mAbs were purified using Protein A affinity Chromatography method (GE Healthcare MabSelect SuRe Cat #17-5438-08). After the purification columns were assembly and wash, supernatant was neutralized with 1 M Tris-HCl (pH 9) buffer and allowed to run in the columns twice. The captured antibodies were eluted from the columns, using elution buffer (0.1 M glycine-HCl, pH 3) and the concentration was measured in the Nanodrop. An overnight dialysis in PBS (Fisherbrand Regenerated Cellulose Dialysis Tubing) was performed and the concentrated anti-BST2-long (clone LA5) mAb (1 mg/ml) was collected and stored at 4° C., ready for further characterization and cell assays.

Antibody Isotyping

The isotype of the generated monoclonal antibody was determined, using Mouse Monoclonal Antibody Isotyping Reagents (Sigma-Aldrich, Catalog Number ISO2] following manufacturer recommendations. It is based on the ELISA technique.

Affinity Testing

Using Octet RED384 System, the kinetics of the generated monoclonal antibody were tested and compared to the anti-BST2 (clone26F8) mAbs [eBioscience]. Developed by ForteBIO and based on Bio-Layer Interferometry (BLI) technology, Octet RED384 system can measure the affinity constant (KD) of an antibody with a range of 1 mM to 5 pM (32). The following materials and conditions were utilized during the experiments:

Sensor type: AMC (Anti-mouse IgG Fc capture) biosensor (part number 18-5088, ForteBIO).

10× Kinetics buffer: 10 mM Phosphate, 150 mM NaCl, 0.02% Tween 20, 0.05% Sodium Azide, 1 mg/mL BSA (pH 7.4) (part number 18-5060, ForteBIO).

Monoclonal antibodies: clones LA5 and 26F8 at a concentration of 5 ug/ml.

Recombinant human BST2 protein (Catalog number 13370-H07H, Sino Biological).

BST2 protein concentrations: a serial dilution of concentrations was used to measure the KD value of the monoclonal antibodies (1000, 500, 250, 125, 62.5, 31.25 and 15.625 nanomolar). The calculated nanomolar concentrations were based on the molecular weight of the protein.

Assay steps and time: following the guidelines, Table 3.1 describe the steps of the assay and time spent in each step.

Data Analysis: Octet Data Acquisition software V10.x was utilized to analyze the results. A 1:1 binding model was employed, where both the association and dissociation phases were taken into consideration, and results were obtained after global fitting from the various concentrations of protein.

TABLE 1

| The steps and times of the kinetics assay using the Octet RED384 system | | |
|---|---|---|
| Assay step | Step name | Assay time (seconds) |
| 1 | Baseline | 60 |
| 2 | Loading | 300 |
| 3 | Baseline | 300 |
| 4 | Association | 300 |
| 5 | Dissociation | 300 |
| 6 | Regeneration | 5 |

Specificity

A specificity assay was performed and analyzed through flow cytometry staining of MM1, a multiple myeloma cell line. In this assay, changes in the binding of the LA5 mAb to the BST2 receptor expressed on MM1 cell lines were assessed after:

10 minutes—preincubation with BST2 protein (5 ug/ml).

10 minutes—preincubation with Spartan protein (5 ug/ml).

Results were compared to the anti-BST2 Clone 26F8 mAb and mouse IgG1 isotype control (eBioscience, catalog #14-4714-82). FACS data was analyzed with FlowJo™ Software—for Windows (Version 10.6.1. Ashland, OR: Becton, Dickinson and Company; 2020).

Cell Lines and Media

The Following Cell Lines were Used:

B-LCL: a non-malignant B cell line that has been infected with Epstein-Barr virus (EBV) to provide a continuous source of primary B cells (Astrarte Biologics). These cells were maintained and expanded on RPMI-1640 medium, supplemented with 10% FBS.

MM1: a multiple myeloma cell line that was generously provided by Dr. Robert Orlowski's laboratory. It represents malignant B-lymphoblasts that grow in suspension and as lightly attached cells. These cells were maintained and expanded on RPMI-1640 medium, supplemented with 10% FBS.

U266: a multiple myeloma cell line that was generously provided by Dr. Robert Orlowski's laboratory. It represents malignant B-lymphocytes that grow in suspension. These cells were maintained and expanded on RPMI-1640 medium, supplemented with 10% FBS.

MCF-10A: a nonmalignant epithelial breast tissue cell line (ATCC® CRL-10317). This cell line grows in a special medium that was purchased from Lonza/Clonetics as a kit (MEGM, Kit Catalog No. CC-3150).

MDA-MB-231: human breast adenocarcinoma cell line that was generously provided by Dr. Ze Tian. These cells grow in RPMI-1640 based medium, supplemented with 10% FBS.

MCF7: human breast adenocarcinoma cell line that was generously provided by Dr. Ze Tian. These cells grow in Dulbecco's Modified Eagle's medium, supplemented with 10% FBS.

T47D: human breast ductal epithelial carcinoma. Stocks of this cell lines were available in our lab. These cells grow in RPMI-1640 based medium, supplemented with 10% FBS.

Immunocytochemistry and Immunohistochemistry

The immunocytochemistry (ICC) assays on transduced cells overexpressing BST2 isoforms were performed by the Research Histology Core Laboratory (RHCL) at MD Anderson Cancer Center. Paraffin blocks were prepared from cell pellets of HEK293, HEK293 BST2-long and HEK293 BST2-medium. Briefly, all cell pellets were fixed in 4% formalin for 10 minutes, centrifuged and washed with PBS and resuspend in fresh PBS to be submitted to the Histology Core. The pellets were embedded in paraffin with standard techniques. 5 μm sections were cut and stained with the corresponding supernatants or purified antibodies. The ICC detection of BST2 was performed with the DAB kit (DAKO). Hydrogen peroxide was used to deactivate intrinsic peroxidase. Antigen retrieval was performed in a water bath using citrate-EDTA buffer (10 mM citric acid, 2 mM EDTA, 0.05% Tween 20, pH 6.2). Sections were incubated with undiluted supernatant containing secreted anti-BST2 antibodies or with a purified antibody. As negative controls, immunostaining was performed by incubating samples with PBS instead of the primary antibody containing supernatant. After staining with DAB and counterstaining with hematoxylin, the slides were recorded using a digital camera. The immunohistochemistry assays on human breast cancer tissues was performed at the laboratory of Molecular Pathology, Hospital El Cruce, Florencio Varela, Buenos Aires, Argentina (Dr. Ines Bravo).

BST2 Silencing Using Short Hairpin RNA (shRNA)

The Functional Genomic Core (FGC), at MD Anderson Cancer Center, carries a human shRNA library that targets the entire human genome, including 5 plasmids that target human BST2. Briefly, through collaboration with the FGC, the 5 different BST2 silencing plasmids (as well as a nonsilencing control) were introduced into E. coli strain DH5 alpha. E. coli DH5α harboring a plasmid is inoculated into an ampicillin—containing LB media and cultured at the 37° C. in a shaker incubator overnight. The plasmids were extracted using QIAGEN Plasmid Plus Midi Kit. HEK-293T cells were used to generate shRNA-containing lentivirus using a third-generation lentiviral system. jetPRIME reagent was used as a transfection reagent [Polyplus transfection, reference number 114-15]. The lentivirus containing-supernatant were collected 24- and 48-hours post-transfection and were concentrated [LentiFuge Viral Concentration Reagent, Cellecta, Catalog #LFVC1].

Transduction of the Cell Lines.

The first step in transduction was to set the experiment conditions. The following assays were performed:

Lentiviral transduction titration assay

Polybrene toxicity assay

Puromycin titration assay

Using a 6-well plate, 2-3\*10^5 cells were seeded per well. 24 hours later, 40 ul of 4× Lentivirus vector was added/well, which was based on the multiplicity of infection (MOI) of 5. To enhance transduction, polybrene was added in a concentration of 8 ul/ml. 48 hours post-transduction, 2 ug/ml Puromycin was added to each well as a selective antibiotic. 10 days post-transduction, BST2 expression was assessed, using western blot and flowcytometry staining.

Cell Viability Assay

Cell viability assay was performed on cells following BST2 silencing, using CellTiter-Glo Luminescent (Promega, Catalog #G7570), following manufacturer protocol.

Cell Proliferation Assay

Cell proliferation assay was performed on cells following BST2 silencing using XTT-Cell Proliferation Assay Kit (ThermoFisher Scientific, Catalog #X12223).

Reverse Phase Protein Array (RPPA)

Samples of BST2 non-silenced and silenced cell lines were sent to The Reverse Phase Protein Array (RPPA) Core at MD Anderson Cancer Center for functional proteomics studies. Cell pellets were prepared at our lab and stored at −80° C. Protein extraction was performed at the RPPA core lab.

Statistical Analysis

Statistical analysis was performed with FlowJo™ Software—for Windows (Version 10.6.1. Ashland, OR: Becton, Dickinson and Company; 2020) and/or GraphPad Prism Software version 7.00 (La Jolla, California) for Windows. Data sets were analyzed with Mann-Whitney U Test, Student T-Test or ANOVA test.

P values for comparisons between groups were determined and a value of less than 0.05 was interpreted as statistically significant.

Example 3

Generating the BST2 Long Isoform Peptide, Immunization and Serum Titer

To generate monoclonal antibodies specifically against the long isoform of BST2 (BST2-D), a unique sequence should be identified. By comparing the amino acid sequences of the different isoforms of BST2, there was identified a section of the extracellular domain of the BST2 protein that is found exclusively in the long isoform and not in the other isoforms of BST2. The peptide position spans from position 133 to 156 of the long isoform of the BST2 position and the number of residues is 24. The amino acid sequence of the generated peptide is EVERLR-RENQVLSVRIADKKYYPS (SEQ ID NO:1). The peptide has the following molecular characteristics:

Molecular weight: 2949.32 g/mol

Isoelectric point: pH 10

Solubility: Good water solubility

Given the small size of peptide, the use of KLH as a carrier protein was selected to ensure an adequate immune response can be elicited after mice immunization.

Figure 3:
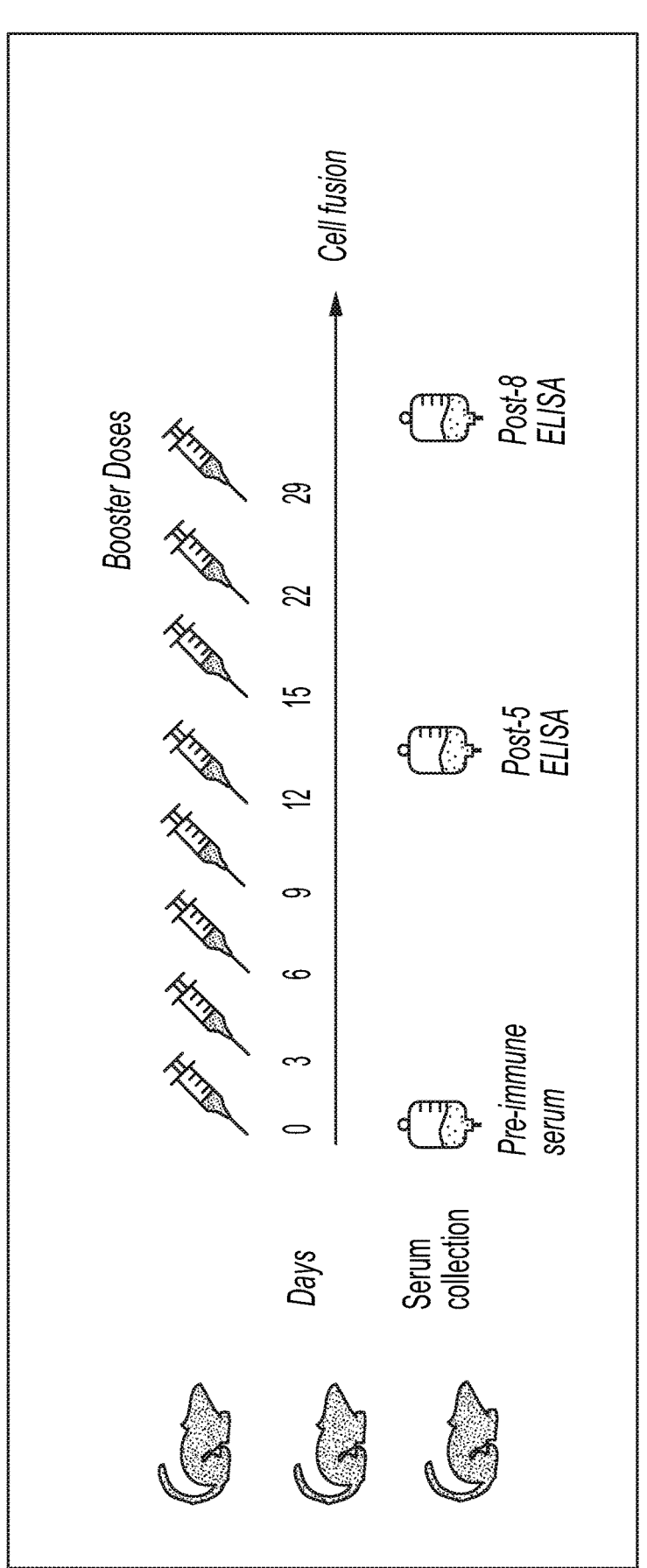
FIG. 3. Immunization Schedule. Three mice were immunized every 3 days for the first five doses and then weekly for the three boosts doses. Blood samples were drawn at indicated times, following the IACUC protocol 00000620-RN02.

Three female Balb/c mice 6-8 weeks old were selected for immunization. Pre-immunization samples were collected and a series if footpad injections were scheduled at a defined interval (FIG. 3).

Figure 4A:
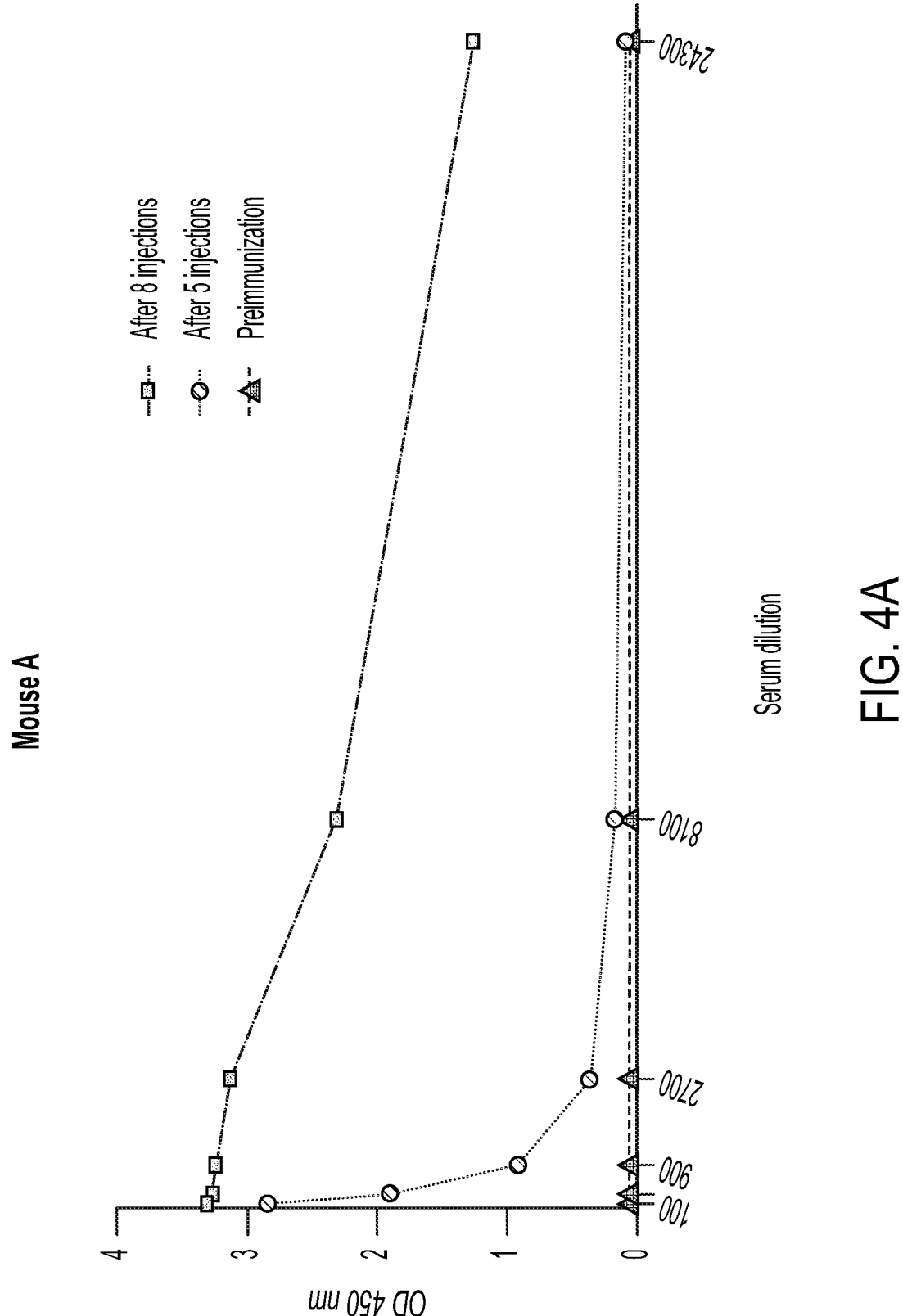
FIGS. 4A-4C. Immune Response. Titration curves compare the immune response from the immunized mice (A, B and C.
Figure 4B:
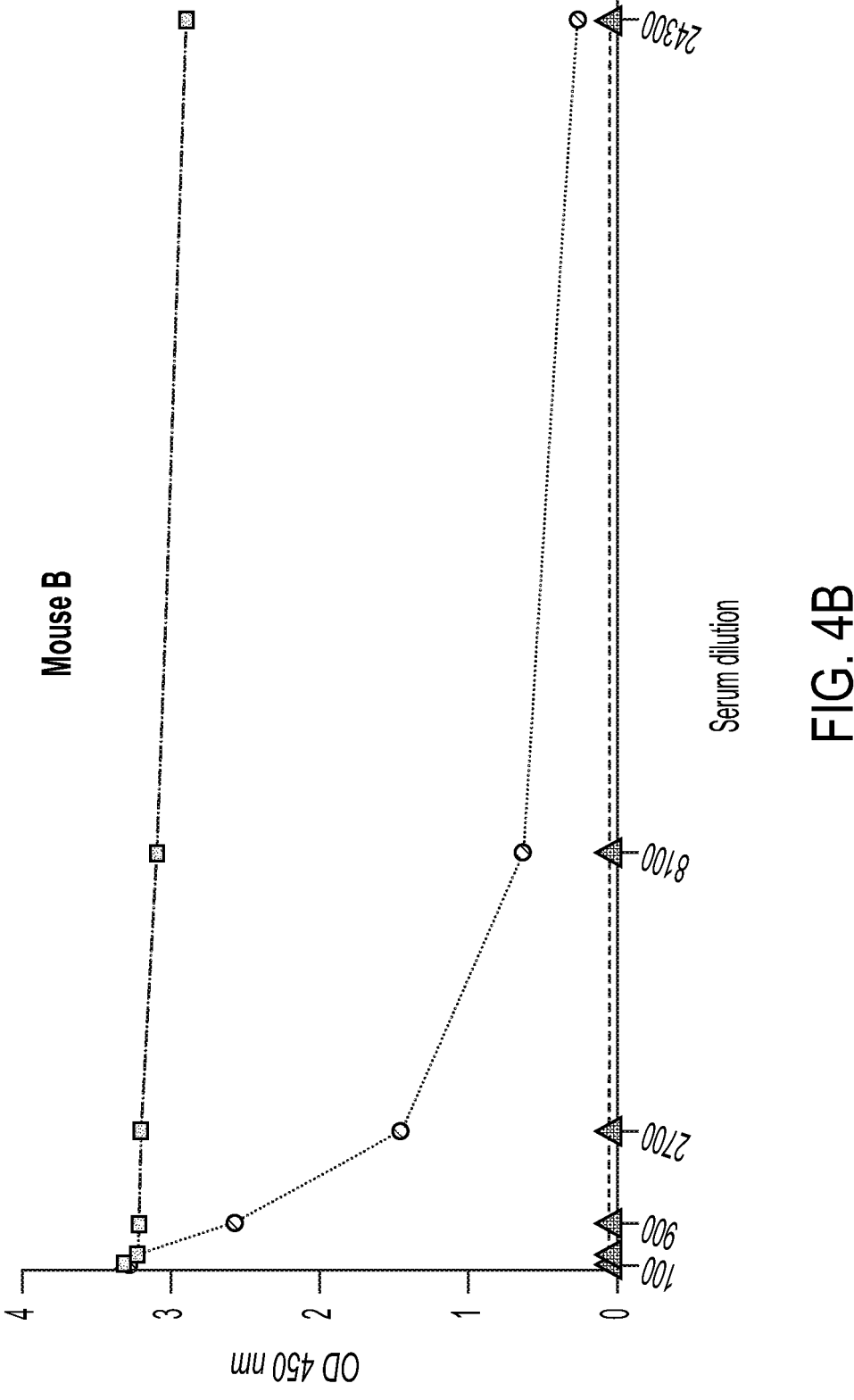
Figure 4C:
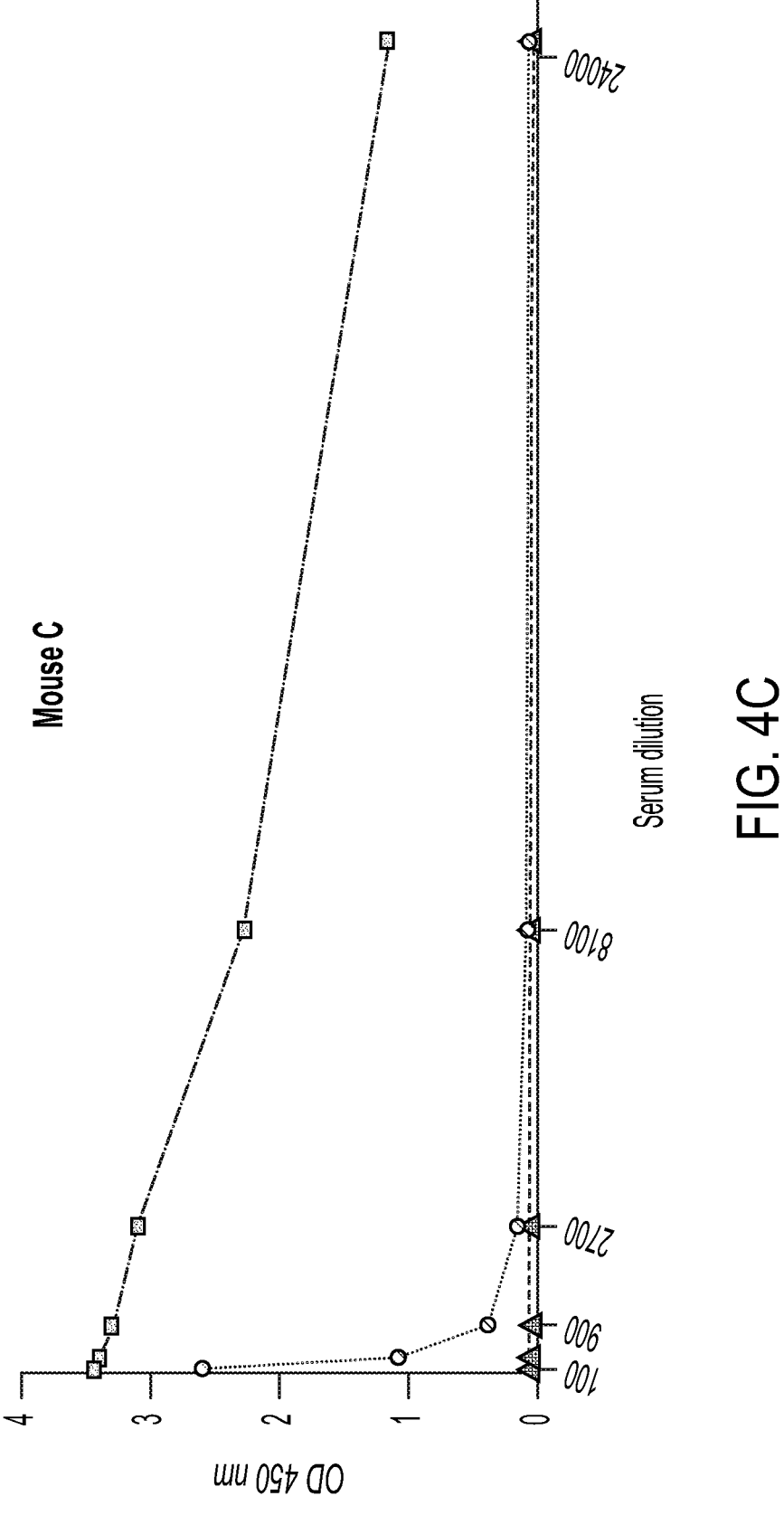

Reasons for choosing the footpad route were the establishment of an easy and quick way to monitor the host immune response and the ability to collect a higher population of a specifically—responding B lymphocytes to be used in the hybridoma technique, by harvesting the popliteal lymph nodes (33). To measure the immune response, serum titration performed after five injections, using ELISA technique, showed insufficient immune response necessary for a successful cell fusion. After the third weekly booster dose, serum titration assay was repeated and revealed an adequate immune response in each mouse to proceed with the hybridoma generation by chemical fusion (FIG. 4). Mice A (FIG. 4A) and B (FIG. 4B) were selected for the hybridoma experiment, while Mouse C (FIG. 4C) was maintained as a backup source for reactive B lymphocytes.

Example 4

Fusion, Hybridoma Generation and ELISA Screening

Figure 5:
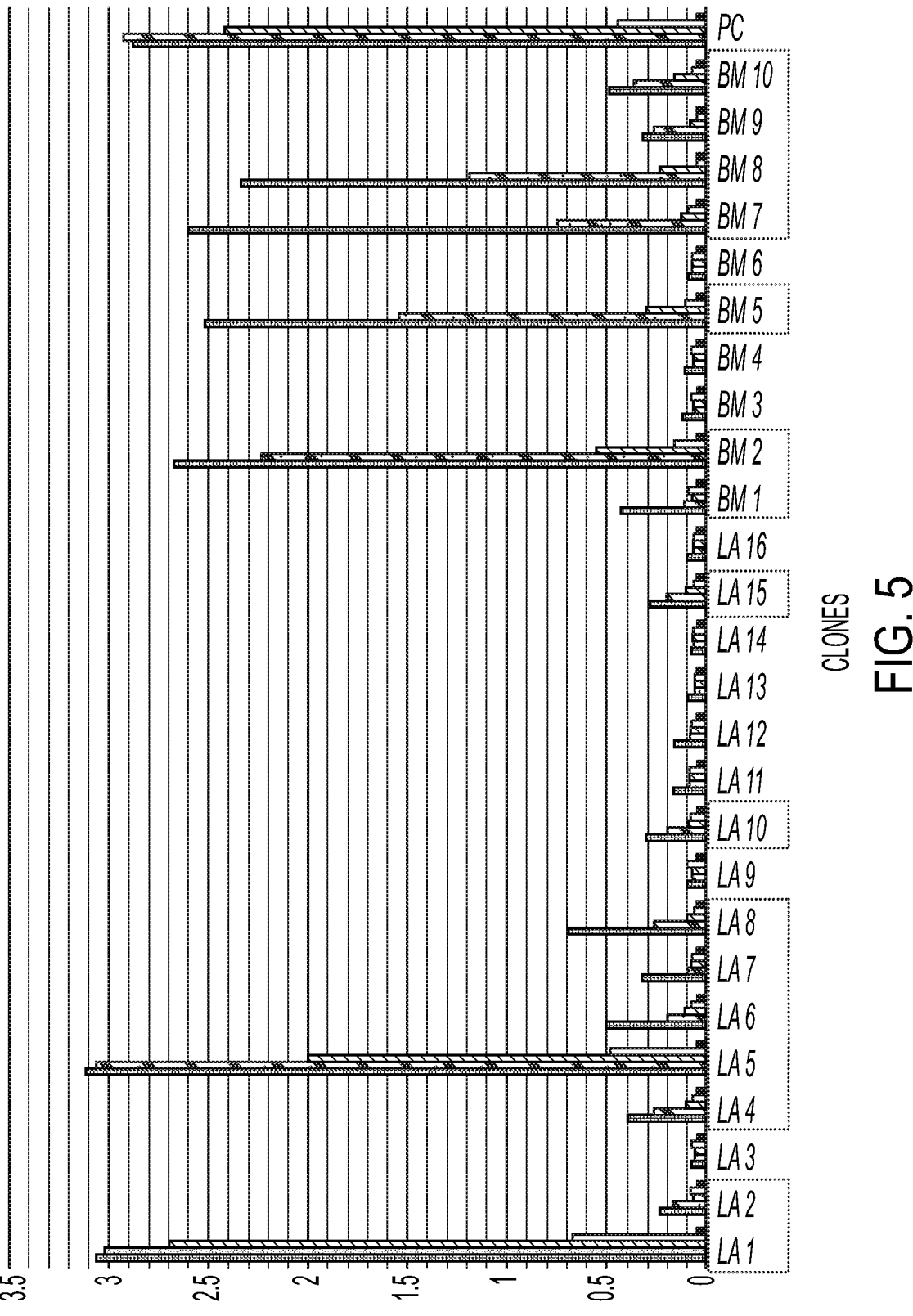
FIG. 5. Dilution assay. 26 positive clones were tested at serial dilutions as described under methods. Sixteen clones with the highest OD450 nm signal (those with squares around their names) were selected for further characterization. LA1-LA16 are clones picked at the first round of colony pickup; BM1-BM10 clones picked at the second round of colony pickup. PC is the positive control using anti-BST2 mAb (Clone 26F8) 1 ug/ml which recognizes all isoforms. Plates were coated with BST2 peptide alone. When viewing the image with the clone names on the right, the order of bars from top to bottom in a grouping of five bars for a specific clone are as follows: Blank; Dilution of 1/3375; Dilution of 1/225; Dilution of 1/15; and No Dilution.

According to the optimal serum titer observed 2 days after the last booster dose, fusion was performed on day 32. SP2/0 cells were used, as they do not secrete immunoglobulins and are sensitive to the selection media HAT (hypoxanthine-aminopterin-thymidine), which make it an ideal partner for the production of somatic cell hybrids, along with the murine lymphocytes. Within two weeks after fusion, it was able to identify 563 hybridomas in the six 96-well plates. Initial ELISA screening of the 563 colonies generated by cell fusion revealed the presence of 26 clones with antibody-containing supernatant that is reactive against the peptide of interest (BST2-D peptide). In order to choose the best candidates among the selected colonies, in terms of the productivity and the affinity of the generated mAbs, a dilution assay was performed with the positive supernatants, using ELISA technique. The 16 clones with the highest OD 450 nm signal were chosen to proceed to the next screening assays (FIG. 5).

Example 5

Cell-Based ELISA

Cell-based ELISA was used to confirm the ability of the generated hybridomas to secrete monoclonal antibodies that specifically bind to the long isoform of BST2 (BST2-D) with minimal or no binding to the medium isoform (BST2-H). For that purpose, HEK293 cell line and transfectants previously generated were utilized. In summary, HEK293 (parental): These cells demonstrate a very low expression of BST2, although it is inducible, using IFN-gamma.

HEK293 WT-BST2 (or HEK293-long): the HEK293 cells are transfected with a plasmid of the full length BST2, which is identical to the long isoform of BST2. This transfectant constitutively expresses BST2 (non-inducible). Vector containing the cDNA of the full-length BST2 was commercially available.

HEK293-H (or HEK293-medium): HEK293 cell line transfected with a plasmid that has the sequence of the medium isoform of BST2. The plasmid was obtained through collaboration with Dr. Naoko Arai's laboratory, (SBI Biotech Co., Ltd., Ginkgo Biomedical Research Institute, Kawasaki 216-0001, Japan).

Figure 6:
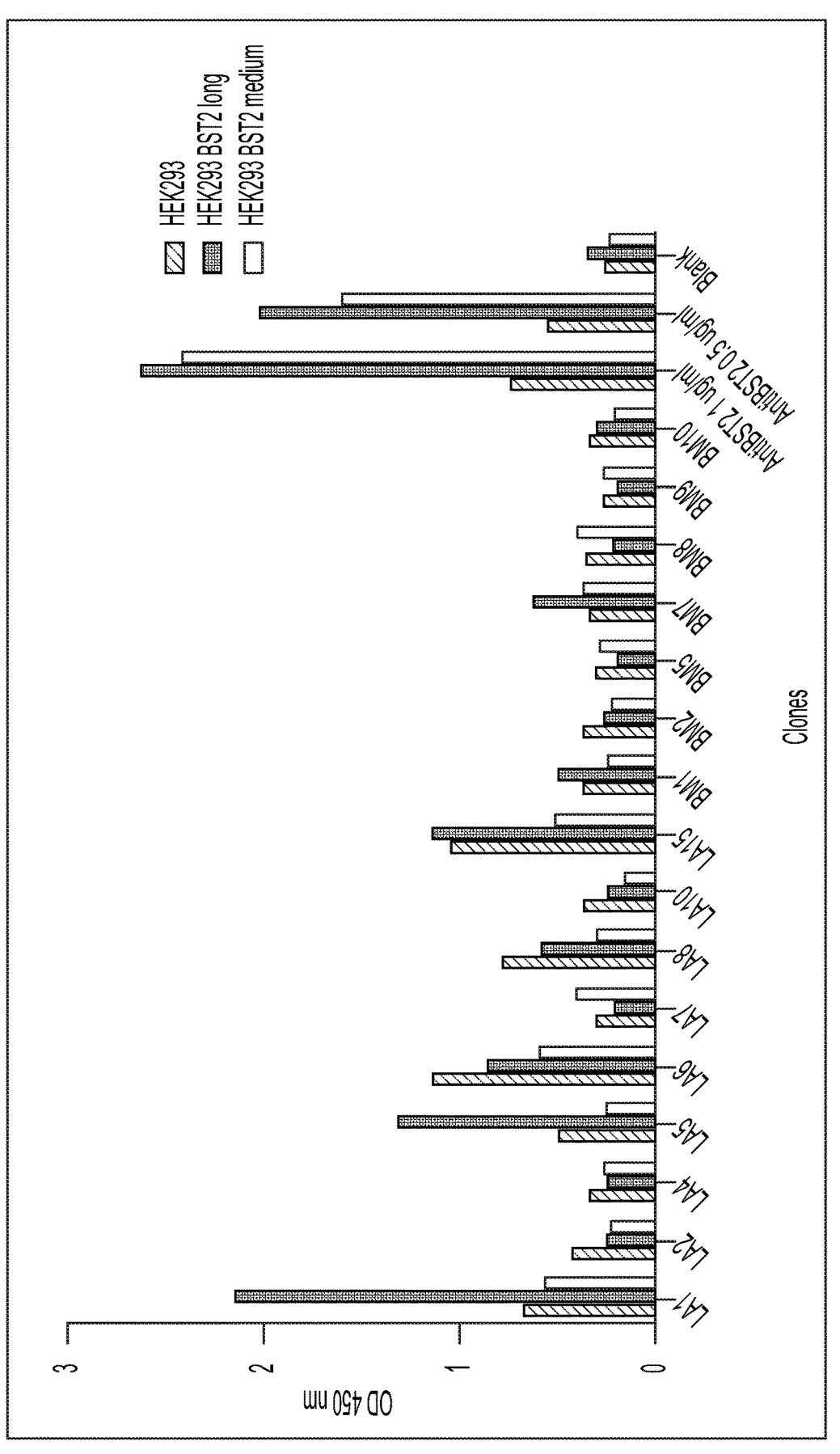
FIG. 6. Cell-Based ELISA. Screening of selected supernatants using HEK293 cell lines expressing different BST2 isoforms as indicated in the legend. Three clones (LA1, LA5 and BM7) were selected (arrows) based on specified criteria: high OD 450 signals with HEK293/BST2-WT transfectant AND low signals with HEK293/BST2-H and HEK293 parental cell lines.

Both of these transfectants were recognized by anti-BST2 (26F8) mAb (eBioscience). For a clone to be selected, its antibody-rich supernatant should demonstrate maximum binding to the HEK293 cells expressing the long isoform (HEK293 BST2-long), with minimal interactions with the parental or the HEK293 BST2-medium transfectant. The best three clones that met these criteria, reflected by their associated OD 450 signals, were chosen for the last stage of testing (FIG. 6). LA1, LA5 and BM7 showed the best combination of high OD 450 signals with HEK293 BST2-long transfectants AND low signals with HEK293 BST2-medium and HEK293 cell lines, suggesting the capabilities of these clones to produce antibodies with high affinity to the long isoform of BST2 (BST2-long), with minimal or no interaction to the other isoforms of this receptor.

Example 6

Flow Cytometry Staining of HEK293 Cell Lines

To confirm the results of the cell-based ELISA and to further characterize the generated monoclonal antibodies, staining of the HEK293 transfectants was examined by flow cytometry. Previously collected supernatants from three clones (LA1, LA5 and BM7) generated the highest staining of HEK293—long cells that express the long isoform of BST2 and a weaker (or no) staining of the HEK293 and HEK293—medium (FIG. 7).

Flow cytometry analysis revealed that LA1 supernatant stained 70.9% of HEK293—long cells, with minimal staining of HEK293—medium transfectant and the HEK293 cells (1.6 and 2.2%, respectively). Using supernatant from BM7 was associated with less staining of the HEK293—long cells (39.8%) and minimum staining of the HEK293—medium and HEK293 (0.04% and 0.24%, respectively). Compared to BM7, the LA5 supernatant was associated with a better staining of HEK293-long, with a percentage of 58.3% and comparable results for the HEK293-H and the WT (0.05% and 0.1%, respectively). Based on these results, LA5 clone demonstrated the ability to generate monoclonal antibodies with high affinity to the long isoform of BST2, with minimum interaction to the other isoform and, therefore, was selected for subcloning and purification to ensure the purity of the clone selected and the consistency of the monoclonal antibodies secreted.

After purification and the production of anti-BST2-long clone LA5, at a concentration of 1 mg/ml, flow cytometry staining was repeated with the purified LA5 mAb and compared with the commercially available anti-BST2 (clone 26F8) mAb (FIG. 8). The results from FACS staining confirmed the ability of the generated monoclonal antibody to bind selectively to the transfectant expressing the long isoform of BST2 and not the medium isoform (49.8% and 0.28%, respectively). The results also demonstrated the differences between the generated clones LA5 and 26F8 monoclonal antibodies, in term of binding to the medium isoform of BST2 (0.28% and 96.7%, respectively).

FIG. 9 summarizes the processes and the various screenings that lead to the production of purified and concentrated Ant-BST2 long (Clone LA5) monoclonal antibody.

Example 7

Antibody Isotype

After subcloning and purification of the single clone (LA5), several experiments were performed on the anti- BST2-long monoclonal antibody in order to define its characteristics. Using ELISA technique, isotype testing revealed that the isotype was a murine IgG1. The test was negative for IgM (non-significant low reactivity shown), IgG2a, IgG2b, IgG3 and IgA (FIG. 10). Given these results, IgG1 isotype, commercially available clone was selected as the isotype control for all the experiments.

Example 8

Antibody Affinity

Binding kinetics of the anti-BST2-long mAb clone LA5 was assessed, using Octet RED384 platform system. Briefly, antibodies were captured, as described under methods, by specific biosensors that bind the Fc region of the antibody. Based on prior experiments and certain standard operations procedures, 5 ug/ml was selected as the fixed concentration for the mAb. Various concentrations of the full length recombinant BST2 protein were used to assess the antibody affinity. The interaction was analyzed with a 1:1 binding model, involving both the association and the dissociation steps. A global fit of the obtained data ($R^2=0.9902$) revealed an association rate constant (ka) of $2.0+/-0.019*E+5$ 1/Ms and a dissociation rate constant (kd) of $9.21+/-0.12*E-4$ 1/s. The equilibrium dissociation constant of the LA5 mAb was $4.61+/-0.074*E-9$ M, a nanomolar value (FIG. 11).

Comparing the kinetics of both anti-BST2 clone 26F8 mAb and LA5, a difference of one order of magnitude was observed, indicating that our new generated antibody exhibits a better affinity (in the nanomolar range) than the previously generated 26F8 mAb. With a 1:1 binding model and a global fit ($R^2=0.9883$), The association rate constant (ka) was $3.86+/-0.058*E+4$ 1/Ms and the dissociation rate constant (kd) was $1.32+/-0.019*E-3$ 1/s. The equilibrium dissociation constant of the clone 26Fb mAb was $3.42+/-0.072*E-8$ molar (FIG. 12).

Example 9

Antibody Specificity

As part of the characterization of the selected antibody candidate, the inventors analyzed the specificity of the new antibody by flow cytometry staining of a cell line, constitutively expressing BST2, competing the antibody binding to the cells with a recombinant BST2 protein and an irrelevant target. Staining of MM1, a multiple myeloma cell line, was assessed at different conditions to test the binding specificity of the generated monoclonal antibodies. Anti-BST2-long (clone LA5) was pre-incubated with BST2 protein for 10 minutes, before being transferred to U-bottom wells plate containing MM1 cells. Using the BST2 protein-preincubated mAb, the staining percentage of the MM1 cells was reduced from 85.2% to 5.01% (FIG. 12). This significant reduction suggested the strong specific binding of the mAb to the BST2 protein, leaving less free mAb available for binding to BST2 receptors on the MM1 cells. Alternatively, Spartan protein, or SprT-like domain-containing protein, a human DNA-binding metalloprotease with 489 amino acid length and involved in the response to DNA replication errors (34, 35) was used as an irrelevant protein. Preincubation of this protein with the anti-BST2-long mAb for 10 minutes, before transferring to the MM1 cells, didn't change the percentage of staining, compared with the direct incubation of the mAb with MM1 cells (85.2% and 83.9%, respectively) (FIG. 13). The same pattern was observed with the use of anti-BST2 (26F8) mAb; the percentage of stained cells with no preincubated antibody was 98.2%, compared to 2.6% when preincubated with recombinant BST2, and 98.1% when preincubated with Spartan protein (FIG. 14). These results accurately indicated the ability of the generated monoclonal antibody to bind specifically to the BST2 receptors expressed on the surface of MM1 and demonstrate the comparability of the generated antibody to the commercially available anti-BST2 26F8 mAb, in term of specificity (FIG. 15).

Example 10

Flow Cytometry Staining of B Lineage and Breast Derived Cells

To analyze the expression of the long BST2 isoform in cancer and in normal tissues, as well as to test the hypothesis that the long isoform is preferentially expressed in tumor tissues, the generated mAb (anti-BST2-long clone LA5) was tested on two sets of cell lines, representing normal (but transformed) and malignant plasma cells and breast tissue. Analyzing the differences in the percentage and staining intensity (mean fluorescence) of the FACS staining between normal-transformed and malignant cell lines might indicate a preferential expression of the long isoform of BST2 receptor. Using B lymphoblastoid cell lines (B-LCL) as a surrogate for normal B lymphocytes, no differences were observed in the percentage or staining intensity (mean fluorescence) of cells, when compared to MM1 and U266 multiple myeloma cell lines. Using LA5 mAb, the percentage of cell staining for B-LCL, MM1 and U266 were 99.3, 98.6, and 96.1%, respectively. Consistently, staining cells with anti-BST2 26F8 mAb, that recognizes both isoforms, no significant differences were observed and the percentage of cell staining for B-LCL, MM1 and U266 were 99.7, 99.6, and 97.1%, respectively (FIG. 16). Consequently, preferential expression of the long isoform of BST2 could not be assessed in these cell lines, using antiBST2-long mAb. These results might also suggest a non-specific expression of the long isoform of BST2 (BST2-D) receptor, in the spectrum of B cells. Moreover, no differences have been observed in the mean fluorescence intensity of cell staining with anti-BST2-long (clone LA5) or anti-BST2 (clone 26F8) mAbs in B-LCL and U266, suggesting that the long isoform is not restricted to malignant cells but is also present in these normal-transformed cells (B-LCL) (FIG. 16). Importantly, and as it was previously observed in FIG. 13, MM1 cells showed same percentage of stained cells with both antibodies, but exhibited a difference in the mean fluorescence, suggesting that MM1 might express both the long and the medium isoforms with a lower number of surface molecules for the long isoform. To elucidate this interrogation, as well as expression of the isoforms in B-LCL and U266, double staining with mAbs conjugated to different fluorochromes and/or generation of a mAb against medium isoform, may be performed. Staining of normal B cells isolated from healthy blood donors, may also be performed.

For the B-LCL cell line (FIG. 16A), no statistically significant differences in staining were observed with the use of LA5 or 26F8 mAbs. The percentage of cell staining was 99.3% and 99.7%, respectively. Because 26F8 recognizes both isoforms, and LA5 only long isoform, it could be assumed that only the long isoform is expressed.

For the MM1 Cell line (FIG. 16B), no statistically significant differences in staining were observed with the use of LA5 or 26F8 mAbs. The percentage of cell staining was 98.6% and 99.6%, respectively. Because 26F8 recognizes both isoforms, and LA5 only long isoform, but the mean fluorescence is different, it could be assumed that the two isoforms coexist with different molecule density on the cell surface.

For the U266 Cell line (FIG. 16C), no statistically significant differences in staining were observed with the use of LA5 or 26F8 mAbs. The percentage of cell staining was 96.1% and 97.1%, respectively. Because 26F8 recognizes both isoforms, and LA5 only long isoform, it could be assumed that only the long isoform is expressed.

In contrast to the B cell lines, different patterns of cell staining were observed with these two monoclonal antibodies, when used with breast tissue cell lines. At a concentration of 1 ug/ml, LA5 mAb showed minimal binding to MCF-10A, a non-malignant but transformed epithelial breast tissue cell line, as well as T47D, MDA-MB-231 and MCF7 human breast cancer cell lines. Percentages of cell staining were 2.4%, 2.6%, 1% and 0.43%, respectively (FIG. 17). Using this same concentration, anti-BST2 clone 26F8 mAb resulted in a significantly higher staining of the MCF-10A cell line (Staining percentage of 27.7% and P value<0.05). Staining of the human breast cancer cell lines varied; upon comparison to the intensity of MCF-10A staining, nonsignificant differences were observed with MDA-MB-231 and MCF7 (percentage of staining was 28.4% and 34.7%, respectively). However, a significant difference was noticed with the staining of T47D human breast cancer cell line, with percentage of cell staining of 96.6% (FIG. 17). With these results, both monoclonal antibodies failed to prove the differential expression of BST2 isoforms in the malignant versus nonmalignant cell lines, using flow cytometry staining. However, because the short epitope target by LA5 mAb is close to the GPI (glycosylphosphatidylinositol) anchor region of the BST2 molecule, it could be considered that the epitope was destroyed during the cell preparation for FACS staining, thus not identified by LA5. Mild processing methods may be applied to demonstrate the point.

For MCF-10A cell line (FIG. 17A), statistically significant differences (P value<0.05) in staining were observed with the use of LA5 or 26F8 mAbs. The percentage of cell staining was 2.4% and 27.7%, respectively.

For MCF7 cell line (FIG. 17B), statistically significant differences (P value<0.05) in staining were observed with the use of LA5 or 26F8 mAbs. The percentage of cell staining was 0.43% and 34.7%, respectively.

For MDA-MB-231 cell line (FIG. 17C), statistically significant differences (P value<0.05) in staining were observed with the use of LA5 or 26F8 mAbs. The percentage of cell staining was 1% and 28.4%, respectively.

For T47D cell line (FIG. 17D), statistically significant differences (P value<0.05) in staining were observed with the use of LA5 or 26F8 mAbs. The percentage of cell staining was 2.6% and 96.6%, respectively.

Example 11

Immunohistochemistry Staining

In order to examine the diagnostic potential of the generated monoclonal antibodies as well as the tissue localization of the long isoform of BST2, Immunohistochemistry technique was selected. The immunohistochemistry assays on the HEK-293 transduced cells demonstrated the ability of LA5 clone mAb to stain cells expressing the long isoform of BST2, but not the other isoforms. In contrast, the use of the 26F8 mAb was associated with the staining of cells expressing any isoform of BST2 (FIG. 18). Moreover, these antibodies resulted in membranous to cytoplasmic staining, suggesting the potential of internalization of this isoform.

Through a collaboration, immunohistochemistry staining was performed on patient-derived samples of breast cancer with these two antibodies. Using formalin-fixed paraffin embedded (FFPE) tissue blocks of ductal breast carcinoma, the generated anti-BST2-long mAb (LA5) was able to stain and identify infiltrating carcinoma cells, and not the normal surrounding acinar cells. In contrast, the anti-BST2 clone 26F8 mAb stained cells expressing BST2 but did not discriminate between the malignant cells and the surrounding normal acinar cells (FIG. 19A-19B) which is expected because 26F8 stains the three isoforms (long, medium and short) since its epitope is common to the three.

Within the breast ductal system, immunohistochemistry assays revealed the ability of the LA5 mAb to bind and stain specifically the malignant cells and to distinguish the surrounding normal ducts. On the other hand, the 26F8 mAb could not differentiate between the normal and malignant ducts, with a subsequent positive staining of cells in these two structures (FIGS. 20A-20B). This finding suggested that the short epitope of LA5, specific and present in the long isoform, exposed during the tissue fixation and processing, allows LA5 to recognize tumor cells but not normal cells. In specific embodiments, this indicates that (1) long isoform is not expressed in normal cells; and 2) LA5 is specifically staining tumor cells.

Example 12

BST2 Silencing Via shRNA

In order to explore some of the BST2 roles in carcinogenesis in breast cancer, a loss of function approach with BST2-targeting short hairpin RNA (shRNA) was used. To examine the efficiency of this approach, flowcytometry staining of cell lines was performed. By analyzing the percentage of cell staining among the non-transduced T47D cell line (T47D WT), T47D cell line with a non-silenced transduction (T47D-NS), and T47D cell line with BST2-silenced transduction (T47D BST2-Silenced), there was confirmation of a subpopulation of cells that were GFP-positive and APC-negative. The green fluorescent protein (GFP) indicates the efficient lentiviral transduction, while using secondary antibodies conjugated with Allophycocyanin (APC) that interact with anti-BST2 primary antibodies, indicates the presence of BST2 membrane receptors (FIGS. 21A-21F). Consequently, the GFP positive APC negative cells were considered BST2—silenced cells. Those cells were collected, via cell sorting, expanded and studied by comparison to T47D WT (GFP negative, APC positive cells) and T47D NS (GFP positive, APC positive cells).

Example 13

Cell Viability Assay

In order to examine the impact of silencing BST2 on the viability of T47D, CellTiter-Glo viability assay was performed. A statistically significant reduction in viability was observed with BST2 Silencing (P value=0.033), compared to the viability observed in T47D-WT and T47D-non silenced control. FIG. 22 demonstrates the mean and 95% confidence intervals of the luminescence captured from each cell line.

Example 14

Cell Proliferation Assay

In order to examine the impact of silencing BST2 on the viability of T47D, XTT cell proliferation assay was performed. No statistically significant changes in proliferation was observed with BST2 Silencing (P value=0.6), compared to the proliferation observed in T47D-WT and T47D-non silenced control. FIG. 23 demonstrates the mean and 95% confidence intervals of the absorbance recorded from each cell line.

Example 15

Protein Expression in T47D Cell Lines Pre- and Post BST2 Silencing

To define the cellular adaptive responses to silencing BST2 gene and to understand a possible pathway for the reduced viability post BST2 silencing, cellular protein expression was explored. The data received from the Reverse Phase Protein Array (RPPA) assessed the relative protein expression of 466 genes in a non-transduced T47D cell line (T47D-WT), T47D cell line with a nonsilenced transduction (T47D-NS), and T47D cell line with BST2 silenced transduction (T47D BST2-Silenced). After data cleaning and analysis of the values, the relative protein expression of 99 genes showed changes after silencing BST2. The log 2 values of the normalized linear data were median-centered and used to generate a heatmap to visualize the changes in the relative protein expression observed after BST2 silencing, compared to T47D WT and T47D-NS (FIG. 24).

By analyzing the normalized linear values associated with each protein, there was a statistically significant upregulation (P value<0.05) of the following genes with the silencing of BST2: MAPK1/MAPK3, HES1, FN1 and STAT3 (FIG. 25). In contrast, no statistically significant downregulation of genes was observed with BST2 silencing (FIG. 26).

Example 16

Significance of Certain Embodiments of the Disclosure

In particular embodiments, analysis of the expression of the different isoforms of BST2 in various cells and tissues provides a better understanding of the role(s) that this molecule plays in carcinogenesis and provides an opportunity for characterizing a target for a diagnostic or a therapeutic mAb useful in the clinical.

The present disclosure encompasses a unique mAb that targets the long isoform of BST2 (described in JP2004173767). Prior to the selection and production of the anti-BST2-long mAb, 563 clones were subjected to extensive screening studies that consecutively narrowed down the list of the potential candidates to a single clone, referred to as LA5. Although an initial list of the candidates included three clones (LA1, LA5 and BM7), the selection of LA5 was based on a combination of the specificity and the affinity of the secreted mAb to bind to the long isoform of BST2 expressed by the HEK293—long transfectant and not to the transfectant expressing the medium isoform of BST2, i.e. HEK293—medium. Using anti-BST2-long (clone LA5) mAb, the flow cytometry staining of HEK293 transfectants demonstrated minimal binding to the medium isoform. In specific aspects, this could be attributed to the fact that the sequence of the peptide used for mice immunization partially overlapped, although minimally, with the amino acid sequence of the medium isoform. Upon designing the peptide for immunization, targeting the extracellular domain of the long isoform of BST2 and maintaining an optimal length (for the purpose of immunogenicity) were taken into consideration. While not part of the main antigenic determinant of the peptide (RENQVLSVRI; SEQ ID NO:4), the first five amino acids of the peptide used for the immunization (at the amino terminal) in some embodiments could be responsible for the minimal reactivity of the mAb against the medium isoform of the BST2. Regardless, LA5 mAb demonstrated superiority in selectively binding to the long isoform of BST2 when compared to anti-BST2 clone 26F8 mAb, a previously developed antibody that recognizes all isoforms.

The kinetic assays performed on LA5 and 26F8 mAbs showed comparable results in terms of the affinity of the mAbs to the BST2 protein. The nano-molar value of the equilibrium dissociation constant (KD) measured for the LA5 mAb, an important criterion for the selection of a good antibody, indicates a high affinity to BST2 molecules. This feature allows the utilization of LA5 mAb as a valuable diagnostic tool to detect the expression of the long isoform of BST2 in various in-vitro assays and immunohistochemistry staining. Importantly, this property of an antibody (nano-molar value for KD constant), indicates that could be considered as a potential therapeutic candidate. Measuring the affinity of LA5 mAb interaction with BST2 receptors expressed on cells, instead of BST2 purified protein, provides insights about the kinetics of this interaction. Results from the specificity assays strongly indicate the high specificity of clone LA5 mAb to bind to its target, the long isoform of BST2.

In order to further explore some of the BST2 roles in carcinogenesis in breast malignancy, a loss of function approach with BST2-targeting short hairpin RNA (shRNA) was used. Silencing BST2 was associated with a statistically significant reduction in the viability of T47D cell line, while no variation in the proliferative ability was observed. While Cai et al. used a gain-of-function approach to study BST2 in breast cancer, they noticed an increase in the S-phase cell population (an indicator of proliferation) with the introduction of BST2 to MDA-MB-231 breast cancer cell line (20). In another study, Mahauad-Fernandez reported a reduced viability of both MDA-MB-231 cell line and circulating tumor cells with the suppression of BST2, by rendering these cells susceptible to anoikis (21).

Variations in gene expression as a consequence of BST2 silencing were studied in the T47D cell line, with a goal to define the cellular adaptive response. Among the 466 genes analyzed by RPPA, only 4 genes demonstrated statistically significant changes. Noteworthy, STAT3 demonstrated a significant upregulation following BST2 silencing in the assays. Signal transducer and activator of transcription 3 (STAT3) has many physiological roles, in relation with several cytokines and growth factors, as well as carcinogenic roles, especially in tumor initiation and progression. In their study of STAT3 in breast cancer, Segatto et al. observed STAT3 signaling in breast cancer cells in response to treatment. This STAT3 activation mediates survival and dormancy state (44). While STAT3 overexpression with BST2 silencing might be nonspecific, it clearly indicates the significant role of BST2 in breast tumorigenesis. It could also point out to a possible tumor resistant mechanism should the anti-BST2 monoclonal antibodies used for the treatment of breast cancer. Other significantly overexpressed genes after BST2 silencing were MAPK1/MAPK3 and HES1. Si et al. found that overexpression of MAPK1 in breast cancer cells was associated with enhanced proliferation and chemotherapeutic resistance (45). Hairy and enhancer of split homolog-1 (HES1), a transcriptional repressor, has multiple physiological roles in cellular differentiation, apoptosis and cell cycle arrest and overexpression was found in different malignancies, including lung, ovarian and colorectal cancers. Li et al. reported an enhanced survival and proliferation of MCF7 breast cancer cell line with the induced expression of HES1 (46). These findings might explain why no changes in the proliferation of T47D cells were observed with BST2 silencing. Lastly, FN1, a glycoprotein involved in cellular adhesion and migration, was significantly overexpressed after silencing BST2. A study conducted by Yang et al. reported an enhanced invasion and migration capabilities of MCF7 breast cancer cell lines with the upregulation of FN1, as well as an increased resistance to chemotherapy (doxorubicin) (47). FN1 upregulation in T47D cell line may suggest a more aggressive behavior in response to silencing BST2. To summarize, the upregulation of these genes demonstrates the adaptive response that breast cancer cells might reveal with targeting BST2. It is also an example of the different survival mechanisms that the tumor cells may use should a critical pathway get compromised.

Example 17

Example of Antibody Protocol and Immunohistochemistry Studies on Commercial Tissue Microarrays Immunohistochemistry studies were performed on two examples of tissue microarrays using specimen from Novus Biologicals (Centennial, CO): #72070 tissue microarray that included 60 core samples (breast tumor and normal), and #78070 tissue microarray that included 8 specimen (spleen, sternum, kidney, thymus, liver, appendix, normal lymph node. The studies utilized the commercially available anti-BST2 (Clone 26F8) monoclonal antibody anti-BST2 long isoform (Clone LA5) of the present disclosure.

Antigen retrieval conditions included the following, as an example. To perform the antigen retrieval, the following was used: Epitope Retrieval 1 (ER1) citrate-based buffer (pH 6.0) is denominated as H1. Analysis methods included use of the analysis software Halo (HALO 3.1.1076.449), and the analyzable area of the tumor, normal epithelial cells, stroma or parenchymal, and mesenchymal were annotated manually. Individual algorithms were set by training with different antibodies. The cytoplasm positive in the selected areas were scored using the examples of algorithms that were set, and intensity (0, 1+, 2+, or 3+) and extension (0-100%) were recorded, and the total percentages were summed (FIG. 27).

FIGS. 28-31 demonstrate examples of immunohistochemistry results. In particular, commercial (Mab 26F8) (FIG. 28 or 30) or novel anti-BST2 (Mab LA5) (FIG. 29 or 31) antibodies of the disclosure were exposed to tissue microarrays of normal breast (FIG. 28-29) or BIDC (FIGS. 30-31) samples. The figures are representative of one sample out of 50 breast infiltrating ductal carcinoma (BIDC) tissue microarray, or one sample out of 8 normal breast tissues. The percentage of tumors recognized by Clone 26F8 (34%) is slightly lower than the percentage stained by Clone LA5, indicating a higher sensitivity for Clone LA5 to identify the tumor cells. The intensity of staining is also higher using MAb LA5 (FIG. 31).

FIG. 27, lower panel, shows the table with normal tissues stained with both MAb 26F8 and MAb LA5. Importantly, 100% of normal mesenchymal and blood vessels are stained with 26F8 and only 14.3% with LA5. In specific embodiments, the long isoform expression in tumors, but low or negative in normal tissues, indicates useful utilization of the antibody for clinical application. In specific embodiments, LA1 and BM7 antibodies referred to elsewhere herein are utilized to show discrimination between malignant and normal tissues and with a different and higher affinity than LA5, in some embodiments.

REFERENCES

All publications cited herein are hereby incorporated by reference in their entirety herein.

1. Andrew A J, Miyagi E, Kao S, Strebel K. The formation of cysteine-linked dimers of BST-2/tetherin is important for inhibition of HIV-1 virus release but not for sensitivity to Vpu. Retrovirology. 2009; 6:80. Epub 2009/09/10. doi: 10.1186/1742-4690-6-80. PubMed PMID: 19737401; PMCID: PMC2754425.
2. Goto T, Kennel S J, Abe M, Takishita M, Kosaka M, Solomon A, Saito S. A novel membrane antigen selectively expressed on terminally differentiated human B cells. Blood. 1994; 84(6):1922-30. Epub 1994/09/15. PubMed PMID: 8080996.
3. Ishikawa J, Kaisho T, Tomizawa H, Lee B O, Kobune Y, Inazawa J, Oritani K, Itoh M, Ochi T, Ishihara K, et al. Molecular cloning and chromosomal mapping of a bone marrow stromal cell surface gene, BST2, that may be involved in pre-B-cell growth. Genomics. 1995; 26(3):527-34. Epub 1995/04/10. doi: 10.1016/0888-7543(95)80171-h. PubMed PMID: 7607676.
4. Neil S J, Zang T, Bieniasz P D. Tetherin inhibits retrovirus release and is antagonized by HIV-1 Vpu. Nature. 2008; 451(7177):425-30. Epub 2008/01/18. doi: 10.1038/nature06553. PubMed PMID: 18200009.
5. OriGene Technologies I. BST2 Mouse Monoclonal Antibody [Clone I D: 2E2] 2018 [Dec. 15, 2019]. Available from: https://www.origene.com/catalog/antibodies/primary-antibodies/ta337180/bst2-mouse-monoclonal-antibody-clone-id-2e2.
6. Billcliff P G, Gorleku O A, Chamberlain L H, Banting G. The cytosolic N-terminus of CD317/tetherin is a membrane microdomain exclusion motif. Biology open. 2013; 2(11):1253-63. Epub 2013/11/19. doi: 10.1242/bio.20135793. PubMed PMID: 24244863; PMCID: PMC3828773.
7. Dube M, Bego M G, Paquay C, Cohen E A. Modulation of HIV-1-host interaction: role of the Vpu accessory protein. Retrovirology. 2010; 7:114. Epub 2010/12/24. doi: 10.1186/1742-4690-7-114. PubMed PMID: 21176220; PMCID: PMC3022690.
8. Kupzig S, Korolchuk V, Rollason R, Sugden A, Wilde A, Banting G. Bst-2/HM1.24 is a raft-associated apical membrane protein with an unusual topology. Traffic (Copenhagen, Denmark). 2003; 4(10):694-709. Epub 2003/09/06. doi: 10.1034/j.1600-0854.2003.00129.x. PubMed PMID: 12956872.
9. Schroder K, Hertzog P J, Ravasi T, Hume D A. Interferon-gamma: an overview of signals, mechanisms and func-
tions. Journal of leukocyte biology. 2004; 75(2):163-89. Epub 2003/10/04. doi: 10.1189/jlb.0603252. PubMed PMID: 14525967.
10. Yoo H, Park S H, Ye S K, Kim M. IFN-gamma-induced BST2 mediates monocyte adhesion to human endothelial cells. Cellular immunology. 2011; 267(1):23-9. Epub 2010/11/26. doi: 10.1016/j.cellimm.2010.10.011. PubMed PMID: 21094940.
11. Takeda E, Nakagawa S, Nakaya Y, Tanaka A, Miyazawa T, Yasuda J. Identification and functional analysis of three isoforms of bovine BST-2. PloS one. 2012; 7(7):e41483. Epub 2012/08/23. doi: 10.1371/journal.pone.0041483. PubMed PMID: 22911799; PMCID: PMC3401110.
12. Cao W, Bover L. Signaling and ligand interaction of ILT7: receptor-mediated regulatory mechanisms for plasmacytoid dendritic cells. Immunological reviews. 2010; 234(1):163-76. Epub 2010/03/03. doi: 10.1111/j.0105-2896.2009.00867.x. PubMed PMID: 20193018; PMCID: PMC2919054.
13. Urata S, Kenyon E, Nayak D, Cubitt B, Kurosaki Y, Yasuda J, de la Tone J C, McGavern D B. BST-2 controls T cell proliferation and exhaustion by shaping the early distribution of a persistent viral infection. PLoS pathogens. 2018; 14(7):e1007172. Epub 2018/07/22. doi: 10.1371/journal.ppat.1007172. PubMed PMID: 30028868; PMCID: PMC6080785.
14. Arias J F, Heyer L N, von Bredow B, Weisgrau K L, Moldt B, Burton D R, Rakasz E G, Evans D T. Tetherin antagonism by Vpu protects HIV-infected cells from antibody-dependent cell-mediated cytotoxicity. Proceedings of the National Academy of Sciences of the United States of America. 2014; 111(17):6425-30. Epub 2014/04/16. doi: 10.1073/pnas.1321507111. PubMed PMID: 24733916; PMCID: PMC4035966.
15. Edgar J R, Manna P T, Nishimura S, Banting G, Robinson M S. Tetherin is an exosomal tether. eLife. 2016; 5. Epub 2016/09/23. doi: 10.7554/eLife.17180. PubMed PMID: 27657169; PMCID: PMC5033606.
16. Erikson E, Adam T, Schmidt S, Lehmann-Koch J, Over B, Goffinet C, Harter C, Bekeredjian-Ding I, Sertel S, Lasitschka F, Keppler O T. In vivo expression profile of the antiviral restriction factor and tumor-targeting antigen CD317/BST-2/HM1.24/tetherin in humans. Proceedings of the National Academy of Sciences of the United States of America. 2011; 108(33):13688-93. Epub 2011/08/03. doi: 10.1073/pnas.1101684108. PubMed PMID: 21808013; PMCID: PMC3158195.
17. Atlas T H P. HUMAN PROTEIN ATLAS SUMMARY 2019 [Dec. 26, 2019]; Version 19.1:[Available from: https://www.proteinatlas.org/ENSG00000130303-BST2.
18. Wang W, Nishioka Y, Ozaki S, Jalili A, Abe S, Kakiuchi S, Kishuku M, Minakuchi K, Matsumoto T, Sone S. HM1.24 (CD317) is a novel target against lung cancer for immunotherapy using anti-HM1.24 antibody. Cancer immunology, immunotherapy: CII. 2009; 58(6):967-76. Epub 2008/11/04. doi: 10.1007/s00262-008-0612-4. PubMed PMID: 18979097.
19. Kampf C, Olsson I, Ryberg U, Sjostedt E, Ponten F. Production of tissue microarrays, immunohistochemistry staining and digitalization within the human protein atlas. Journal of visualized experiments: JoVE. 2012(63). Epub 2012/06/13. doi: 10.3791/3620. PubMed PMID: 22688270; PMCID: PMC3468196.
20. Cai D, Cao J, Li Z, Zheng X, Yao Y, Li W, Yuan Z. Up-regulation of bone marrow stromal protein 2 (BST2) in breast cancer with bone metastasis. BMC cancer. 2009;

9:102. Epub 2009/04/03. doi: 10.1186/1471-2407-9-102. PubMed PMID: 19338666; PMCID: PMC2674058.

21. Mahauad-Fernandez W D, Naushad W, Panzner T D, Bashir A, Lal G, Okeoma C M. BST-2 promotes survival in circulation and pulmonary metastatic seeding of breast cancer cells. Scientific reports. 2018; 8(1):17608. Epub 2018/12/06. doi: 10.1038/s41598-018-35710-y. PubMed PMID: 30514852; PMCID: PMC6279795.

22. Mukai S, Oue N, Oshima T, Mukai R, Tatsumoto Y, Sakamoto N, Sentani K, Tanabe K, Egi H, Hinoi T, Ohdan H, Yasui W. Overexpression of Transmembrane Protein BST2 is Associated with Poor Survival of Patients with Esophageal, Gastric, or Colorectal Cancer. Annals of surgical oncology. 2017; 24(2):594-602. Epub 2016/02/03. doi: 10.1245/s10434-016-5100-z. PubMed PMID: 26832883.

23. Yang L L, Wu L, Yu G T, Zhang W F, Liu B, Sun Z J. CD317 Signature in Head and Neck Cancer Indicates Poor Prognosis. Journal of dental research. 2018; 97(7): 787-94. Epub 2018/02/28. doi: 10.1177/0022034518758604. PubMed PMID: 29486141.

24. Kuang C M, Fu X, Hua Y J, Shuai W D, Ye Z H, Li Y, Peng Q H, Li Y Z, Chen S, Qian C N, Huang W, Liu R Y. BST2 confers cisplatin resistance via NF-kappaB signaling in nasopharyngeal cancer. Cell death & disease. 2017; 8(6):e2874. Epub 2017/06/16. doi: 10.1038/cddis.2017.271. PubMed PMID: 28617432; PMCID: PMC5520926.

25. Harada T, Ozaki S. Targeted therapy for HM1.24 (CD317) on multiple myeloma cells. BioMed research international. 2014; 2014:965384. Epub 2014/08/22. doi: 10.1155/2014/965384. PubMed PMID: 25143955; PMCID: PMC4124849.

26. Russell Burke M L, Dorian LaTocha, Tomohide Yamazaki, Koji Ishida, Naoko Arai, Stephen Spurgeon. Identification of BST2 as a Potential Therapeutic Target in B Cell Malignancies Including Chronic Lymphocytic Leukemia and Mantle Cell Lymphoma. Clinical Lymphoma, Myeloma & Leukemia. 2011; 11, Supplement 2:S192-S3. Epub Oct. 8, 2011. doi: https://doi.org/10.1016/j.clml.2011.09.085.

27. Jun Ohkawa, Kamogawa Y. Methods for suppressing activity of activated interferon-producing cells2005; U.S. Pat. No. 8,435,530B2.

28. Cocka L J, Bates P. Identification of alternatively translated Tetherin isoforms with differing antiviral and signaling activities. PLoS pathogens. 2012; 8(9):e1002931. Epub 2012/10/03. doi: 10.1371/journal.ppat.1002931. PubMed PMID: 23028328; PMCID: PMC3460627.

29. Karin M. Nuclear factor-kappaB in cancer development and progression. Nature. 2006; 441(7092):431-6. Epub 2006/05/26. doi: 10.1038/nature04870. PubMed PMID: 16724054.

30. Cao W, Rosen D B, Ito T, Bover L, Bao M, Watanabe G, Yao Z, Zhang L, Lanier L L, Liu Y J. Plasmacytoid dendritic cell-specific receptor ILT7-Fc epsilonRI gamma inhibits Toll-like receptor-induced interferon production. The Journal of experimental medicine. 2006; 203(6): 1399-405. Epub 2006/06/01. doi: 10.1084/jem.20052454. PubMed PMID: 16735691; PMCID: PMC2118323.

31. Cao W, Bover L, Cho M, Wen X, Hanabuchi S, Bao M, Rosen D B, Wang Y H, Shaw J L, Du Q, Li C, Arai N, Yao Z, Lanier L L, Liu Y J. Regulation of TLR7/9 responses in plasmacytoid dendritic cells by BST2 and ILT7 receptor interaction. The Journal of experimental medicine.

2009; 206(7):1603-14. Epub 2009/07/01. doi: 10.1084/jem.20090547. PubMed PMID: 19564354; PMCID: PMC2715090.

32. Bio F. High throughput Octet HTX and Octet RED384 Systems 2020 [Mar. 5, 2020]. Available from: https://www.fortebio.com/products/label-free-bli-detection/high-throughput-octet-systems.

33. Kamala T. Hock immunization: a humane alternative to mouse footpad injections. Journal of immunological methods. 2007; 328(1-2):204-14. Epub 2007/09/07. doi: 10.1016/j.jim.2007.08.004. PubMed PMID: 17804011; PMCID: PMC2464360.

34. Lopez-Mosqueda J, Maddi K, Prgomet S, Kalayil S, Marinovic-Terzic I, Terzic J, Dikic I. SPRTN is a mammalian DNA-binding metalloprotease that resolves DNA-protein crosslinks. eLife. 2016; 5. Epub 2016/11/18. doi: 10.7554/eLife.21491. PubMed PMID: 27852435; PMCID: PMC5127644.

35. Complete sequencing and characterization of 21,243 full-length human cDNAs [Internet]2004 [cited Mar. 9, 2020]. Available from: https://www.ncbi.nlm.nih.gov/protein/NP_114407.3.

36. Buss N A, Henderson S J, McFarlane M, Shenton J M, de Haan L. Monoclonal antibody therapeutics: history and future. Current opinion in pharmacology. 2012; 12(5): 615-22. Epub 2012/08/28. doi: 10.1016/j.coph.2012.08.001. PubMed PMID: 22920732.

37. Kimiz-Gebologlu I, Gulce-Iz S, Biray-Avci C. Monoclonal antibodies in cancer immunotherapy. Molecular biology reports. 2018; 45(6):2935-40. Epub 2018/10/13. doi: 10.1007/s11033-018-4427-x. PubMed PMID: 30311129.

38. Pento J T. Monoclonal Antibodies for the Treatment of Cancer. Anticancer research. 2017; 37(11):5935-9. Epub 2017/10/25. doi: 10.21873/anticanres.12040. PubMed PMID: 29061772.

39. Beckman R A, Weiner L M, Davis H M. Antibody constructs in cancer therapy: protein engineering strategies to improve exposure in solid tumors. Cancer. 2007; 109(2):170-9. Epub 2006/12/13. doi: 10.1002/cncr.22402. PubMed PMID: 17154393.

40. Stern M, Herrmann R. Overview of monoclonal antibodies in cancer therapy: present and promise. Critical reviews in oncology/hematology. 2005; 54(1):11-29. Epub 2005/03/23. doi: 10.1016/j.critrevonc.2004.10.011. PubMed PMID: 15780905.

41. Adams G P, Schier R, McCall A M, Simmons H H, Horak E M, Alpaugh R K, Marks J D, Weiner L M. High affinity restricts the localization and tumor penetration of single-chain fv antibody molecules. Cancer research. 2001; 61(12):4750-5. Epub 2001/06/19. PubMed PMID: 11406547.

42. Jain R K, Baxter L T. Mechanisms of heterogeneous distribution of monoclonal antibodies and other macromolecules in tumors: significance of elevated interstitial pressure. Cancer research. 1988; 48(24 Pt 1):7022-32. Epub 1988/12/15. PubMed PMID: 3191477.

43. Hussain T, Mulherkar R. Lymphoblastoid Cell lines: a Continuous in Vitro Source of Cells to Study Carcinogen Sensitivity and DNA Repair. International journal of molecular and cellular medicine. 2012; 1(2):75-87. Epub 2012/04/01. PubMed PMID: 24551762; PMCID: PMC3920499.

44. Segatto I, Baldassarre G, Belletti B. STAT3 in Breast Cancer Onset and Progression: A Matter of Time and Context. International journal of molecular sciences.

2018; 19(9). Epub 2018/09/21. doi: 10.3390/ijms19092818. PubMed PMID: 30231553; PMCID: PMC6163512.
45. Si W, Shen J, Du C, Chen D, Gu X, Li C, Yao M, Pan J, Cheng J, Jiang D, Xu L, Bao C, Fu P, Fan W. A miR-20a/MAPK1/c-Myc regulatory feedback loop regulates breast carcinogenesis and chemoresistance. Cell death and differentiation. 2018; 25(2):406-20. Epub 2017/11/11. doi: 10.1038/cdd.2017.176. PubMed PMID: 29125598; PMCID: PMC5762853.
46. Li X, Cao Y, Li M, Jin F. Upregulation of HES1 Promotes Cell Proliferation and Invasion in Breast Cancer as a Prognosis Marker and Therapy Target via the AKT Pathway and EMT Process. Journal of Cancer. 2018; 9(4):757-66. Epub 2018/03/21. doi: 10.7150/jca.22319. PubMed PMID: 29556333; PMCID: PMC5858497.
47. Yang X, Hu Q, Hu L X, Lin X R, Liu J Q, Lin X, Dinglin X X, Zeng J Y, Hu H, Luo M L, Yao H R. miR-200b regulates epithelial-mesenchymal transition of chemoresistant breast cancer cells by targeting FN1. Discovery medicine. 2017; 24(131):75-85. Epub 2017/10/04. PubMed PMID: 28972876.

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. An antibody or an antigen-binding portion thereof comprising:

(a) three heavy chain CDRs (CDR-H) and three light chain CDRs (CDR-L), wherein: CDR-H1 comprises the amino acid sequence as set forth in SEQ ID NO: 8 (GFNIKDYY), CDR-H2 comprises the amino acid sequence as set forth in SEQ ID NO: 10 (IDPENGDT), CDR-H3 comprises the amino acid sequence as set forth in SEQ ID NO: 12 (KRGD), CDR-L1 comprises the amino acid sequence as set forth in SEQ ID NO: 17 (QSIVHSNGNTY), CDR-L2 comprises the amino acid sequence of KVS, and CDR-L3 comprises the amino acid sequence as set forth in SEQ ID NO: 20 (FQGSHAPFT); and wherein said antibody or antigen-binding portion thereof binds to BST2;

(b) three heavy chain CDRs (CDR-H) and three light chain CDRs (CDR-L), wherein: CDR-H1 comprises the amino acid sequence as set forth in SEQ ID NO: 38 (GYTFTEDT), CDR-H2 comprises the amino acid sequence as set forth in SEQ ID NO: 40 (INPNKGGT), CDR-H3 comprises the amino acid sequence as set forth in SEQ ID NO: 42 (ATLVDY), CDR-L1 comprises the amino acid sequence as set forth in SEQ ID NO: 30 (QNVGTN), CDR-L2 comprises the amino acid sequence of SAS, and CDR-L3 comprises the amino acid sequence as set forth in SEQ ID NO: 33 (QQYNSYPLT); or (c) three heavy chain CDRs (CDR-H) and three light chain CDRs (CDR-L), wherein: CDR-H1 comprises the amino acid sequence as set forth in SEQ ID NO: 55 (GFSLSTSGVG), CDR-H2 comprises the amino acid sequence as set forth in SEQ ID NO: 57 (IWWDDDE), CDR-H3 comprises the amino acid sequence as set forth in SEQ ID NO: 59 (ARRYYGDAMDY), CDR-L1 comprises the amino acid sequence as set forth in SEQ ID NO: 47 (QSLVHSNGHTY), CDR-L2 comprises the amino acid sequence of KVS, and CDR-L3 comprises the amino acid sequence as set forth in SEQ ID NO: 50 (SQSTHVPYT).

2. The antibody or an antigen-binding portion thereof of claim 1, wherein the antibody or an antigen-binding portion thereof comprises a heavy chain variable region that comprises an amino acid sequence with at least 80% sequence identity to SEQ ID NO:7 and a light chain variable region that comprises an amino acid sequence with at least 80% sequence identity to SEQ ID NO: 16.

3. The antibody of claim 1, wherein the antibody is a monoclonal antibody.

4. An engineered antigen receptor or a bispecific or a multi-specific antibody comprising the antibody or an antigen-binding portion thereof of claim 1.

5. An engineered antigen receptor comprising a scFv, wherein the scFv comprises the antigen-binding portion of claim 1.

6. A composition comprising a scFv, wherein the scFv comprises the antigen-binding portion of claim 1.

7. An immune cell comprising the engineered antigen receptor of claim 5.

8. The cell of claim 7, wherein the immune cell is a T cell, NK cell, or NKT cell.

9. A method of detecting BST2-expressing cells in a tissue or plurality of cells that are cancerous or suspected of being cancerous, comprising the step of subjecting the tissue or plurality of cells to an effective amount of the antibody of claim 1, wherein the antibody binds BST2 in the tissue or plurality of cells.

10. The method of claim 9, wherein the tissue or plurality of cells comes from an individual that is known to have cancer or is suspected of having cancer or wherein the tissue or plurality of cells comes from an individual that is known to have metastatic cancer or is suspected of having metastatic cancer.

11. A method of measuring BST2 in tissue or cells from an individual that has cancer or that is suspected of having cancer, comprising the step of measuring BST2 from the tissue or cells with an effective amount of the antibody of claim 1.

* * * * *

SEQUENCE LISTING

```
<160> NUMBER OF SEQ ID NOS: 61

<210> SEQ ID NO 1
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Val Glu Arg Leu Arg Arg Glu Asn Gln Val Leu Ser Val Arg Ile
1               5                   10                  15

Ala Asp Lys Lys Tyr Tyr Pro Ser
            20

<210> SEQ ID NO 2
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Glu Asn Gln Val Leu Ser Val Arg Ile Ala Asp Lys Lys Tyr Tyr
1               5                   10                  15

Pro Ser

<210> SEQ ID NO 3
<211> LENGTH: 180
<212> TYPE: PRT
<213> ORGANISM: Homo sapiens

<400> SEQUENCE: 3

Met Ala Ser Thr Ser Tyr Asp Tyr Cys Arg Val Pro Met Glu Asp Gly
1               5                   10                  15

Asp Lys Arg Cys Lys Leu Leu Leu Gly Ile Gly Ile Leu Val Leu Leu
            20                  25                  30

Ile Ile Val Ile Leu Gly Val Pro Leu Ile Ile Phe Thr Ile Lys Ala
            35                  40                  45
```

```
Asn Ser Glu Ala Cys Arg Asp Gly Leu Arg Ala Val Met Glu Cys Arg
    50              55              60

Asn Val Thr His Leu Leu Gln Gln Glu Leu Thr Glu Ala Gln Lys Gly
65              70              75              80

Phe Gln Asp Val Glu Ala Gln Ala Ala Thr Cys Asn His Thr Val Met
            85              90              95

Ala Leu Met Ala Ser Leu Asp Ala Glu Lys Ala Gln Gly Gln Lys Lys
            100             105             110

Val Glu Glu Leu Glu Gly Glu Ile Thr Thr Leu Asn His Lys Leu Gln
        115             120             125

Asp Ala Ser Ala Glu Val Glu Arg Leu Arg Arg Glu Asn Gln Val Leu
    130             135             140

Ser Val Arg Ile Ala Asp Lys Lys Tyr Tyr Pro Ser Ser Gln Asp Ser
145             150             155             160

Ser Ser Ala Ala Ala Pro Gln Leu Leu Ile Val Leu Leu Gly Leu Ser
            165             170             175

Ala Leu Leu Gln
        180

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Glu Asn Gln Val Leu Ser Val Arg Ile
1               5               10

<210> SEQ ID NO 5
<211> LENGTH: 1100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
tggagtatca acgcagagta catggggata tgaacactgt tttctctaca gtcactgaat      60
ctcaaggtcc ttacaatgaa atgcagctgg gtcatcttct tcctgatggc agtggttata     120
ggaatcaatt cagaggttca gctgcagcag tctggggcag agcttgtgag gtcaggggcc     180
tcagtcaact tgtcctgcac agcttctggc ttcaacatta aagactacta tatacactgg     240
gtgaagcaga ggcctgaacg gggcctggag tggattggat ggattgatcc tgagaatggt     300
gatactgaat atgccccgga gttccagggc aaggcctcta tgactgcaga cacatcctcc     360
aacacagcct acctgcagct cagcagcctg acatctgagg acactgccgt ctattactgt     420
aagcgagggg actgggccca agggactctg gtcactgtct ctgcagccaa aacgacaccc     480
ccatctgtct atccactggc ccctggatct gctgcccaaa ctaactccat ggtgaccctg     540
ggatgcctgg tcaagggcta tttccctgag ccagtgacag tgacctggaa ctctggatcc     600
ctgtccagcg gtgtgcacac cttcccagca agcttggcgt aatcatggtc atagctgttt     660
cctgtgtgaa attgttatcc gctcacaatt ccacacaaca tacgagccgg aagcataaag     720
tgtaaagcct ggggtgcct aatgagtgag ctaactcaca ttaattgcgt tgcgctcact     780
gcccgctttc cagtcgggaa acctgtcgtg ccagctgcat taatgaatcg ccaacgcgc     840
```

```
ggggagaggc ggtttgcgta ttgggcgctc ttccgcttcc tcgctcactg actcgctgcg      900
ctcggtcgtt cggctgcggc gagcggtatc agctcactca aaggcggtaa tacggttatc      960
cacagaatca ggggatacgc agaaagaaca tgtgagcaaa aggccagcaa aagccaggga     1020
ccgtaaaagc cgcgttgctg cgttttcata ggctccgccc ccctgacgag catcacaaaa     1080
tcgacgcctc agtcagaagg                                                 1100
```

```
<210> SEQ ID NO 6
<211> LENGTH: 334
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
gaggttcagc tgcagcagtc tggggcagag cttgtgaggt caggggcctc agtcaacttg       60
tcctgcacag cttctggctt caacattaaa gactactata tacactgggt gaagcagagg      120
cctgaacggg gcctggagtg gattggatgg attgatcctg agaatggtga tactgaatat      180 gcccccggagt tccagggcaa ggcctctatg actgcagaca tcctccaa cacagcctac      240 ctgcagctca gcagcctgac atctgaggac actgccgtct attactgtaa gcgaggggac      300
tggggccaag ggactctggt cactgtctct gcag                                 334
```

```
<210> SEQ ID NO 7
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Gln Gln Ser Gly Ala Glu Leu Val Arg Ser Gly Ala
1               5                   10                  15

Ser Val Asn Leu Ser Cys Thr Ala Ser Gly Phe Asn Ile Lys Asp Tyr
            20                  25                  30

Tyr Ile His Trp Val Lys Gln Arg Pro Glu Arg Gly Leu Glu Trp Ile
        35                  40                  45

Gly Trp Ile Asp Pro Glu Asn Gly Asp Thr Glu Tyr Ala Pro Glu Phe
    50                  55                  60

Gln Gly Lys Ala Ser Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Lys Arg Gly Asp Trp Gly Gln Gly Thr Leu Val Thr Val Ser Ala
            100                 105                 110
```

```
<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Phe Asn Ile Lys Asp Tyr Tyr
1               5
```

```
<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ggcttcaaca ttaaagacta ctat                                           24

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ile Asp Pro Glu Asn Gly Asp Thr
1               5

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
attgatcctg agaatggtga tact                                           24

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Arg Gly Asp
1

<210> SEQ ID NO 13
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aagcgagggg ac                                                        12

<210> SEQ ID NO 14
<211> LENGTH: 1100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
```

-continued

```
agctgagtat caacgcagag tacatgggga ctgatcagtc tcctcaggct gtctcctcag      60
gttgcctcct caaaatgaag ttgcctgtta ggctgttggt gctgatgttc tggattcctg     120
cttccagcag tgatgttttg atgacccaaa ctccactctc cctgcctgtc agtcttggag     180
atcaagcctc catctcttgc agatctagtc agagcattgt acatagtaat ggaaacacct     240
atttagaatg gttcctgcag aaaccaggcc agtctccaaa gctcctgatc tacaaagttt     300
ccaaccgatt ttctggggtc ccagacaggt tcagtggcag tggatcaggg acagatttca     360
cactcaagat cagcagagtg gaggctgagg atctgggagt ttattactgc tttcaaggtt     420
cacatgctcc attcacgttc ggctcgggga cagagttgga aataaaacgg gctgatgctg     480
caccaactgt atccatcttc ccaccatcca gtgagcaagc ttggcgtaat catggtcata     540
gctgtttcct gtgtgaaatt gttatccgct cacaattcca cacaacatac gagccggaag     600
cataaagtgt aaagcctggg gtgcctaatg agtgagctaa ctcacattaa ttgcgttgcg     660
ctcactgccc gctttccagt cgggaaacct gtcgtgccag ctgcattaat gaatcggcca     720
acgcgcgggg agaggcggtt tgcgtattgg ggcgctcttc cgcttcctcg ctcactgact     780
cgctgcgctc ggtcgttcgg ctgcggcgag cggtatcagc tcactcaaag gcggtaatac     840
ggttatccac agaatcaggg gataacgcag aaagaacatg tgagcaaaag gccagcaaaa     900
ggccaggaac cgtaaaaagg ccgcgttgct ggcgtttttc cataggctcc gcccccctgac    960 gagcatcaca aaatcgacgc tcaagtcaga ggtggcgaaa cccgacagga ctataaagat    1020
accaggcgtt tcccctgaag ctccctcgtg cgctctctgt tcgaccctgc gctacgatac    1080
tgtcgcttct ccttcggagc                                                1100
```

```
<210> SEQ ID NO 15
<211> LENGTH: 337
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
gatgttttga tgacccaaac tccactctcc ctgcctgtca gtcttggaga tcaagcctcc      60
atctcttgca gatctagtca gagcattgta catagtaatg gaaacaccta tttagaatgg     120
ttcctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgctcca     300
ttcacgttcg gctcggggac agagttggaa ataaaac                              337
```

```
<210> SEQ ID NO 16
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Phe Leu Gln Lys Pro Gly Gln Ser
```

```
      35                40                45
Pro Lys Leu Leu Ile Tyr Lys Val Ser Asn Arg Phe Ser Gly Val Pro
    50                55                60

Asp Arg Phe Ser Gly Ser Gly Ser Gly Thr Asp Phe Thr Leu Lys Ile
65                70                75                80

Ser Arg Val Glu Ala Glu Asp Leu Gly Val Tyr Tyr Cys Phe Gln Gly
                85                90                95

Ser His Ala Pro Phe Thr Phe Gly Ser Gly Thr Glu Leu Glu Ile Lys
            100                105                110
```

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Gln Ser Ile Val His Ser Asn Gly Asn Thr Tyr
1               5                10
```

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18

```
cagagcattg tacatagtaa tggaaacacc tat                                    33
```

<210> SEQ ID NO 19
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19

```
aaagtttcc                                                               9
```

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Phe Gln Gly Ser His Ala Pro Phe Thr
1               5
```

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21

-continued

```
tttcaaggtt cacatgctcc attcacg                                              27
```

```
<210> SEQ ID NO 22
<211> LENGTH: 1100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
ggttggtatc aacgcagagt acatggggac atatgaacac tgttttctct acagtcactg      60
aatctcaagg tccttacaat gaaatgcagc tgggtcatct tcttcctgat ggcagtggtt     120
ataggaatca attcagaggt tcagctgcag cagtctgggg cagagcttgt gaggtcaggg     180
gcctcagtca acttgtcctg cacagcttct ggcttcaaca ttaaagacta ctatatacac     240
tgggtgaagc agaggcctga acggggcctg gagtggattg gatggattga tcctgagaat     300
ggtgatactg aatatgcccc ggagttccag ggcaaggcct ctatgactgc agacacatcc     360
tccaacacag cctacctgca gctcagcagc ctgacatctg aggacactgc cgtctattac     420
tgtaagcgag gggactgggg ccaagggact ctggtcactg tctctgcagc caaaacgaca     480
cccccatctg tctatccact ggcccctgga tctgctgccc aaactaactc catggtgacc     540
ctgggatgaa gcttggcgta atcatggtca tagctgtttc ctgtgtgaaa ttgttatccg     600
ctcacaattc cacacaacat acgagccgga agcataaagt gtaaagcctg gggtgcctaa     660
tgagtgagct aactcacatt aattgcgttg cgctcactgc ccgctttcca gtcgggaaac     720
ctgtcgtgcc agctgcatta atgaatcggc caacgcgcgg ggagaggcgg tttgcgtatt     780
gggcgctctt ccgcttcctc gctcactgac tcgctgcgct cggtcgttcg ctgcggcga     840 gcggtatcag ctcactcaaa ggcggtaata cggttatcca cagaatcagg ggataacgca     900
ggaaagaaca tgtgagcaaa aggccagcaa aggccaggaa ccgtaaaaag gccgcgttgc     960
tggcgttttc cataggctcc gcccccctgac gagcatcaca aaaatcgacg ctcagtcaga    1020
ggtggcgaaa cccgacagga ctataagata caggcgtttc ccctggagct cctcgtgcgc    1080
tctctgtcga cctgcgctac                                                 1100
```

```
<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Phe Asn Ile Lys Asp Tyr Tyr Ile His
1               5
```

```
<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Trp Ile Gly Trp Ile Asp Pro Glu Asn Gly Asp Thr Glu Tyr Ala
1               5                   10                  15
```

<210> SEQ ID NO 25
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Ser Ile Val His Ser Asn Gly Asn Thr Tyr Leu Glu
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Leu Leu Ile Tyr Lys Val Ser Asn Arg Phe Ser
1               5                   10

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Phe Gln Gly Ser His Ala Pro Phe
1               5

<210> SEQ ID NO 28
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
gacattgtga tgacccagtc tcaaaaattc atgtccacat cagtaggaga cagggtcagc        60
gtcacctgca aggccagtca gaatgtgggt actaacgtag cctggtatca acagaaacca       120
gggcaatctc ccaaagcact gattcactcg gcatcctacc ggtacagtgg agtccctgat       180
cgcttcacag gcagtggatc tgggacagat ttcactctca ccatcagcaa tgtgcagtct       240
gaagacttgg cagagtattt ctgtcagcaa tataacagct atccgctcac gttcggtgct       300
gggaccaagc tggagctgaa a                                                 321

<210> SEQ ID NO 29
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Ile Val Met Thr Gln Ser Gln Lys Phe Met Ser Thr Ser Val Gly
1               5                   10                  15

```
Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

His Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ala Gly Thr Lys Leu Glu Leu Lys
            100                 105
```

```
<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Asn Val Gly Thr Asn
1               5
```

```
<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cagaatgtgg gtactaac                                                        18
```

```
<210> SEQ ID NO 32
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32 tcggcatcc                                                                   9
```

```
<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Gln Tyr Asn Ser Tyr Pro Leu Thr
1               5
```

```
<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 34
cagcaatata acagctatcc gctcacg                                                27

<210> SEQ ID NO 35
<211> LENGTH: 1100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
cccaaactaa aatagggcag cagtggtatc aacgcagagt acatggggga aatacatcag      60
atcagcatgg gcatcgagat ggagtcacag actcaggtct ttgtttacat gttgctgtgg     120
ttgtctggtg ttgatggaga cattgtgatg acccagtctc aaaaattcat gtccacatca     180
gtaggagaca gggtcagcgt cacctgcaag gccagtcaga atgtgggtac taacgtagcc     240
tggtatcaac agaaaccagg gcaatctccc aaagcactga ttcactcggc atcctaccgg     300
tacagtggag tccctgatcg cttcacaggc agtggatctg ggacagattt cactctcacc     360
atcagcaatg tgcagtctga agacttggca gagtatttct gtcagcaata taacagctat     420
ccgctcacgt tcggtgctgg gaccaagctg gagctgaaac gggctgatgc tgcaccaact     480
gtatccatct tcccaccatc cagtgagcaa gcttggcgta atcatggtca tagctgtttc     540
ctgtgtgaaa ttgttatccg ctcacaattc cacacaacat acgagccgga agcataaagt     600
gtaaagcctg gggtgcctaa tgagtgagct aactcacatt aattgcgttg cgctcactgc     660
ccgctttcca gtcgggaaac ctgtcgtgcc agctgcatta tgaatcggc caacgcgcgg      720 ggagaggcgg tttgcgtatt ggggcgctct tccgcttcct cgctcactga ctcgctgcgc     780
tcggtcgttc ggctgcggcg agcggtatca gctcactcaa aggcggtaat acggttatcc     840
acagaatcag ggggataacg cacgaaagaa catgtgagca aaaggccagc aaaggccagg     900
aaccgtaaaa aggccgcgtt gctggcgttt ttccataggc tccgcccct gacagcatca     960 caaaatcgac gctcagtcaa ggtggcgaat ccggacagga ctataagaat accaggcgtt    1020
tccccatgga agttcctcgg cgtccttcc tgtcccgacc ctgccgctac cggaatacct    1080
ggtcgccttt ctccccatcc                                                      1100

<210> SEQ ID NO 36
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
gaggtccagc tgcaacagtc tggacctgag ctggtgaagc ctggggcttc agtgaagata      60
tcctgcaaga cttctggata cacattcact gaagacacca tgcactgggt gaagcagagc     120 catgaaaga gccttgagtg gattggaggt attaatccta caagggtgg tactagctac       180 aaccagaagt tcaaggacaa ggccacattg actgtagaca gtcctccag cacagcctac      240 atggagctcc gcagcctgac atctgaggat tctgcagtct attactgtgc tacgctggta     300
gactactggg gccaaggcac cactctcaca gtctcctca                                339

```
<210> SEQ ID NO 37
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Asp
            20                  25                  30

Thr Met His Trp Val Lys Gln Ser His Gly Lys Ser Leu Glu Trp Ile
        35                  40                  45

Gly Gly Ile Asn Pro Asn Lys Gly Gly Thr Ser Tyr Asn Gln Lys Phe
    50                  55                  60

Lys Asp Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Thr Leu Val Asp Tyr Trp Gly Gln Gly Thr Thr Leu Thr Val Ser
            100                 105                 110

Ser

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Tyr Thr Phe Thr Glu Asp Thr
1               5

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ggatacacat tcactgaaga cacc                                              24

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ile Asn Pro Asn Lys Gly Gly Thr
1               5

<210> SEQ ID NO 41
<211> LENGTH: 24
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 41
attaatccta acaagggtgg tact                                            24

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Thr Leu Val Asp Tyr
1               5

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gctacgctgg tagactac                                                  18

<210> SEQ ID NO 44
<211> LENGTH: 1100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
tcattactac tataggggca agcagtggta tcaacgcaga gtacatgggg atatgtccaa    60
tgtcctctcc tcagacactg aacacactga ctctaaccat gggatggagc tggatctttc   120
tctttctcct gtcaggaact gcaggtgtcc tctctgaggt ccagctgcaa cagtctggac   180
ctgagctggt gaagcctggg gcttcagtga agatatcctg caagacttct ggatacacat   240
tcactgaaga caccatgcac tgggtgaagc agagccatgg aaagagcctt gagtggattg   300
gaggtattaa tcctaacaag ggtggtacta gctacaacca gaagttcaag gacaaggcca   360
cattgactgt agacaagtcc tccagcacag cctacatgga gctccgcagc ctgacatctg   420
aggattctgc agtctattac tgtgctacgc tggtagacta ctggggccaa ggcaccactc   480
tcacagtctc ctcagccaaa acgacacccc catctgtcta tccactggcc cctggatctg   540
ctgcccaaac taactccatg gtgaccctgg gatgcctggt caagggctat ttccctgagc   600
cagtgacagt gacctggaac tctggatccc aagcttggcg taatcatggt catagctgtt   660
tcctgtgtga aattgttatc cgctcacaat tccacacaac atacgagccg gaagcataaa   720
gtgtaaagcc tggggtgcct aatgagtgag ctaactcaca ttaattgcgt tgcgctcact   780
gcccgctttc cagtcgggaa acctgtcgtg ccagctgcat taatgaatcg gccaacgcgc   840
ggggagaggc ggtttgcgta ttgggcgctc ttccgcttcc tcgctcactg actcgctgcg   900
ctcggtcgtt cggctgcggg cgagcggtat cagctcactc aaaggcggta atacggttat   960
ccacagaatc aggggataac gcaggaaaga acatgtgagc aaaaggccag caaaaggcca  1020
```

```
ggacccgtaa aaaggccgcg ttgctggcgt tttccaatag cctccgcccc ccctgacgag      1080
catcacaaaa aatcgacgct                                                  1100

<210> SEQ ID NO 45
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
gatgttgtga tgacccaaac tccagtctcc ctgcctgtca gtcttggaga tcaagcctcc        60
atctcttgca gatctactca gagccttgta cacagtaatg gacacaccta tttacattgg       120
tacctgcaga agccaggcca gtctcctaag ctcctgatct acaaagtttc caaccgattt       180
tctggggtcc cagacaggtt cagtggcact ggatcaggga cagatttcac actcaagatc       240
agcagagtgg aggctgagga tctgggagtt tatttctgct ctcaaagtac acatgttccg       300
tacacgttcg gaggggggac caagctggaa ataaaa                                 336

<210> SEQ ID NO 46
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asp Val Val Met Thr Gln Thr Pro Val Ser Leu Pro Val Ser Leu Gly
1               5                   10                  15

Asp Gln Ala Ser Ile Ser Cys Arg Ser Thr Gln Ser Leu Val His Ser
                20                  25                  30

Asn Gly His Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Thr Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Ser Leu Val His Ser Asn Gly His Thr Tyr
1               5                   10

<210> SEQ ID NO 48
<211> LENGTH: 33
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 48
cagagccttg tacacagtaa tggacacacc tat                                    33

<210> SEQ ID NO 49
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49 aaagtttcc                                                                9

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ser Gln Ser Thr His Val Pro Tyr Thr
1               5

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
tctcaaagta cacatgttcc gtacacg                                           27

<210> SEQ ID NO 52
<211> LENGTH: 1100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (994)..(994)
<223> OTHER INFORMATION: a, c, t, g, unknown or other
<220> FEATURE:
<221> NAME/KEY: modified_base
<222> LOCATION: (1020)..(1020)
<223> OTHER INFORMATION: a, c, t, g, unknown or other
<220> FEATURE:
<221> NAME/KEY: modified_base
<222> LOCATION: (1068)..(1068)
<223> OTHER INFORMATION: a, c, t, g, unknown or other
<220> FEATURE:
<221> NAME/KEY: modified_base
<222> LOCATION: (1072)..(1072)
<223> OTHER INFORMATION: a, c, t, g, unknown or other
<220> FEATURE:
<221> NAME/KEY: modified_base
<222> LOCATION: (1088)..(1088)
<223> OTHER INFORMATION: a, c, t, g, unknown or other
<220> FEATURE:
<221> NAME/KEY: modified_base
<222> LOCATION: (1100)..(1100)
```

-continued

<223> OTHER INFORMATION: a, c, t, g, unknown or other

<400> SEQUENCE: 52

```
ggcagcagtg gtatcaacgc agagtacatg ggggatcagt ctcctcaggc tgtctcctca      60
ggcttgcctc ctcaaaatga agttgcctgt taggctgttg gtgctgatgt tctggattcc     120
tgcttccagc agtgatgttg tgatgaccca aactccagtc tccctgcctg tcagtcttgg     180
agatcaagcc tccatctctt gcagatctac tcagagcctt gtacacagta atggacacac     240
ctatttacat tggtacctgc agaagccagg ccagtctcct aagctcctga tctacaaagt     300
ttccaaccga ttttctgggg tcccagacag gttcagtggc actggatcag ggacagattt     360
cacactcaag atcagcagag tggaggctga ggatctggga gtttatttct gctctcaaag     420
tacacatgtt ccgtacacgt tcggagggg gaccaagctg gaaataaaac gggctgatgc     480
tgcaccaact gtatccatct tcccaccatc cagtgagcaa gcttggcgta atcatggtca     540
tagctgtttc ctgtgtgaaa ttgttatccg ctcacaattc cacacaacat acgagccgga     600
agcataaagt gtaaagcctg gggtgcctaa tgagtgagct aactcacatt aattgcgttg     660
cgctcactgc ccgctttcca gtcgggaaac ctgtcgtgcc agctgcatta atgaatcggc     720
caacgcgcgg ggagaggcgg tttgcgtatt gggcgctctt ccgcttcctc gctcactgac     780
tcgctgcgct cggtcgttcg ctgcggcga gcggtatcag ctcactcaaa ggcggtaata     840
cggttatcca cagaatcagg ggataacgca ggaaagaaca tgtgagcaaa aggccagcaa     900
aaggccagga accgtaaaaa ggccgcgttg ctggcgtttt tccataggct ccgcccccc     960 tgacgagcat cacaaaaatc gacgctcaag tcanaggtgg cgaaacccga caggactatn    1020
aagataccag gcgtttcccc ctggaagctc cctcgtgcgc tctcctgntc cnacctgccg    1080
cttaccgnaa actgtccgcn                                                 1100
```

<210> SEQ ID NO 53
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

```
caagttactc taaaagagtc tggccctggg atattgaagc cctcacagac cctcagtctg      60
acttgttctt tctctgggtt ttcactgagc acttctggtg tgggtgtagg ctggattcgt     120
cagccttcag ggaagggtct ggagtggctg gcacacattt ggtgggatga tgatgagtac     180
tataacccat ccctgaagag ccagctcaca atctccaagg atacctccag aaaccaggta     240
ttcctcaaga tcaccagtgt ggacacttca gatactgcca cttactactg tgctcgccga     300
tactacgggg acgctatgga ctactggggt caaggaaccg cagtcaccgt ctcctcc       357
```

<210> SEQ ID NO 54
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Gln Val Thr Leu Lys Glu Ser Gly Pro Gly Ile Leu Lys Pro Ser Gln
1               5                   10                  15
```

```
Thr Leu Ser Leu Thr Cys Ser Phe Ser Gly Phe Ser Leu Ser Thr Ser
            20                  25                  30

Gly Val Gly Val Gly Trp Ile Arg Gln Pro Ser Gly Lys Gly Leu Glu
        35                  40                  45

Trp Leu Ala His Ile Trp Trp Asp Asp Asp Glu Tyr Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ser Asp Thr Ala Thr Tyr Tyr
                85                  90                  95

Cys Ala Arg Arg Tyr Tyr Gly Asp Ala Met Asp Tyr Trp Gly Gln Gly
            100                 105                 110

Thr Ala Val Thr Val Ser Ser
        115
```

```
<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Phe Ser Leu Ser Thr Ser Gly Val Gly
1               5                   10
```

```
<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gggttttcac tgagcacttc tggtgtgggt                                    30
```

```
<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ile Trp Trp Asp Asp Asp Glu
1               5
```

```
<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
atttggtggg atgatgatga g                                             21
```

```
<210> SEQ ID NO 59
<211> LENGTH: 11
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 59

Ala Arg Arg Tyr Tyr Gly Asp Ala Met Asp Tyr
1               5                   10

<210> SEQ ID NO 60
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gctcgccgat actacgggga cgctatggac tac                                   33

<210> SEQ ID NO 61
<211> LENGTH: 1100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
tcattaataa ggggggcaag cagtggtatc aacgcagagt acatggggac acaagtgtgc      60
agacatggac aggcttactt cttcattcct gctgctgatt gtccctgcat atgtcttgtc     120
ccaagttact ctaaaagagt ctggccctgg gatattgaag ccctcacaga ccctcagtct     180
gacttgttct ttctctgggt tttcactgag cacttctggt gtgggtgtag gctggattcg     240
tcagccttca gggaagggtc tggagtggct ggcacacatt tggtgggatg atgatgagta     300
ctataaccca tccctgaaga gccagctcac aatctccaag gatacctcca gaaaccaggt     360
attcctcaag atcaccagtg tggacacttc agatactgcc acttactact gtgctcgccg     420
atactacggg gacgctatgg actactgggt caaggaacc gcagtcaccg tctcctccgc      480
caaaacgaca cccccatctg tctatccact ggcccctgga tctgctgccc aaactaactc     540
catggtgacc ctgggatgcc tggtcaaggg ctatttccct gagccagtga cagtgacctg     600
gaactctgga tcccaagctt ggcgtaatca tggtcatagc tgtttcctgt gtgaaattgt     660
tatccgctca caattccaca caacatacga gccggaagca taaagtgtaa agcctggggt     720
gcctaatgag tgagctaact cacattaatt gcgttgcgct cactgcccgc tttccagtcg     780
ggaaacctgt cgtgccagct gcattaatga atcggccaac gcgcggggag aggcggtttg     840
cgtattgggc gctcttccgc ttcctcgctc actgactcgc tgcgctcggt cgttcggctg     900
cggcgagcgg tatcagctca ctcaaaggcg gtaatacggt tatccacaga atcaggggat     960
acgcagaaga acatgtgagc aaaaggccag caaaaggcca ggaaccgtaa aaggccgcgt    1020
tgctggcgtt tttccatagg ctcgccccc tgacgagcat cacaaaaaat cgacgctcag    1080
tcagaggtgg cgaaaccgac                                                1100
```